US 8,187,872 B2

United States Patent
Allen et al.

(10) Patent No.: US 8,187,872 B2
(45) Date of Patent: *May 29, 2012

(54) LENTIVIRAL VECTORS PSEUDOTYPED WITH A SINDBIS VIRUS ENVELOPE GLYCOPROTEIN

(75) Inventors: James M. Allen, Seattle, WA (US); Thomas W. Dubensky, Jr., Seattle, WA (US); Jin Zhong Li, Belmont, CA (US); Derek D. Sloan, Seattle, WA (US); Neal Van Hoeven, Seattle, WA (US)

(73) Assignee: Immune Design Corp., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/277,900

(22) Filed: Oct. 20, 2011

(65) Prior Publication Data

US 2012/0039932 A1    Feb. 16, 2012

Related U.S. Application Data

(63) Continuation of application No. 12/842,609, filed on Jul. 23, 2010.

(60) Provisional application No. 61/228,491, filed on Jul. 24, 2009.

(51) Int. Cl.
C12N 15/00 (2006.01)
A61K 39/00 (2006.01)

(52) U.S. Cl. ................... 435/320.1; 424/199.1

(58) Field of Classification Search .......... None
See application file for complete search history.

(56) References Cited

U.S. PATENT DOCUMENTS

| | | | |
|---|---|---|---|
| 5,168,062 A | 12/1992 | Stinski | |
| 5,298,420 A | 3/1994 | Chang | |
| 5,385,839 A | 1/1995 | Stinski | |
| 6,013,516 A | 1/2000 | Verma et al. | |
| 6,017,761 A | 1/2000 | Rigg et al. | |
| 6,140,114 A | 10/2000 | Klatzmann et al. | |
| 6,218,181 B1 | 4/2001 | Verma et al. | |
| 6,297,004 B1 | 10/2001 | Russell et al. | |
| 6,306,401 B1 | 10/2001 | Brown et al. | |
| 6,416,997 B1 | 7/2002 | Mir-Shekari et al. | |
| 6,432,699 B1 | 8/2002 | Meruelo et al. | |
| 6,531,123 B1 | 3/2003 | Chang | |
| 6,534,064 B1 | 3/2003 | O'Hagan et al. | |
| 6,627,442 B1 | 9/2003 | Humeau et al. | |
| 6,830,892 B2 | 12/2004 | Marasco et al. | |
| 7,033,834 B2 | 4/2006 | Valerio et al. | |
| 7,090,837 B2 | 8/2006 | Spencer et al. | |
| 7,195,916 B2 | 3/2007 | Qin et al. | |
| 7,285,642 B2 | 10/2007 | Figdor et al. | |
| 7,323,619 B2 | 1/2008 | Baltimore et al. | |
| 7,429,481 B2 | 9/2008 | Bergman et al. | |
| 7,455,833 B2 | 11/2008 | Thorpe et al. | |
| 7,604,802 B2 | 10/2009 | O'Hagan et al. | |
| 7,611,712 B2 | 11/2009 | Karp | |
| 7,612,173 B2 | 11/2009 | Abrecht et al. | |
| 7,638,133 B2 | 12/2009 | Honda et al. | |
| 7,771,979 B2 | 8/2010 | Polo et al. | |
| 2002/0155430 A1 | 10/2002 | Marsco et al. | |
| 2003/0059944 A1 | 3/2003 | Lois-Caballe et al. | |
| 2003/0068821 A1 | 4/2003 | Lois-Caballe et al. | |
| 2003/0101471 A1 | 5/2003 | Baltimore et al. | |
| 2003/0129163 A1 | 7/2003 | Hall et al. | |
| 2004/0091853 A1 | 5/2004 | Hazuda et al. | |
| 2005/0003547 A1 | 1/2005 | Spencer et al. | |
| 2007/0275873 A1* | 11/2007 | Heidner et al. ............... 514/2 |
| 2008/0003682 A1 | 1/2008 | Lois-Caballe et al. | |
| 2008/0019998 A1* | 1/2008 | Wang et al. ............ 424/199.1 |
| 2008/0134352 A1 | 6/2008 | Baltimore et al. | |
| 2008/0227736 A1 | 9/2008 | Chen et al. | |
| 2010/0184206 A1 | 7/2010 | Chen et al. | |

FOREIGN PATENT DOCUMENTS

| | | |
|---|---|---|
| WO | WO-96/17072 A2 | 6/1996 |
| WO | WO-00/09730 A2 | 2/2000 |
| WO | WO-00/61772 A2 | 10/2000 |
| WO | WO-01/16342 A1 | 3/2001 |
| WO | WO-2004/056966 A2 | 7/2004 |
| WO | WO-2004/067710 A2 | 8/2004 |
| WO | WO-2005/118802 A2 | 12/2005 |
| WO | WO-2006/130855 A2 | 12/2006 |
| WO | WO-2008/011636 A2 | 1/2008 |
| WO | WO 2009/076524 * | 6/2009 |

OTHER PUBLICATIONS

Byrnes et al., Journal of Virology, 2000, 74(2):644-651.*
Russell et al., Journal of Virology, 1989, 63(4):1619-1629.*
Singh et al., Molecular Immunology, 2009, 47:164-174.*
Shortman et al., Experimental and Molecular Medicine, 2009, 41(2):61-66.*
Apolonia et al., "Stable Gene Transfer to Muscle Using Non-integrating Lentiviral Vectors," Molecular Therapy 15:1947-1954, 2007.
Bayer et al., "A Large U3 Deletion Causes Increased In Vivo Expression From a Nonintegrating Lentiviral Vector," Molecular Therapy 16:1968-1976, 2008.
Bear et al., "Heparin-binding and patterns of virulence for two recombinant strains of Sindbis virus," Virology 347:183-190, 2006.
Breckpot et al., "Lentiviral vectors for cancer immunotherapy: transforming infectious particles into therapeutics," Gene Therapy 14:847-862, 2007.

(Continued)

*Primary Examiner* — Zachariah Lucas
*Assistant Examiner* — Nicole Kinsey White
(74) *Attorney, Agent, or Firm* — Marshall, Gerstein & Borun LLP

(57) ABSTRACT

Lentiviral vector particles comprising a Sindbis virus E2 glycoprotein variant and a lentiviral vector genome comprising a sequence of interest are provided. A lentiviral vector particle comprising: (a) an envelope comprising a Sindbis virus E2 glycoprotein variant; and (b) a lentiviral vector genome comprising a sequence of interest; wherein the E2 glycoprotein variant facilitates infection of dendritic cells by the lentiviral vector particle, and wherein the E2 glycoprotein variant has reduced binding to heparan sulfate compared to a reference sequence (HR strain).

30 Claims, 13 Drawing Sheets

OTHER PUBLICATIONS

Cockrell et al., "Gene delivery by lentivirus vectors," Mol. Biotechnol. 36:184-204, 2007.

Coutant et al., "Protective Antiviral Immunity Conferred by a Nonintegrative Lentiviral Vector-Based Vaccine," Plos ONE 3:e3973:1-6, 2008.

Dai et al., "HIV-I Gag-specific immunity induced by a lentivector-based vaccine directed to dendritic cells," Proc. Natl. Acad. Sci. U. S. A. 106:20382-20387, 2009.

Engering et al., "Subset of DC-SIGN dendritic cells in human blood transmits HIV-1 to T lymphocytes," Blood 100(5):1780-1786, 2002.

Gardner et al., "Infection of Human Dendritic Cells by a Sindbis Virus Replicon Vector Is Determined by a Single Amino Acid Substitution in the E2 Glycoprotein," J. Virol. 74:11849-11857, 2000.

Geijtenbeek et al., "Self- and Nonself-Recognition by C-Type Lectins on Dendritic Cells," Annu. Rev. Immunol. 22:33-54, 2004.

Kielian et al., "Alphavims Entry and Membrane Fusion," Viruses 2:796-825, 2010.

Klimstra et al., "Adaptation of Sindbis Virus to BHK Cells Selects for Use of Heparan Sulfate as an Attachment Receptor," J. Virol. 72:7357-7366, 1998.

Klimstra et al., "DC-SIGN and L-SIGN Can Act as Attachment Receptors for Alphaviruses and Distinguish between Mosquito Cell- and Mammalian Cell-Derived Viruses,".I. Virol. 77:12022-12032, 2003.

Klimstra et al., "The Furin Protease Cleavage Recognition Sequence of Sindbis Virus PE2 Can Mediate Virion Attachment to Cell Surface Heparan Sulfate," J. Virol. 73:6299-6306, 1999.

Lu et al., "Therapeutic dendritic-cell vaccine for chronic HIV-1 infection," Nature Medicine 10(12)1 359-1365, 2004.

McKnight et al., "Deduced consensus sequence of Sindbis virus strain AR339: mutations contained in laboratory strains which affect cell culture and in vivo phenotypes," J. Virol. 70:1981-1989, 1996.

Miyoshi et al., "Development of a self-inactivating lentivirus vector," J. Virol. 72:8150-8157, 1998.

Morizono et al., Antibody-Directed Targeting of Retroviral Vectors via Cell Surface Antigens, Viral. 75:8016-8020, 2001.

Morizono et al., "Lentiviral vector retargeting to P-glycoprotein on metastatic melanoma through intravenous injection," Nature Medicine 11:346-352, 2005.

Morizono et al., "Redirecting Lentiviral Vectors Pesudotyped with Sindbis Virus-Derived Envelope Proteins to DC-SIGN by Modification of N-Linked Glycans of Envelope Proteins," Journal of Virology 84(14):6923-6934, 2010.

Mukhopadhyay et al., "A structural perspective of the flavivirus life cycle," Nature Rev. 1 icrobial. 3:13-22, 2005.

Navaratnarajah et al., "Functional characterization of the Sindbis virus E2 glycoprotein by transposon linker-insertion mutagenesis," Virology 363:134-147, 2007.

Negri et al. Successful immunization with a single injection of nonintegrating lentiviral vector, Mol. Ther. 15:1716-1723, 2007.

Ohno et al., "Cell-specific targeting of Sindbis virus vectors displaying IgG-binding domains of protein A," Nature Biotechnology 15:763-767, 1997.

Papagatsias et al., "Activity of different vaccine-associated promoter elements in human dendritic cells," Immunol. Lett. 115:117-125, 2008.

Pauwels, et al., "State-of-the-Art Lentiviral Vectors for Research Use: Risk Assessment and Biosafety Recommendations," Current Gene Therapy 9:459-474, 2009.

Pfeifer et al., "Gene therapy: promises and problems," Annu. Rev. Genomics Hum. Genet. 2:177-211, 2001.

Philippe et al., "Lentiviral vectors with a defective integrase allow efficient and sustained transgene expression in vitro and in vivo," Proc. Natl. Acad. Sci. USA 103:17684-17689, 2006.

Reed et al., "New horizons in adjuvants for vaccine development," Trends in Immunology 30:23-32, 2009.

Sharkey et al., "Ross River Virus Glycoprotein-Pseudotyped Retroviruses and Stable Cell Lines for Their Production,"I Virol. 75:2653-2659, 2001.

Shiver et al., "Recent Advances in the Development of HIV-1 Vaccines Using Replication-Incompetent Adenovirus Vectors," Annu. Rev. Med. 55:355-372, 2004.

Shresta et al., "Critical Roles for Both STAT 1-Dependent and STAT I-Independent Pathways in the Control of Primary Dengue Virus Infection in Mice," The Journal of Immunology 175:3946-3954, 2005.

Smit et al., "PE2 Cleavage Mutants of Sindbis Virus: Correlation between Viral Infectivity and pH-Dependent Membrane Fusion Activation of the Spike Heterodimer,"J. Virol. 75:11196-11204, 2001.

Strang et at, "Human Immunodeficiency Virus Type 1 Vectors with Alphavirus Envelope Glycoproteins Produced from Stable Packaging Cells,"I Virol. 79:1765-1771, 2005.

Strauss et al., "The alphaviruses: gene expression, replication, and evolution," Microhiol. Rev. 58:491-562, 1994.

West et al., "Mutations in the endodomain of Sindbis virus glycoprotein E2 define sequences critical for virus assembly," J. Virol. 80:4458-4468, 2006.

Yang et al., "Targeted lentiviral vectors to specific cell types in vivo," Proc. Natl. Acad. Sci. USA 103(31):11479-11484, 2006.

Yang et al., "Engineered lentivector targeting of dendritic cells for in vivo immunization," Nature Biotechnology 26:326-334, 2008.

Zarei et al., "Transduction of dendritic cells by antigen-encoding lentiviral vectors permits antigen processing and MHC class I-dependent presentation," J. Allergy Clin. Immunol. 109:988-994, 2002.

Zennou et al., "HIV-1 Genome Nuclear Import is Mediated by a Central DNA Flap," Cell 101:173-185, 2000.

Zufferey et al., "Self-Inactivating Lentivirus Vector for Safe and Efficient In Vivo Gene Delivery," J. Viral. 72:9873-9880, 1998.

International search report from Application No. PCT/US2010/042870, dated Sep. 22, 2010.

Ageichik et al., Lentivector trargeting to dendritic cells. *Molec. Ther.*, 16(6): 1008-09 (2008).

Analyses of Merck's HIV vaccine Step' study. The Medical News, Nov. 12, 2008, Accessed at http://www.new-medical.net/news/2008/11/12/42892.aspx on Nov. 20, 2009.

Bailey et al., Transmission of human immunodeficiency virus type 1 from a patient who developed AIDS to an elite suppressor, *J. Viral.*, 82(15): 7395-410 (2008).

Banchereau et al., Dendritic cells and the control of immunity, *Nature*, 392: 245-52 (1998).

Banchereau et al., Dendritic cells as therapeutic vaccines against cancer, *Nat. Rev. Immunol.*, 5: 296-306 (2005).

Bangham et al., What is required of an HIV vaccine? *Lancet*, 350: 1617-21 (1997).

Barouch et al., Adenovirus vector-based vaccines for human immunodeficiency virus type 1, *Hum. Gene. Ther.*, 16: 149-56 (2005).

Barouch et al., Challenges in the development of an HIV-1 vaccine, *Nat. Rev.*, 455: 613-9 (2008).

Belousova et al., Genetically targeted adenovirus vector directed to CD40-expressing cells, *J. Virol.*, 77: 11367-77 (2003).

Bhardwaj et al., Interactions of viruses with dendritic cells: A double-edged sword. *J. Exp. Med.*, 186(6): 795-9 (1997).

Bonifaz et al., Efficient targeting of protein antigen to the dendritic cell receptor DEC-205 in the steady state leads to antigen presentation on major histocompatibility complex class I products and peripheral CD8+ T cell tolerance, *J. Exp. Med.*, 196: 1627-38 (2002).

Bonifaz et al., In vivo targeting of antigens to maturing dendritic cells cia the DEC-205 receptor improves T cell vaccination, *J. Exp. Med.*, 199(6): 815-24 (2004).

Branch, A good antisense molecule is hard to find, *TIBS*, 23: 45-50 (1998).

Burgers et al., The challenges of HIV vaccine development and testing, *Best Practice & Research: Clininal Obstetrics & Gynaecology*, 19(1): 277-91 (2005).

Butler et al., A quantitative assay for HIV DNA integration in vivo. *Nat. Med.*, 7: 631-4 (2001).

Case et al., Stable transduction of quiescent CD34+CD38–human hematopoietic cells by HIV-1-based lentiviral vectors, *Proc. Natl. Acad. Sci. USA*, 96(6): 2988-93 (1999).

Chandrashekran et al., Targeted retroviral transduction of c-kit(+) hematopoietic cells using novel ligand display technology, *Blood*, 104: 2697-703 (2004).

Cheng et al., Mechanism of ad5 vaccine immunity and toxicity: Fiber shart targeting of dendritic cells. *PLoS Pathog.*, 3:e25 (2007).

Cheong et al., Improved cellular and humoral immune responses in vivo following targeting of HIV Gag to dendritic cells within human anti-human DEC205 monoclonal antibody. *Blood*, 116: 3828-38 (2010).

Chirila et al., The use of synthetic polymers for delivery of therapeutic antisense oligodeoxynucleotides, *Biomaterials*, 23: 321-42 (2002).

Choi et al., Hybrid HIV/MSCV LTR enhances transgene expression of lentiviral vector in human CD34+hematopoietic cells, *Stem Cells*, 19: 236-46 (2001).

Chou et al., Expression of chimeric monomer and dimer proteins on the plasma membrane of mammalian cells, *Biotechnol. Bioengin.*, 65(2): 160-9 (1999).

Chu et al., Retroviral vector particles displaying the antigen-binding site of an antibody enable cell-type-specific gene transfer, *J. Virol.*, 69(4): 2659-63 (1995).

Cohen, Is an effective HIV vaccine feasible? *Science*, 309: 99 (2005).

Collins et al., Gene therapy meets vaccine development. *TRENDS Biotech.*, 22(12): 623-6 (2004).

Cosset et al., Retroviral retargeting by envelopes expressing an N-terminal binding domain, *J. Virol.*, 69(10): 6314-22 (1995).

Cronin et al., Altering the tropism of lentiviral vectors through pseudotyping. *Curr. Gene Ther.*, 5(4): 387-98 (2005).

Dakappagari et al., Internalizing antibodies to the C-type lectins, L-SIGN and DC-SIGN, inhibit viral glycoprotein binding and deliver antigen to human dendritic cells for the induction of T cell responses. *J. Immunol.*, 176: 426-40 (2006).

De Felipe et al., Skipping the co-expression problem: The new 2A "CHYSEL" technology, *Genet. Vaccines Ther.*,2(13): 1-6 (2004).

De Filipe et al., Targeting of proteins derived from self-processing polyproteins containing multiple signal sequences, *Traffic*, 5: 616-26 (2004).

De Gruijl et al., Prolonged maturation and enhanced transduction of dendritic cells migrated from human skin explants after in situ delivery of CD40-targeted adenoviral. *J. Immunol.*, 169: 5322-533 (2002).

De Ines et al., Apoptosis of a human melanoma cell line specifically induced by membrane-bound single-chain antibodies, *J. Immunol.*, 163: 3948-56 (1999).

Dimitrov et al., Quantitation of human immunodeficiency virus type 1 infection kinetics. *J. Virol.*, 67(4): 2182-90 (1993).

Dimitrov et al., Virus entry: Molecular mechanisms and biomedical applications, *Nat. Rev. Microbiol.*, 2: 109-22 (2004).

Dong et al., HIV-specific cytotoxic T cells from long-term survivors select a unique T cell receptor. *J. Exp. Med.* 200(12): 1547-57 (2004).

Drose et al., Bafilomycins and concanamycins as inhibitors of V-ATPases and P-ATPases, *J. Exp. Biol.*, 200: 1-8 (1997).

Dullaers et al., Induction of effective therapeutic antitumor immunity by direct in vivo administration of lentiviral vectors. *Gene Ther.*, 13: 630-40 (2006).

Engelmayer et al., Vaccinia virus inhibits the maturation of human dendritic cells: A novel mechanism of immune evasion. *J. Immunol.*, 163: 6762-8 (1999).

Esslinger et al., Efficient transduction of dendritic cells and induction of a T-cell response by third-generation lentivectors, *Hum. Gene Ther.*, 13: 1091-100 (2002).

Esslinger et al., In vivo administration of a lentiviral vaccine targets DCs and induces efficient CD8(+) T cell responses. *J. Clin. Invest.*, 111: 1673-81 (2003).

Evans et al., Human cord blood CD34+CD38− cell transduction via lentivirus-based gene transfer ventors, *Hum. Gene Ther.*, 10(9): 1479-89 (1999).

Fielding et al., Inverse targeting of retroviral ventors: Selective gene transfer in a mixed population of hematopoietic and nonhematopoietic cells, *Blood*, 91(5): 1802-9 (1998).

Figdor et al., Dendritic cell immunotherapy: Mapping the way. *Nat. Med.*, 10: 475-80 (2004).

Frolov et al., Translation of Sindbis virus mRNA: analysis of sequences downstream of the iniating AUG codon that enhances translation. *J. Virol.*, 70(2): 1182-90 (1996).

Geijtenbeek et al., DC-SIGN, a dendritic cell-specific HIV-1-binding protein that enhances trans-infection of T cells, *Cell*, 100: 587-97 (2000).

Geijtenbeek et al., Identification of DC-SIGN, a novel dendritic cell-specific ICAM-3 receptor that supports primary immune responses. *Cell*, 100: 575-85 (2000).

Gollan et al., Redirecting retroviral tropism by insertion of short, nondisruptive peptide ligands into envelope, *J. Virol.*, 76(7): 3558-63 (2002).

Gong et al., Induction of antigen-specific antitumor immunity with adenovirus-transduced dendritic cells, *Gene Ther.*, 4: 1023-8 (1997).

Granelli-Piperno et al., Dendritic cells, infected with vesicular stromatitis virus-pseudotyped HIV-1, present viral antigens to CD4+ and CD8+ T cells from HIV-1-infected individuals. *J. Immunol.*, 165: 6620-6 (2000).

Gunning et al., A human beta-actin expression vector system directs high-level accumulation of antisense transcripts, *Proc. Natl. Acad. Sci USA*, 84: 4831-6 (1987).

Gupta et al., Antibody responses against HIV in rhesus macaques following combinations of mucosal and systemic immunizations with chimeric alphavirus-based replicon particles, *AIDS Res., Hum. Retroviruses*, 22(10): 993-7 (2006).

Han et al., Ligand-directed retroviral targeting of human breast cancer cells, *Proc. Natl. Acad. Sci. USA*, 92: 9747-51 (1995).

Hanke et al., Pre-clinical development of a multi-CTL epitope-based DNA prime MVA boost vaccine for AIDS. *Immunol. Lett.*, 66: 177-81 (1999).

Hatziioannou et al., Incorporation of fowl plague virus hemagglutinin in murine leukenia virus particles and analysis of the infectivity of the pseudotyped retroviruses, *J. Virol.*, 72: 5313 (1998).

Iwakuma et al., Self-activating lentiviral ventors with U3 and U5 modifications, *Virology*, 261: 120-32 (1999).

Iwasaki et al., Regulation of adaptive immunity by the innate immune system. *Science*, 327: 291-5 (2010).

Jahn et al., Analysing c-kit internalization using a functional c-kit-EGFP chimera containing the fluorochrome within the extracellular domain, *Oncogene*, 21: 4508-20 (2002).

Jiang et al., Cell-type-specific gene transfer into human cells with retroviral vectors that display single-chain antibodies, *J. Virol.*, 72(12): 10148-56 (1998).

Kahl et al., Human immunodeficiency virus type 1-derived lentivirus vectors pseudotyped with envelope glycoproteins derived from Ross River virus and Semliki Forest virus. *J. Virol.*, 79(3): 1421-30 (2004).

Kahl et al., Lentiviral vectors pseudotyped with glycoproteins from Ross River and vesicular stomatitis viruses: Variable transduction related to cell type and culture conditions. *Molec. Ther.*, 11(3): 470-82 (2005).

Kamrud et al., Analysus of Venezuelan equine encephalitis replicon particles packages in different coats. PLoS ONE, 3(7): e2709 (2008).

Kaplan et al., Induction of antitumor immunity with dendritic cells transduced with adenvirus vector-encoding edogenous tumor-associated antigens, *J. Immunol.*, 163: 699-707 (1999).

Karasuyama et al., Autocrine growth and tumorigenicity of interleukin 2-dependent helper T cells transfected with IL-2 gene, *J. Exp. Med.*, 169: 13-25 (1989).

Keller et al., Overexpression of HOX11 leads to the immortalization of embryonic presursors with both primitive and definitive hematopoietic potential, *Blood*, 92(3): 877-87 (1998).

Kim et al., Induction of therapeutic antitumor immunity by in vivo administration of a lentiviral vaccine. *Hum. Gene Ther.*, 16: 1255-66 (2005).

Kirk et al., Gene-modified dendritic cells for use in tumor vaccines. *Hum. Gene Ther.*, 11: 797-803 (2000).

Kolokoltsov et al., Efficient functional pseudotyping of oncoretroviral and lentiviral vectors by Venezuelan equine encephalitis virus envelope proteins. *J. Virol.*, 79(2): 756-63 (2005).

Korst et al., Active, specific immunotherapy for lung cancer: hurdles and strategies using genetic modification. *Annu. Thor. Surg.*, 76: 1319-26 (2003).

Korth et al., Interferon inhibits the replication of HIV-1, SIV, and SHIV chimeric viruses by distinct mechanisms. *Virology*, 247: 265-73 (1998).

Kung et al., A murine leukimia virus (MuLV) long terminal repeat derived from rhesus macaques in the context of a lentivirus vector and MuLV *gag* sequence results in high-level gene expression in human T lymphocytes, *J. Virol.*, 74(8): 3668-81 (2000).

Kwon et al., Determination of infectious retrovirus concentration from colony-forming assay with quantitative analysis. *J. Virol.*, 77(10): 5712-20 (2003).
Lavillette et al., Retargeting gene delivery using surface-engineered retroviral vetor particles, *Curr. Opin. Biotech.*, 12: 461-6 (2001).
Lee et al., A nonneutralizing anti-HIV-1 antibody turns into a neutralizing antibody when expressed on the surface of HIV-1-susceptible cells: A new way to fight HIV, *J. Immunol.*, 173: 4618-26 (2004).
Liao et al., Design of trangenes for efficient expression of active chimeric proteins on mammalian cells, *Biotechnol. Bioengin.* 73(4): 313-23 (2001).
Lin et al., Receptor-specific targeting mediated by the coexpression of a targeted murine leukemia virus envelope protein and a binding-defective influenza hemagglutinin protein, *Hum. Gene Ther.*, 12(4): 323-32 (2001).
Liu et al., Immune control of an SIV challenge by a T-cell-based vaccine in rhesus monkeys. *Nat. Lett.*, 457: 87-91 (2009).
Lois et al., Germline transmission and tissue-specific expression of trangenes delivered by lentiviral vectors, *Science*, 295(5556): 868-72 (2002).
Lori et al., Cellular immunity and DNA vaccines for the treatment of HIV/AIDS, *Curr. Med. Chem. Anti-Infect. Agents*, 3: 31-41 (2004).
Lorimer et al., Targeting retrovirus to cancer cells expressing a mutant EGF receptor by insertion of a single chain antibody variable domain in the envelope glycoprotein receptor binding lobe, *J. Immunol Meth.*, 237: 147-57 (2000).
Lubong Sabado et al., Directing dendritic cell immunotherapy towards successful cancer treatment. *Immunotherapy*, 2(1): 37-56 (2010).
Lutzko et al., Lentivirus ventors incorporating the immunoglobulin heavy chain enhancer and matrix attachment regions provide position-independent expression in B lymphocytes, *j. Virol.*, 77: 7341-51 (2003).
Mangeot et al., Development of minimal lentivirus vectors derived from simian immunodeficiency virus (SIVmac251) an their use for gene transfer into human dendritic cells, *J. Virol.*, 74: 8307-15 (2000).
Marozsan et al., Relationships between infectious titer, capsid protein levels, and reverse transcriptase activities of diverse human immunodeficiency virus type 1 isolates. *J. Virol.*, 78(20): 11130-41 (2004).
Matano et al., Targeted infection of a retrovirus bearing a CD4-Env chimera into human cells expressing human immunodeficiency virus type 1, *J. Gen. Virol.*, 76: 3165-9 (1995).
Matsuno et al., A life stage of particle-laden rat dendritics in vivo: Their terminal division, active phagocytosis, and translocation from the liver to the draining lymph. *J. Exp. Med.*, 183: 1865-78 (1996).
Maurice et al., Efficient gene transfer into human primary blood lymphocytes by surface-engineered lentiviral vectors that display a T cell-activating polypeptide, *Blood*, 99(7): 2342-50 (2002).
Meissner et al., Development of an inducible pol III transcription system essentially requiring a mutated form of the TATA-binding protein, *Nucl. Acids Res.*, 29(8): 1672-82 (2001).
Meyer zum Buschenfelde et al., Generation of tumor-reactive CTL against the tumor-associated antigen HER2 using retrovirally transduced dendritic cells derived from CD34+ hematopoietic profenitor cells, *J. Immunol.*, 165: 4311-40 (2000).
Narayan et al., Biology and pathogenesis of lentiviruses. *J. Gen. Virol.*, 70: 1617-39 (1989).
Nussenzweig et al., Immune responses: Tails to teach a B cell, *Curr. Biol.*, 7: R355-7 (1997).
Nyberg-Hoffman et al., Sensitivity and reproducibility in adenoviral infectious titer determination. Nat. Med., 3(7): 808-11 (1997).
Palmer et al., Gene therapy for colorectal cancer. *Brit. Med. Bull.*, 64: 201-25 (2002).
Park et al., An essential role for Akt1 in dendritic cell function and tumor immunotherapy, *Nat. Biotechnol.*, 24(12): 1581-90 (2006).
Park et al., Five mouse homologues of the human dendritic cell C-type lectin, DC-SIGN, *Intl. Immunol.*, 13(10): 1283-90 (2001).
Paule et al., Transcription by RNA polymerase I and III, *Nucl. Acids Res.*, 28(6): 1283-98 (2000).
Perri et al., An alphavirus replicon particle chimera derived from venezuelan equine encephalitis and sindbis viruses is a potent gene-based vaccine delivery vector, *J. Virol.*, 77(19): 10394-403 (2003).

Pitisuttithum et al., HIV-1 prophylactic vaccine trials in Thailand. *Curr. HIV Res.*, 3(1): 17-30 (2005).
Powlesland et al., Widely divergent biochemical properties of the complete set of mouse DC-SIGN-related proteins, *J. Biol. Chem.*, 281: 20440-9 (2006).
Racaniello, Are all virus particles infectious? Virology blog, http://www.virology.ws/2011/01/21are-all-virus-particles-infectious/, Jan. 21, 2011.
Ready et al., AIDSVAX flop leaves vaccine field unscathed, *Nat. Med.*, 9(4): 376 (2003).
Ribas et al., Cancer immunotherapy using gene-modified dendritic cells, *Curr. Gene Ther.*, 2: 57-78 (2000).
Rosenberg et al., Cancer immunotherapy moving beyong currect vaccines, *Nat. Med.*, 10: 909-15 (2004).
Rowe et al., Immunication with a lentiviral vector stimulates both CD4 and CD8 T cell responses to an ovalbumin trangene. *Molec. Ther.*, 13(2): 310-9 (2006).
Sanders, No false start for novel pseudotyped vectors. *Curr. Opin. Biotechol.*, 13(5): 437-42 (2002).
Sastry et al., Titering lentiviral vectors: Comparison of DNA, RNA and marker expression methods. Gene Ther., 9: 1155-62 (2002).
Schroers et al., Lentiviral transduction of human dendritic cells, *Meth. Mol. Biol.*, 246: 451-9 (2004).
Schuler et al., The use of dendritic cells in cancer immunotherapy, *Curr. Opin. Immunol.*, 15: 138-47 (2003).
Schwartz et al., Cloning and functional analysis of multiply spliced mRNA species of human immunodeficiency virus type 1, *J. Virol.*, 64(6): 2519-9 (1990).
Shen et al., Silencing of SOCS1 enhances antigen presentation by dendritic cells and antigen-specific anti-tumor immunity. *Nat. Biotechnol.*, 22: 1546-53 (2004).
Shimizu et al., Internalization of kit together with stem cell factor on human fetal liver-derived mast cells: A new protein and RNA synthesis are required for reappearance of kit, *J. Immunol.*, 156: 3443-9 (1996).
Shiu eta l., Identification of ongoing human immunodeficiency virus type 1 (HIV-1) replication in residual viremia during recombinant HIV-1 poxvirus immunications in patients with clinically undetectable viral loads on durable suppressive highly active antiretroviral therapy, *J. Virol.*, 83(19): 9731-42 (2009).
Skehel et al., Receptor binding and membrane fusion in virus entry: The influenza hemagglutinin et al., *Annu. Rev. Biochem.*, 69: 531-69 (2000).
Smit et al., Low-pH-dependent fusion of Sindbis virus with receptor-free cholesterol—an sphingolipid-containing liposomes, *J. Virol.*, 73(10): 8476-84 (1999).
Somia et al., Generation of targeted retroviral vectors by using single-chain variable fragment—An approach to in vivo gene delivery, *Proc. Natl. Acad. Sci. USA*, 92: 7570-4 (1995).
Song et al., Persistent, antigen-specific, therapeutic antitumor immunity by dendritic cells genetically modified with an adenviral vector to express a model tumor antigen, *Gene Ter.*, 7: 2080-6 (2000).
Steinmann et al., Tolerogenic dendritic cells, *Annu. Rev. Immunol.*, 21: 685-711 (2003).
Strauss et al., Host-cell receptors for Sindbis virus. *Arch. Virol.*, 9: 473-84 (1994).
Stricker et al., The maginot line and AIDS vaccines, *Medical Hypotheses*, 48: 527-9 (1997).
Sutton et al., Human immunodeficiency virus type 1 vectors efficiently transduce human hematopoietic stem cells, *J. Virol.*, 72(7): 5781-8 (1998).
Tacken eta l., Dendritic-cell immunotherapy: From ex vivo loading to in vivo targeting, *Nat. Rev. Immunol.*, 7: 790-802 (2007).
Takadera et al., Structure of the two promoters of the human *Ick* gene: Differential accumulation of two classes of *Ick* transcripts in T cells, *Mol. Cell. Biol.*, 9(5): 2173-80 (1989).
Takahara et al., Functional comparison of the mouse DC-SIGN, SIGNR1, SIGNR3 and Langerin, C-type lectins, *Int. Immunol.*, 16: 819-29 (2004).
Tang et al., Molecular links between the E2 envelope glycoprotein and nucleocapsid core in Sindbis virus. *J. Molec. Biol.*, 414: 442-59 (2011).

Tatsis et al., Adenoviruses as vaccine vectors, *Mol. Ther.*, 10: 616-29 (2004).

Temme et al., Efficient transduction and long-term retroviral expression of the melanoma-associated tumor antigen tyrosinase in CD34(+) cord blood-derived dendritic cells, *Gene Ther.*, 9: 1551-50 (2002).

Trumpfheller et al., Intensified and protective CD4+ T cell immunity in mice with anti-dendritic cell HIV gag fusion antibody vaccine. *J. Exp. Med.*, 1-11 (2006).

Uchida et al., HIV, but not murine leukemia virus, vectors mediate high efficiency gene transfer into freshly isolated G0/G1 human hematopoietic stem cells, *Proc. Natl Acad. Sci. USA*, 95(20): 11939-44 (1998).

Valsesia-Wittmann et al., Modifications in the binding domain of avian retrovirus envelope protein to redirect the host range of retroviral vectors, *J. Virol.*, 68(7): 4609-19 (1994).

Veljkovic et al., AIDS epidemic at the beginning of the third millennium: Time for a new AIDS vaccine strategy, *Vaccine*, 19: 1855-62 (2001).

Verhoeyen et al., Surface-engineering of lentiviral vectors. *J. Gene Med.*, 6: S83-94 (2004).

Verma et al., Gene therapy—promises, problems and prospects, *Nature*, 389(6648): 239-42 (1997).

Waite et al., Inhibition of Sindbis virus release by media of low ionic strength: an electron microscope study. *J. Virol.*, 10(3): 537-44 (1972).

Wang et al., High-affinity laminin receptor is a receptor of Sindbis virus in mammalian cells, *J. Virol.*, 66: 4992-5001 (1992).

Weber et al., Phase I clinical trial with HIV-1 gp160 plasmid vaccine in HIV-1-infected asymptomatic subjects. *Eur. J. Clin. Microbiol. Infect. Dis.*, 20: 800-3 (2001).

Wigler et al., DNA-mediated transfer of the adenine phosphoribosyltransferase locus into mammalian cells, *Proc. Natl. Acad. Sci. USA*, 76(3): 1373-6 (1979).

Williamsburg BioProcessing Foundation, Reference Materials for Retroviruses and Lentiviruses—Final Report, pp. 1-13, Jun. 5, 2002.

Wu et al., Enhanced breadth of CD4 T-cell immunity by DNA prime adenovirus boost immunication to human immunodeficiency virus Env and Gag immunogens. *J. Virol.*, 79(13): 8024-31 (2005).

Yang et al., Long-term in vivo provision of antigen-specific T cell immunity by programming hematopoietic stem cells, *Proc. Natl. Acad. Sci. USA*, 102: 4518-23 (2005).

Yee et al., The regulation of myogenin gene expression during the embryonic development of the mouse, *Genes Dev.*, 7: 1277-89 (1993).

You et al., Targeting dendritic cells to enhance DNA vaccine potency, *Cancer Res.*, 61: 3704-11 (2001).

Zhai et al., Antigen-specific tumor vaccines, *J. Immunol.*, 156(2): 700-10 (1996).

Zhou et al., Current methods for loading dendritic cells with tumor antigen for the induction of antitumor immunity. *J. Immunol.* 25(4): 289-303 (2002).

Zhou et al., DC-SIGN and immunoregulation. *Cell Mol. Immunoo.*, 3: 279-83 (2006).

Zimmerman et al., Identification of a host protein essential for assembly of immature HIV-1 capsids, *Lett. Nat.*, 415: 88-92 (2002).

Zufferey et al., Woodchuck hepatitis cirus posttranscriptional regulatory element enhances expression of trangenes delievered by retroviral vectors, *J. Virol.*, 74(4): 2886-92 (1999).

* cited by examiner

FIGURE 5B

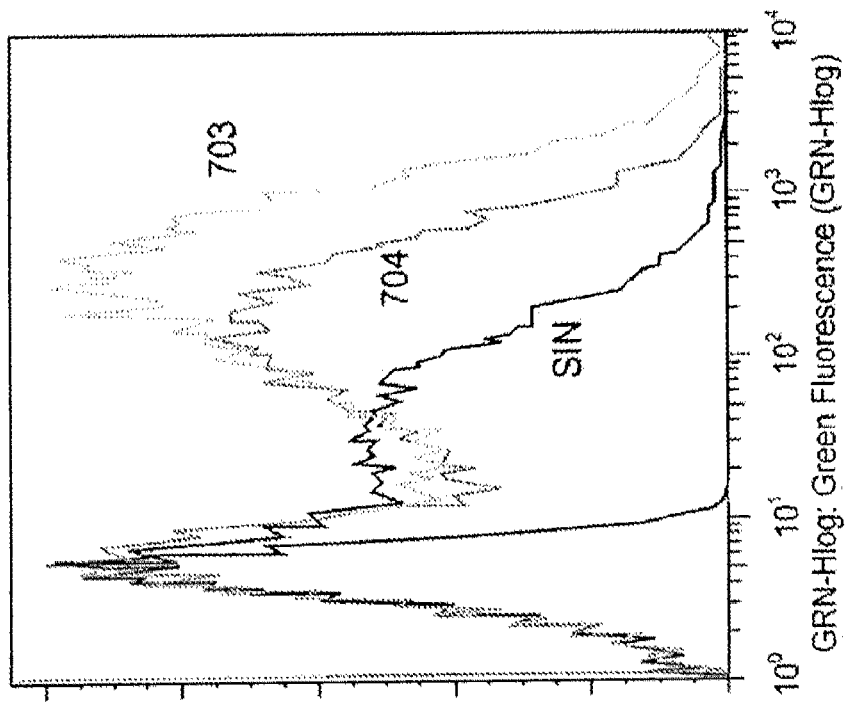
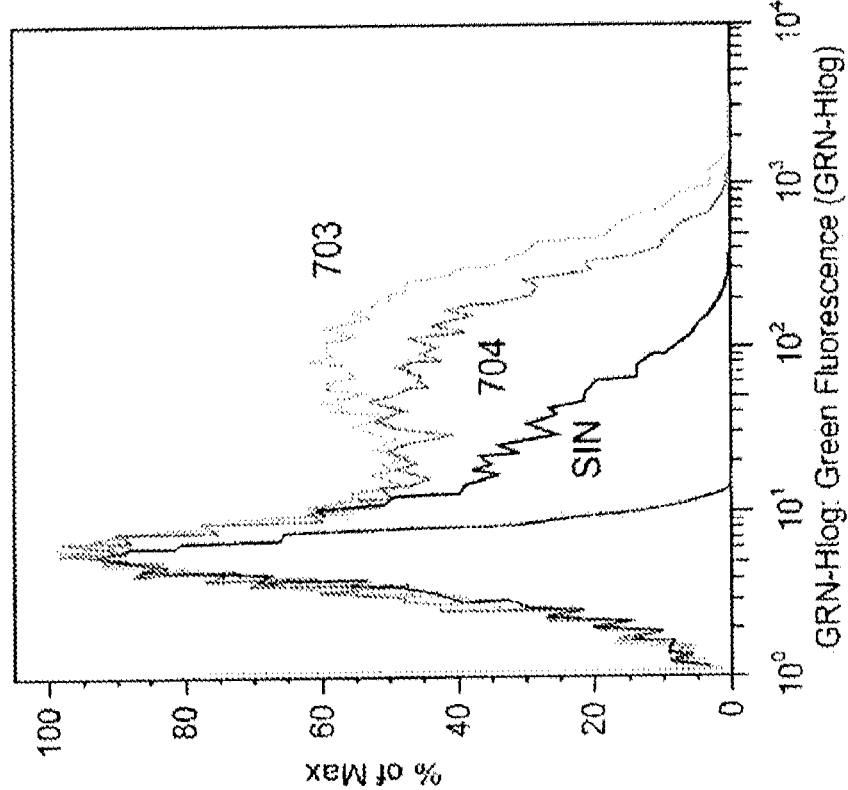

SEQUENCE LISTING

```
<160> NUMBER OF SEQ ID NOS: 29

<210> SEQ ID NO 1
<211> LENGTH: 423
<212> TYPE: PRT
<213> ORGANISM: Sindbis virus
<220> FEATURE:
<221> NAME/KEY: misc_feature
<222> LOCATION: (160)..(160)
<223> OTHER INFORMATION: Xaa can be any naturally occurring amino acid

<400> SEQUENCE: 1
```

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ala Asn Lys Tyr
    50                  55                  60

Arg Tyr Met Ser Leu Lys Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
        115                 120                 125

Lys Ile Lys Pro Lys Phe Val Gly Arg Glu Lys Tyr Asp Leu Pro Pro
    130                 135                 140

Val His Gly Lys Lys Ile Pro Cys Thr Val Tyr Asp Arg Leu Lys Xaa
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
    210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

-continued

```
Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285

Thr Asp His Leu Thr Leu Leu Thr Arg Arg Leu Gly Ala Asn Pro
    290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
        355                 360                 365

Leu Ala Val Ala Ser Ala Thr Val Ala Met Met Ile Gly Val Thr Val
    370                 375                 380

Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 2
<211> LENGTH: 986
<212> TYPE: PRT
<213> ORGANISM: Sindbis virus

<400> SEQUENCE: 2

Met Ser Ala Ala Pro Leu Val Thr Ala Met Cys Leu Leu Gly Asn Val
1

```
Tyr Asp Leu Pro Pro Val His Gly Lys Lys Ile Pro Cys Thr Val Tyr
    210                 215                 220
Asp Arg Leu Ala Ala Thr Thr Ala Gly Tyr Ile Thr Met His Arg Pro
225                 230                 235                 240
Arg Pro His Ala Tyr Thr Ser Tyr Leu Glu Glu Ser Ser Gly Lys Val
                245                 250                 255
Tyr Ala Lys Pro Pro Ser Gly Lys Asn Ile Thr Tyr Glu Cys Lys Cys
                260                 265                 270
Gly Asp Tyr Lys Thr Gly Thr Val Ser Thr Arg Thr Glu Ile Thr Gly
                275                 280                 285
Cys Thr Ala Ile Lys Gln Cys Val Ala Tyr Lys Ser Asp Gln Thr Lys
290                 295                 300
Trp Val Phe Asn Ser Pro Asp Leu Ile Arg His Asp Asp His Thr Ala
305                 310                 315                 320
Gln Gly Lys Leu His Leu Pro Phe Lys Leu Ile Pro Ser Thr Cys Met
                325                 330                 335
Val Pro Val Ala His Ala Pro Asn Val Ile His Gly Phe Lys His Ile
                340                 345                 350
Ser Leu Gln Leu Asp Thr Asp His Leu Thr Leu Leu Thr Thr Arg Arg
                355                 360                 365
Leu Gly Ala Asn Pro Glu Pro Thr Thr Glu Trp Ile Val Gly Lys Thr
370                 375                 380
Val Arg Asn Phe Thr Val Asp Arg Asp Gly Leu Glu Tyr Ile Trp Gly
385                 390                 395                 400
Asn His Glu Pro Val Arg Val Tyr Ala Gln Glu Ser Ala Pro Gly Asp
                405                 410                 415
Pro His Gly Trp Pro His Glu Ile Val Gln His Tyr Tyr His Arg His
                420                 425                 430
Pro Val Tyr Thr Ile Leu Ala Val Ala Ser Ala Thr Val Ala Met Met
                435                 440                 445
Ile Gly Val Thr Val Ala Val Leu Cys Ala Cys Lys Ala Arg Arg Glu
450                 455                 460
Cys Leu Thr Pro Tyr Ala Leu Ala Pro Asn Ala Val Ile Pro Thr Ser
465                 470                 475                 480
Leu Ala Leu Leu Cys Cys Val Arg Ser Ala Asn Ala Glu Thr Phe Thr
                485                 490                 495
Glu Thr Met Ser Tyr Leu Trp Ser Asn Ser Gln Pro Phe Phe Trp Val
                500                 505                 510
Gln Leu Cys Ile Pro Leu Ala Ala Phe Ile Val Leu Met Arg Cys Cys
                515                 520                 525
Ser Cys Cys Leu Pro Phe Leu Val Val Ala Gly Ala Tyr Leu Ala Lys
                530                 535                 540
Val Asp Ala Tyr Glu His Ala Thr Thr Val Pro Asn Val Pro Gln Ile
545                 550                 555                 560
Pro Tyr Lys Ala Leu Val Glu Arg Ala Gly Tyr Ala Pro Leu Asn Leu
                565                 570                 575
Glu Ile Thr Val Met Ser Ser Glu Val Leu Pro Ser Thr Asn Gln Glu
                580                 585                 590
Tyr Ile Thr Cys Lys Phe Thr Thr Val Val Pro Ser Pro Lys Ile Lys
                595                 600                 605
Cys Cys Gly Ser Leu Glu Cys Gln Pro Ala Ala His Ala Gly Tyr Thr
610                 615                 620
Cys Lys Val Phe Gly Gly Val Tyr Pro Phe Met Trp Gly Gly Ala Gln
```

```
                625                 630                 635                 640
Cys Phe Cys Asp Ser Glu Asn Ser Gln Met Ser Glu Ala Tyr Val Glu
                    645                 650                 655

Leu Ser Ala Asp Cys Ala Ser Asp His Ala Gln Ala Ile Lys Val His
            660                 665                 670

Thr Ala Ala Met Lys Val Gly Leu Arg Ile Val Tyr Gly Asn Thr Thr
        675                 680                 685

Ser Phe Leu Asp Val Tyr Val Asn Gly Val Thr Pro Gly Thr Ser Lys
    690                 695                 700

Asp Leu Lys Val Ile Ala Gly Pro Ile Ser Ala Ser Phe Thr Pro Phe
705                 710                 715                 720

Asp His Lys Val Val Ile His Arg Gly Leu Val Tyr Asn Tyr Asp Phe
                725                 730                 735

Pro Glu Tyr Gly Ala Met Lys Pro Gly Ala Phe Gly Asp Ile Gln Ala
            740                 745                 750

Thr Ser Leu Thr Ser Lys Asp Leu Ile Ala Ser Thr Asp Ile Arg Leu
        755                 760                 765

Leu Lys Pro Ser Ala Lys Asn Val His Val Pro Tyr Thr Gln Ala Ser
    770                 775                 780

Ser Gly Phe Glu Met Trp Lys Asn Asn Ser Gly Arg Pro Leu Gln Glu
785                 790                 795                 800

Thr Ala Pro Phe Gly Cys Lys Ile Ala Val Asn Pro Leu Arg Ala Val
                805                 810                 815

Asp Cys Ser Tyr Gly Asn Ile Pro Ile Ser Ile Asp Ile Pro Asn Ala
            820                 825                 830

Ala Phe Ile Arg Thr Ser Asp Ala Pro Leu Val Ser Thr Val Lys Cys
        835                 840                 845

Glu Val Ser Glu Cys Thr Tyr Ser Ala Asp Phe Gly Gly Met Ala Thr
    850                 855                 860

Leu Gln Tyr Val Ser Asp Arg Glu Gly Gln Cys Pro Val His Ser His
865                 870                 875                 880

Ser Ser Thr Ala Thr Leu Gln Glu Ser Thr Val His Val Leu Glu Lys
                885                 890                 895

Gly Ala Val Thr Val His Phe Ser Thr Ala Ser Pro Gln Ala Asn Phe
            900                 905                 910

Ile Val Ser Leu Cys Gly Lys Lys Thr Thr Cys Asn Ala Glu Cys Lys
        915                 920                 925

Pro Pro Ala Asp His Ile Val Ser Thr Pro His Lys Asn Asp Gln Glu
    930                 935                 940

Phe Gln Ala Ala Ile Ser Lys Thr Ser Trp Ser Trp Leu Phe Ala Leu
945                 950                 955                 960

Phe Gly Gly Ala Ser Ser Leu Leu Ile Ile Gly Leu Met Ile Phe Ala
                965                 970                 975

Cys Ser Met Met Leu Thr Ser Thr Arg Arg
            980                 985

<210> SEQ ID NO 3
<211> LENGTH: 982
<212> TYPE: PRT
<213> ORGANISM: Sindbis virus

<400> SEQUENCE: 3

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
```

```
                        20                  25                  30
Arg Ala Leu Asp Ile Leu Glu Glu Asn Val Asn His Glu Ala Tyr Asp
                35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Lys Glu Gly Thr
        130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445
```

```
Val Ala Val Leu Cys Ala Cys Lys Ala Arg Arg Glu Cys Leu Thr Pro
        450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525

Pro Phe Leu Val Val Ala Gly Ala Tyr Leu Ala Lys Val Asp Ala Tyr
        530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
    770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880
```

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
                900                 905                 910

Cys Gly Lys Lys Thr Thr Cys Asn Ala Glu Cys Lys Pro Pro Ala Asp
                915                 920                 925

His Ile Val Ser Thr Pro His Lys Asn Asp Gln Glu Phe Gln Ala Ala
                930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
                980

<210> SEQ ID NO 4
<211> LENGTH: 982
<212> TYPE: PRT
<213> ORGANISM: Sindbis virus

<400> SEQUENCE: 4

Met Ser Ala Ala Pro Leu Val Thr Ala Met Cys Leu Leu Gly Asn Val
1 5 10 15

Ser Phe Pro Cys Asp Arg Pro Pro Thr Cys Tyr Thr Arg Glu Pro Ser
20 25 30

Arg Ala Leu Asp Ile Leu Glu Glu Asn Val Asn His Glu Ala Tyr Asp
35 40 45

Thr Leu Leu Asn Ala Ile Leu Arg Cys Gly Ser Ser Gly Arg Ser Lys
50 55 60

Arg Ser Val Ile Asp Asp Phe Thr Leu Thr Ser Pro Tyr Leu Gly Thr
65 70 75 80

Cys Ser Tyr Cys His His Thr Val Pro Cys Phe Ser Pro Val Lys Ile
85 90 95

Glu Gln Val Trp Asp Glu Ala Asp Asp Asn Thr Ile Arg Ile Gln Thr
100 105 110

Ser Ala Gln Phe Gly Tyr Asp Gln Ser Gly Ala Ala Ser Ala Asn Lys
115 120 125

Tyr Arg Tyr Met Ser Leu Glu Gln Asp His Thr Val Glu Glu Gly Thr
130 135 140

Met Asp Asp Ile Lys Ile Ser Thr Ser Gly Pro Cys Arg Arg Leu Ser
145 150 155 160

Tyr Lys Gly Tyr Phe Leu Leu Ala Lys Cys Pro Pro Gly Asp Ser Val
165 170 175

Thr Val Ser Ile Val Ser Ser Asn Ser Ala Thr Ser Cys Thr Leu Ala
180 185 190

Arg Lys Ile Lys Pro Lys Phe Val Gly Arg Glu Lys Tyr Asp Leu Pro
195 200 205

Pro Val His Gly Lys Lys Ile Pro Cys Thr Val Tyr Asp Arg Leu Glu
210 215 220

Gly Thr Thr Ala Gly Tyr Ile Thr Met His Arg Pro Arg Pro His Ala
225 230 235 240

Tyr Thr Ser Tyr Leu Glu Glu Ser Ser Gly Lys Val Tyr Ala Lys Pro
245 250 255

Pro Ser Gly Lys Asn Ile Thr Tyr Glu Cys Lys Cys Gly Asp Tyr Lys
260 265 270

```
Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
    450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
            500                 505                 510

Pro Leu Ala Ala Phe Ile Val Leu Met Arg Cys Cys Ser Cys Cys Leu
        515                 520                 525

Pro Phe Leu Val Val Ala Gly Ala Tyr Leu Ala Lys Val Asp Ala Tyr
    530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
```

-continued

```
            690                 695                 700
Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
                740                 745                 750

Ser Lys Asp Leu Ile Ala Ser Thr Asp Ile Arg Leu Leu Lys Pro Ser
                755                 760                 765

Ala Lys Asn Val His Val Pro Tyr Thr Gln Ala Ser Ser Gly Phe Glu
                770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                    805                 810                 815

Gly Asn Ile Pro Ile Ser Ile Asp Ile Pro Asn Ala Ala Phe Ile Arg
                820                  825                830

Thr Ser Asp Ala Pro Leu Val Ser Thr Val Lys Cys Glu Val Ser Glu
                835                 840                 845

Cys Thr Tyr Ser Ala Asp Phe Gly Gly Met Ala Thr Leu Gln Tyr Val
850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
                900                 905                 910

Cys Gly Lys Lys Thr Thr Cys Asn Ala Glu Cys Lys Pro Pro Ala Asp
                915                 920                 925

His Ile Val Ser Thr Pro His Lys Asn Asp Gln Glu Phe Gln Ala Ala
                930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 5
<211> LENGTH: 980
<212> TYPE: PRT
<213> ORGANISM: Sindbis virus

<400> SEQUENCE: 5

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
            50                  55                  60

Arg Ser Val Ile Asp Asp Phe Thr Leu Thr Ser Pro Tyr Leu Gly Thr
65              70                  75                  80

Cys Ser Tyr Cys His His Thr Val Pro Cys Phe Ser Pro Val Lys Ile
```

```
                    85                  90                  95
Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Lys Glu Gly Thr
        130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Thr
210                 215                 220

Thr Ala Gly Tyr Ile Thr Met His Arg Pro Arg Pro His Ala Tyr Thr
225                 230                 235                 240

Ser Tyr Leu Glu Glu Ser Ser Gly Lys Val Tyr Ala Lys Pro Pro Ser
                245                 250                 255

Gly Lys Asn Ile Thr Tyr Glu Cys Lys Cys Gly Asp Tyr Lys Thr Gly
            260                 265                 270

Thr Val Ser Thr Arg Thr Glu Ile Thr Gly Cys Thr Ala Ile Lys Gln
        275                 280                 285

Cys Val Ala Tyr Lys Ser Asp Gln Thr Lys Trp Val Phe Asn Ser Pro
290                 295                 300

Asp Leu Ile Arg His Asp Asp His Thr Ala Gln Gly Lys Leu His Leu
305                 310                 315                 320

Pro Phe Lys Leu Ile Pro Ser Thr Cys Met Val Pro Val Ala His Ala
                325                 330                 335

Pro Asn Val Ile His Gly Phe Lys His Ile Ser Leu Gln Leu Asp Thr
            340                 345                 350

Asp His Leu Thr Leu Leu Thr Thr Arg Arg Leu Gly Ala Asn Pro Glu
        355                 360                 365

Pro Thr Thr Glu Trp Ile Val Gly Lys Thr Val Arg Asn Phe Thr Val
370                 375                 380

Asp Arg Asp Gly Leu Glu Tyr Ile Trp Gly Asn His Glu Pro Val Arg
385                 390                 395                 400

Val Tyr Ala Gln Glu Ser Ala Pro Gly Asp Pro His Gly Trp Pro His
                405                 410                 415

Glu Ile Val Gln His Tyr Tyr His Arg His Pro Val Tyr Thr Ile Leu
            420                 425                 430

Ala Val Ala Ser Ala Thr Val Ala Met Met Ile Gly Val Thr Val Ala
        435                 440                 445

Val Leu Cys Ala Cys Lys Ala Arg Arg Glu Cys Leu Thr Pro Tyr Ala
450                 455                 460

Leu Ala Pro Asn Ala Val Ile Pro Thr Ser Leu Ala Leu Leu Cys Cys
465                 470                 475                 480

Val Arg Ser Ala Asn Ala Glu Thr Phe Thr Glu Thr Met Ser Tyr Leu
                485                 490                 495

Trp Ser Asn Ser Gln Pro Phe Phe Trp Val Gln Leu Cys Ile Pro Leu
            500                 505                 510
```

```
Ala Ala Phe Ile Val Leu Met Arg Cys Cys Ser Cys Cys Leu Pro Phe
        515                 520                 525

Leu Val Val Ala Gly Ala Tyr Leu Ala Lys Val Asp Ala Tyr Glu His
530                 535                 540

Ala Thr Thr Val Pro Asn Val Pro Gln Ile Pro Tyr Lys Ala Leu Val
545                 550                 555                 560

Glu Arg Ala Gly Tyr Ala Pro Leu Asn Leu Glu Ile Thr Val Met Ser
                565                 570                 575

Ser Glu Val Leu Pro Ser Thr Asn Gln Glu Tyr Ile Thr Cys Lys Phe
            580                 585                 590

Thr Thr Val Val Pro Ser Pro Lys Ile Lys Cys Cys Gly Ser Leu Glu
        595                 600                 605

Cys Gln Pro Ala Ala His Ala Asp Tyr Thr Cys Lys Val Phe Gly Gly
    610                 615                 620

Val Tyr Pro Phe Met Trp Gly Ala Gln Cys Phe Cys Asp Ser Glu
625                 630                 635                 640

Asn Ser Gln Met Ser Glu Ala Tyr Val Glu Leu Ser Ala Asp Cys Ala
                645                 650                 655

Ser Asp His Ala Gln Ala Ile Lys Val His Thr Ala Ala Met Lys Val
            660                 665                 670

Gly Leu Arg Ile Val Tyr Gly Asn Thr Thr Ser Phe Leu Asp Val Tyr
        675                 680                 685

Val Asn Gly Val Thr Pro Gly Thr Ser Lys Asp Leu Lys Val Ile Ala
    690                 695                 700

Gly Pro Ile Ser Ala Ser Phe Thr Pro Phe Asp His Lys Val Val Ile
705                 710                 715                 720

His Arg Gly Leu Val Tyr Asn Tyr Asp Phe Pro Glu Tyr Gly Ala Met
                725                 730                 735

Lys Pro Gly Ala Phe Gly Asp Ile Gln Ala Thr Ser Leu Thr Ser Lys
            740                 745                 750

Asp Leu Ile Ala Ser Thr Asp Ile Arg Leu Leu Lys Pro Ser Ala Lys
        755                 760                 765

Asn Val His Val Pro Tyr Thr Gln Ala Ser Ser Gly Phe Glu Met Trp
    770                 775                 780

Lys Asn Asn Ser Gly Arg Pro Leu Gln Glu Thr Ala Pro Phe Gly Cys
785                 790                 795                 800

Lys Ile Ala Val Asn Pro Leu Arg Ala Val Asp Cys Ser Tyr Gly Asn
                805                 810                 815

Ile Pro Ile Ser Ile Asp Ile Pro Asn Ala Ala Phe Ile Arg Thr Ser
            820                 825                 830

Asp Ala Pro Leu Val Ser Thr Val Lys Cys Glu Val Ser Glu Cys Thr
        835                 840                 845

Tyr Ser Ala Asp Phe Gly Gly Met Ala Thr Leu Gln Tyr Val Ser Asp
    850                 855                 860

Arg Glu Gly Gln Cys Pro Val His Ser His Ser Ser Thr Ala Thr Leu
865                 870                 875                 880

Gln Glu Ser Thr Val His Val Leu Glu Lys Gly Ala Val Thr Val His
                885                 890                 895

Phe Ser Thr Ala Ser Pro Gln Ala Asn Phe Ile Val Ser Leu Cys Gly
            900                 905                 910

Lys Lys Thr Thr Cys Asn Ala Glu Cys Lys Pro Pro Ala Asp His Ile
        915                 920                 925

Val Ser Thr Pro His Lys Asn Asp Gln Glu Phe Gln Ala Ala Ile Ser
    930                 935                 940
```

```
Lys Thr Ser Trp Ser Trp Leu Phe Ala Leu Phe Gly Gly Ala Ser Ser
945                 950                 955                 960

Leu Leu Ile Ile Gly Leu Met Ile Phe Ala Cys Ser Met Met Leu Thr
            965                 970                 975

Ser Thr Arg Arg
            980

<210> SEQ ID NO 6
<211> LENGTH: 981
<212> TYPE: PRT
<213> ORGANISM: Sindbis virus

<400> SEQUENCE: 6

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Glu Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335
```

```
Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
            355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
            405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
            435                 440                 445

Ala Val Leu Cys Ala Cys Lys Ala Arg Arg Glu Cys Leu Thr Pro Tyr
            450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
            515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
            595                 600                 605

Glu Cys Gln Pro Ala Ala His Ala Asp Tyr Thr Cys Lys Val Phe Gly
610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
            675                 680                 685

Tyr Val Asn Gly Val Thr Pro Gly Thr Ser Lys Asp Leu Lys Val Ile
690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
```

```
                755                 760                 765
Lys Asn Val His Val Pro Tyr Thr Gln Ala Ser Ser Gly Phe Glu Met
    770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
                820                 825                 830

Ser Asp Ala Pro Leu Val Ser Thr Val Lys Cys Glu Val Ser Glu Cys
                835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
                900                 905                 910

Gly Lys Lys Thr Thr Cys Asn Ala Glu Cys Lys Pro Pro Ala Asp His
                915                 920                 925

Ile Val Ser Thr Pro His Lys Asn Asp Gln Glu Phe Gln Ala Ala Ile
                930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
                980

<210> SEQ ID NO 7
<211> LENGTH: 982
<212> TYPE: PRT
<213> ORGANISM: Sindbis virus

<400> SEQUENCE: 7

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
                35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
                115                 120                 125

Tyr Arg Tyr Met Ser Leu Lys Gln Asp His Thr Val Lys Glu Gly Thr
    130                 135                 140

Met Asp Asp Ile Lys Ile Ser Thr Ser Gly Pro Cys Arg Arg Leu Ser
```

-continued

```
            145                 150                 155                 160
Tyr Lys Gly Tyr Phe Leu Leu Ala Lys Cys Pro Pro Gly Asp Ser Val
                    165                 170                 175
Thr Val Ser Ile Val Ser Ser Asn Ser Ala Thr Ser Cys Thr Leu Ala
                    180                 185                 190
Arg Lys Ile Lys Pro Lys Phe Val Gly Arg Glu Lys Tyr Asp Leu Pro
                    195                 200                 205
Pro Val His Gly Lys Lys Ile Pro Cys Thr Val Tyr Asp Arg Leu Glu
                    210                 215                 220
Gly Thr Thr Ala Gly Tyr Ile Thr Met His Arg Pro Arg Pro His Ala
225                 230                 235                 240
Tyr Thr Ser Tyr Leu Glu Glu Ser Ser Gly Lys Val Tyr Ala Lys Pro
                    245                 250                 255
Pro Ser Gly Lys Asn Ile Thr Tyr Glu Cys Lys Cys Gly Asp Tyr Lys
                    260                 265                 270
Thr Gly Thr Val Ser Thr Arg Thr Glu Ile Thr Gly Cys Thr Ala Ile
                    275                 280                 285
Lys Gln Cys Val Ala Tyr Lys Ser Asp Gln Thr Lys Trp Val Phe Asn
290                 295                 300
Ser Pro Asp Leu Ile Arg His Asp Asp His Thr Ala Gln Gly Lys Leu
305                 310                 315                 320
His Leu Pro Phe Lys Leu Ile Pro Ser Thr Cys Met Val Pro Val Ala
                    325                 330                 335
His Ala Pro Asn Val Ile His Gly Phe Lys His Ile Ser Leu Gln Leu
                    340                 345                 350
Asp Thr Asp His Leu Thr Leu Leu Thr Thr Arg Arg Leu Gly Ala Asn
                    355                 360                 365
Pro Glu Pro Thr Thr Glu Trp Ile Val Gly Lys Thr Val Arg Asn Phe
                    370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                    405                 410                 415
Pro His Glu Ile Val Gln His Tyr Tyr His Arg His Pro Val Tyr Thr
                    420                 425                 430
Ile Leu Ala Val Ala Ser Ala Thr Val Ala Met Met Ile Gly Val Thr
                    435                 440                 445
Val Ala Val Leu Cys Ala Cys Lys Ala Arg Arg Glu Cys Leu Thr Pro
                    450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                    485                 490                 495
Tyr Leu Trp Ser Asn Ser Gln Pro Phe Phe Trp Val Gln Leu Cys Ile
                    500                 505                 510
Pro Leu Ala Ala Phe Ile Val Leu Met Arg Cys Cys Ser Cys Cys Leu
                    515                 520                 525
Pro Phe Leu Val Val Ala Gly Ala Tyr Leu Ala Lys Val Asp Ala Tyr
                    530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                    565                 570                 575
```

```
Met Ser Ser Glu Val Leu Pro Ser Thr Asn Gln Glu Tyr Ile Thr Cys
            580                 585                 590

Lys Phe Thr Thr Val Val Pro Ser Pro Lys Ile Lys Cys Cys Gly Ser
        595                 600                 605

Leu Glu Cys Gln Pro Ala Ala His Ala Asp Tyr Thr Cys Lys Val Phe
    610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
            660                 665                 670

Lys Val Gly Leu Arg Ile Val Tyr Gly Asn Thr Thr Ser Phe Leu Asp
        675                 680                 685

Val Tyr Val Asn Gly Val Thr Pro Gly Thr Ser Lys Asp Leu Lys Val
    690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
    770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
    850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
    930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980
```

<210> SEQ ID NO 8

-continued

```
<211> LENGTH: 981
<212> TYPE: PRT
<213> ORGANISM: Sindbis

```
Arg Val Tyr Ala Gln Glu Ser Ala Pro Gly Asp Pro His Gly Trp Pro
                405                 410                 415

His Glu Ile Val Gln His Tyr His Arg His Pro Val Tyr Thr Ile
            420                 425                 430

Leu Ala Val Ala Ser Ala Thr Val Ala Met Met Ile Gly Val Thr Val
                435                 440                 445

Ala Val Leu Cys Ala Cys Lys Ala Arg Arg Glu Cys Leu Thr Pro Tyr
465                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
                500                 505                 510

Leu Ala Ala Phe Ile Val Leu Met Arg Cys Cys Ser Cys Cys Leu Pro
                515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
                580                 585                 590

Phe Thr Thr Val Val Pro Ser Pro Lys Ile Lys Cys Cys Gly Ser Leu
                595                 600                 605

Glu Cys Gln Pro Ala Ala His Ala Asp Tyr Thr Cys Lys Val Phe Gly
                610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
                660                 665                 670

Val Gly Leu Arg Ile Val Tyr Gly Asn Thr Thr Ser Phe Leu Asp Val
                675                 680                 685

Tyr Val Asn Gly Val Thr Pro Gly Thr Ser Lys Asp Leu Lys Val Ile
                690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
                740                 745                 750

Lys Asp Leu Ile Ala Ser Thr Asp Ile Arg Leu Leu Lys Pro Ser Ala
                755                 760                 765

Lys Asn Val His Val Pro Tyr Thr Gln Ala Ser Ser Gly Phe Glu Met
                770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
```

```
                        820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
    930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 9
<211> LENGTH: 982
<212> TYPE: PRT
<213> ORGANISM: Sindbis virus

<400> SEQUENCE: 9

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Lys Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
```

-continued

```
            210                 215                 220
Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
                260                 265                 270

Thr Gly Thr Val Ser Thr Arg Thr Glu Ile Thr Gly Cys Thr Ala Ile
                275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
                340                 345                 350

Asp Thr Asp His Leu Thr Leu Leu Thr Thr Arg Arg Leu Gly Ala Asn
                355                 360                 365

Pro Glu Pro Thr Thr Glu Trp Ile Val Gly Lys Thr Val Arg Asn Phe
370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
                420                 425                 430

Ile Leu Ala Val Ala Ser Ala Thr Val Ala Met Met Ile Gly Val Thr
                435                 440                 445

Val Ala Val Leu Cys Ala Cys Lys Ala Arg Arg Glu Cys Leu Thr Pro
450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala Glu Thr Phe Thr Glu Thr Met Ser
                485                 490                 495

Tyr Leu Trp Ser Asn Ser Gln Pro Phe Phe Trp Val Gln Leu Cys Ile
                500                 505                 510

Pro Leu Ala Ala Phe Ile Val Leu Met Arg Cys Cys Ser Cys Cys Leu
                515                 520                 525

Pro Phe Leu Val Val Ala Gly Ala Tyr Leu Ala Lys Val Asp Ala Tyr
                530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
                580                 585                 590

Lys Phe Thr Thr Val Val Pro Ser Pro Lys Ile Lys Cys Cys Gly Ser
                595                 600                 605

Leu Glu Cys Gln Pro Ala Ala His Ala Asp Tyr Thr Cys Lys Val Phe
                610                 615                 620

Gly Gly Val Tyr Pro Phe Met Trp Gly Gly Ala Gln Cys Phe Cys Asp
625                 630                 635                 640
```

```
Ser Glu Asn Ser Gln Met Ser Glu Ala Tyr Val Glu Leu Ser Ala Asp
                645                 650                 655

Cys Ala Ser Asp His Ala Gln Ala Ile Lys Val His Thr Ala Ala Met
        660                 665                 670

Lys Val Gly Leu Arg Ile Val Tyr Gly Asn Thr Thr Ser Phe Leu Asp
            675                 680                 685

Val Tyr Val Asn Gly Val Thr Pro Gly Thr Ser Lys Asp Leu Lys Val
        690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
            725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
        755                 760                 765

Ala Lys Asn Val His Val Pro Tyr Thr Gln Ala Ser Ser Gly Phe Glu
        770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
            805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
        850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
            885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
        915                 920                 925

His Ile Val Ser Thr Pro His Lys Asn Asp Gln Glu Phe Gln Ala Ala
        930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975

Leu Thr Ser Thr Arg Arg
            980

<210> SEQ ID NO 10
<211> LENGTH: 981
<212> TYPE: PRT
<213> ORGANISM: Sindbis virus

<400> SEQUENCE: 10

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30
```

-continued

```
Arg Ala Leu Asp Ile Leu Glu Glu Asn Val Asn His Glu Ala Tyr Asp
         35                  40                  45

Thr Leu Leu Asn Ala Ile Leu Arg Cys Gly Ser Ser Gly Arg Ser Lys
 50                  55                  60

Arg Ser Val Ile Asp Asp Phe Thr Leu Thr Ser Pro Tyr Leu Gly Thr
 65                  70                  75                  80

Cys Ser Tyr Cys His His Thr Val Pro Cys Phe Ser Pro Val Lys Ile
                 85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Lys Gln Asp His Thr Val Glu Glu Gly Thr
130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Glu
210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
        275                 280                 285

Gln Cys Val Ala Tyr Lys Ser Asp Gln Thr Lys Trp Val Phe Asn Ser
290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
        355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
        435                 440                 445

Ala Val Leu Cys Ala Cys Lys Ala Arg Arg Glu Cys Leu Thr Pro Tyr
450                 455                 460
```

```
Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
        515                 520                 525

Phe Leu Val Val Ala Gly Ala Tyr Leu Ala Lys Val Asp Ala Tyr Glu
    530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
    690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
    770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
```

```
                        885                 890                 895
His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
            915                 920                 925

Ile Val Ser Thr Pro His Lys Asn Asp Gln Glu Phe Gln Ala Ala Ile
            930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
            965                 970                 975

Thr Ser Thr Arg Arg
            980

<210> SEQ ID NO 11
<211> LENGTH: 982
<212> TYPE: PRT
<213> ORGANISM: Sindbis virus

<400> SEQUENCE: 11

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Lys Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
```

```
                275                 280                 285
Lys Gln Cys Val Ala Tyr Lys Ser Asp Gln Thr Lys Trp Val Phe Asn
290                 295                 300
Ser Pro Asp Leu Ile Arg His Asp His Thr Ala Gln Gly Lys Leu
305                 310                 315                 320
His Leu Pro Phe Lys Leu Ile Pro Ser Thr Cys Met Val Pro Val Ala
                325                 330                 335
His Ala Pro Asn Val Ile His Gly Phe Lys His Ile Ser Leu Gln Leu
                340                 345                 350
Asp Thr Asp His Leu Thr Leu Leu Thr Thr Arg Arg Leu Gly Ala Asn
                355                 360                 365
Pro Glu Pro Thr Thr Glu Trp Ile Val Gly Lys Thr Val Arg Asn Phe
370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                405                 410                 415
Pro His Glu Ile Val Gln His Tyr Tyr His Arg His Pro Val Tyr Thr
                420                 425                 430
Ile Leu Ala Val Ala Ser Ala Thr Val Ala Met Met Ile Gly Val Thr
                435                 440                 445
Val Ala Val Leu Cys Ala Cys Lys Ala Arg Arg Glu Cys Leu Thr Pro
450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                485                 490                 495
Tyr Leu Trp Ser Asn Ser Gln Pro Phe Phe Trp Val Gln Leu Cys Ile
                500                 505                 510
Pro Leu Ala Ala Phe Ile Val Leu Met Arg Cys Cys Ser Cys Cys Leu
                515                 520                 525
Pro Phe Leu Val Val Ala Gly Ala Tyr Leu Ala Lys Val Asp Ala Tyr
530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
                580                 585                 590
Lys Phe Thr Thr Val Val Pro Ser Pro Lys Ile Lys Cys Cys Gly Ser
                595                 600                 605
Leu Glu Cys Gln Pro Ala Ala His Ala Asp Tyr Thr Cys Lys Val Phe
610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
                660                 665                 670
Lys Val Gly Leu Arg Ile Val Tyr Gly Asn Thr Thr Ser Phe Leu Asp
                675                 680                 685
Val Tyr Val Asn Gly Val Thr Pro Gly Thr Ser Lys Asp Leu Lys Val
                690                 695                 700
```

```
Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
            725                 730                 735

Ala Met Lys Pro Gly Ala Phe Gly Asp Ile Gln Ala Thr Ser Leu Thr
            740                 745                 750

Ser Lys Asp Leu Ile Ala Ser Thr Asp Ile Arg Leu Leu Lys Pro Ser
            755                 760                 765

Ala Lys Asn Val His Val Pro Tyr Thr Gln Ala Ser Ser Gly Phe Glu
            770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
            820                 825                 830

Thr Ser Asp Ala Pro Leu Val Ser Thr Val Lys Cys Glu Val Ser Glu
            835                 840                 845

Cys Thr Tyr Ser Ala Asp Phe Gly Gly Met Ala Thr Leu Gln Tyr Val
            850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
            900                 905                 910

Cys Gly Lys Lys Thr Thr Cys Asn Ala Glu Cys Lys Pro Pro Ala Asp
            915                 920                 925

His Ile Val Ser Thr Pro His Lys Asn Asp Gln Glu Phe Gln Ala Ala
            930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
            980

<210> SEQ ID NO 12
<211> LENGTH: 981
<212> TYPE: PRT
<213> ORGANISM: Sindbis virus

<400> SEQUENCE: 12

Met Ser Ala Ala Pro Leu Val Thr Ala Met Cys Leu Leu Gly Asn Val
1               5

```
Glu Gln Val Trp Asp Glu Ala Asp Asp Asn Thr Ile Arg Ile Gln Thr
                100                 105                 110
Ser Ala Gln Phe Gly Tyr Asp Gln Ser Gly Ala Ala Ser Ala Asn Lys
                115                 120                 125
Tyr Arg Tyr Met Ser Leu Lys Gln Asp His Thr Val Glu Glu Gly Thr
                130                 135                 140
Met Asp Asp Ile Lys Ile Ser Thr Ser Gly Pro Cys Arg Arg Leu Ser
145                 150                 155                 160
Tyr Lys Gly Tyr Phe Leu Leu Ala Lys Cys Pro Pro Gly Asp Ser Val
                165                 170                 175
Thr Val Ser Ile Val Ser Ser Asn Ser Ala Thr Ser Cys Thr Leu Ala
                180                 185                 190
Arg Lys Ile Lys Pro Lys Phe Val Gly Arg Glu Lys Tyr Asp Leu Pro
                195                 200                 205
Pro Val His Gly Lys Lys Ile Pro Cys Thr Val Tyr Asp Arg Leu Lys
                210                 215                 220
Thr Thr Ala Gly Tyr Ile Thr Met His Arg Pro Arg Pro His Ala Tyr
225                 230                 235                 240
Thr Ser Tyr Leu Glu Glu Ser Ser Gly Lys Val Tyr Ala Lys Pro Pro
                245                 250                 255
Ser Gly Lys Asn Ile Thr Tyr Glu Cys Lys Cys Gly Asp Tyr Lys Thr
                260                 265                 270
Gly Thr Val Ser Thr Arg Thr Glu Ile Thr Gly Cys Thr Ala Ile Lys
                275                 280                 285
Gln Cys Val Ala Tyr Lys Ser Asp Gln Thr Lys Trp Val Phe Asn Ser
                290                 295                 300
Pro Asp Leu Ile Arg His Asp Asp His Thr Ala Gln Gly Lys Leu His
305                 310                 315                 320
Leu Pro Phe Lys Leu Ile Pro Ser Thr Cys Met Val Pro Val Ala His
                325                 330                 335
Ala Pro Asn Val Ile His Gly Phe Lys His Ile Ser Leu Gln Leu Asp
                340                 345                 350
Thr Asp His Leu Thr Leu Leu Thr Thr Arg Arg Leu Gly Ala Asn Pro
                355                 360                 365
Glu Pro Thr Thr Glu Trp Ile Val Gly Lys Thr Val Arg Asn Phe Thr
                370                 375                 380
Val Asp Arg Asp Gly Leu Glu Tyr Ile Trp Gly Asn His Glu Pro Val
385                 390                 395                 400
Arg Val Tyr Ala Gln Glu Ser Ala Pro Gly Asp Pro His Gly Trp Pro
                405                 410                 415
His Glu Ile Val Gln His Tyr Tyr His Arg His Pro Val Tyr Thr Ile
                420                 425                 430
Leu Ala Val Ala Ser Ala Thr Val Ala Met Met Ile Gly Val Thr Val
                435                 440                 445
Ala Val Leu Cys Ala Cys Lys Ala Arg Arg Glu Cys Leu Thr Pro Tyr
                450                 455                 460
Ala Leu Ala Pro Asn Ala Val Ile Pro Thr Ser Leu Ala Leu Leu Cys
465                 470                 475                 480
Cys Val Arg Ser Ala Asn Ala Glu Thr Phe Thr Glu Thr Met Ser Tyr
                485                 490                 495
Leu Trp Ser Asn Ser Gln Pro Phe Phe Trp Val Gln Leu Cys Ile Pro
                500                 505                 510
Leu Ala Ala Phe Ile Val Leu Met Arg Cys Cys Ser Cys Cys Leu Pro
                515                 520                 525
```

```
Phe Leu Val Val Ala Gly Ala Tyr Leu Ala Lys Val Asp Ala Tyr Glu
    530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
        595                 600                 605

Glu Cys Gln Pro Ala Ala His Ala Asp Tyr Thr Cys Lys Val Phe Gly
    610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
    690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
    770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
    850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
    930                 935                 940

Ser Lys Thr Ser Trp Ser Trp Leu Phe Ala Leu Phe Gly Gly Ala Ser
```

```
            945                 950                 955                 960
        Ser Leu Leu Ile Ile Gly Leu Met Ile Phe Ala Cys Ser Met Met Leu
                        965                 970                 975
        Thr Ser Thr Arg Arg
                        980

<210> SEQ ID NO 13
<211> LENGTH: 982
<212> TYPE: PRT
<213> ORGANISM: Sindbis virus

<400> SEQUENCE: 13

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Lys Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
```

-continued

```
                    340                 345                 350
Asp Thr Asp His Leu Thr Leu Leu Thr Thr Arg Arg Leu Gly Ala Asn
                355                 360                 365
Pro Glu Pro Thr Thr Glu Trp Ile Val Gly Lys Thr Val Arg Asn Phe
            370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                405                 410                 415
Pro His Glu Ile Val Gln His Tyr Tyr His Arg His Pro Val Tyr Thr
            420                 425                 430
Ile Leu Ala Val Ala Ser Ala Thr Val Ala Met Met Ile Gly Val Thr
                435                 440                 445
Val Ala Val Leu Cys Ala Cys Lys Ala Arg Arg Glu Cys Leu Thr Pro
            450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                485                 490                 495
Tyr Leu Trp Ser Asn Ser Gln Pro Phe Phe Trp Val Gln Leu Cys Ile
            500                 505                 510
Pro Leu Ala Ala Phe Ile Val Leu Met Arg Cys Cys Ser Cys Cys Leu
            515                 520                 525
Pro Phe Leu Val Val Ala Gly Ala Tyr Leu Ala Lys Val Asp Ala Tyr
        530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
            580                 585                 590
Lys Phe Thr Thr Val Val Pro Ser Pro Lys Ile Lys Cys Cys Gly Ser
            595                 600                 605
Leu Glu Cys Gln Pro Ala Ala His Ala Asp Tyr Thr Cys Lys Val Phe
        610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
            660                 665                 670
Lys Val Gly Leu Arg Ile Val Tyr Gly Asn Thr Thr Ser Phe Leu Asp
        675                 680                 685
Val Tyr Val Asn Gly Val Thr Pro Gly Thr Ser Lys Asp Leu Lys Val
690                 695                 700
Ile Ala Gly Pro Ile Ser Ala Ser Phe Thr Pro Phe Asp His Lys Val
            705                 710                 715                 720
Val Ile His Arg Gly Leu Val Tyr Asn Tyr Asp Phe Pro Glu Tyr Gly
                725                 730                 735
Ala Met Lys Pro Gly Ala Phe Gly Asp Ile Gln Ala Thr Ser Leu Thr
            740                 745                 750
Ser Lys Asp Leu Ile Ala Ser Thr Asp Ile Arg Leu Leu Lys Pro Ser
            755                 760                 765
```

-continued

```
Ala Lys Asn Val His Val Pro Tyr Thr Gln Ala Ser Ser Gly Phe Glu
    770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
                820                 825                 830

Thr Ser Asp Ala Pro Leu Val Ser Thr Val Lys Cys Glu Val Ser Glu
                835                 840                 845

Cys Thr Tyr Ser Ala Asp Phe Gly Gly Met Ala Thr Leu Gln Tyr Val
850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
                900                 905                 910

Cys Gly Lys Lys Thr Thr Cys Asn Ala Glu Cys Lys Pro Pro Ala Asp
                915                 920                 925

His Ile Val Ser Thr Pro His Lys Asn Asp Gln Glu Phe Gln Ala Ala
                930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
                980

<210> SEQ ID NO 14
<211> LENGTH: 981
<212> TYPE: PRT
<213> ORGANISM: Sindbis virus

<400> SEQUENCE: 14

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Lys Glu Gly Thr
            130                 135                 140

Met Asp Asp Ile Lys Ile Ser Thr Ser Gly Pro Cys Arg Arg Leu Ser
145                 150                 155                 160
```

-continued

Tyr Lys Gly Tyr Phe Leu Leu Ala Lys Cys Pro Pro Gly Asp Ser Val
            165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
            195                 200                 205

Pro Val His Gly Lys Lys Ile Pro Cys Thr Val Tyr Asp Arg Leu Lys
210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
            245                 250                 255

Ser Gly Lys Asn Ile Thr Tyr Glu Cys Lys Cys Gly Asp Tyr Lys Thr
            260                 265                 270

Gly Thr Val Ser Thr Arg Thr Glu Ile Thr Gly Cys Thr Ala Ile Lys
            275                 280                 285

Gln Cys Val Ala Tyr Lys Ser Asp Gln Thr Lys Trp Val Phe Asn Ser
            290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
            325                 330                 335

Ala Pro Asn Val Ile His Gly Phe Lys His Ile Ser Leu Gln Leu Asp
            340                 345                 350

Thr Asp His Leu Thr Leu Leu Thr Thr Arg Arg Leu Gly Ala Asn Pro
            355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
            405                 410                 415

His Glu Ile Val Gln His Tyr Tyr His Arg His Pro Val Tyr Thr Ile
            420                 425                 430

Leu Ala Val Ala Ser Ala Thr Val Ala Met Met Ile Gly Val Thr Val
            435                 440                 445

Ala Val Leu Cys Ala Cys Lys Ala Arg Arg Glu Cys Leu Thr Pro Tyr
450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
            485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
            515                 520                 525

Phe Leu Val Val Ala Gly Ala Tyr Leu Ala Lys Val Asp Ala Tyr Glu
            530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
            565                 570                 575

Ser Ser Glu Val Leu Pro Ser Thr Asn Gln Glu Tyr Ile Thr Cys Lys
            580                 585                 590

```
Phe Thr Thr Val Val Pro Ser Pro Lys Ile Lys Cys Cys Gly Ser Leu
            595                 600                 605

Glu Cys Gln Pro Ala Ala His Ala Asp Tyr Thr Cys Lys Val Phe Gly
        610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655

Ala Ser Asp His Ala Gln Ala Ile Lys Val His Thr Ala Ala Met Lys
            660                 665                 670

Val Gly Leu Arg Ile Val Tyr Gly Asn Thr Thr Ser Phe Leu Asp Val
        675                 680                 685

Tyr Val Asn Gly Val Thr Pro Gly Thr Ser Lys Asp Leu Lys Val Ile
690                 695                 700

Ala Gly Pro Ile Ser Ala Ser Phe Thr Pro Phe Asp His Lys Val Val
705                 710                 715                 720

Ile His Arg Gly Leu Val Tyr Asn Tyr Asp Phe Pro Glu Tyr Gly Ala
                725                 730                 735

Met Lys Pro Gly Ala Phe Gly Asp Ile Gln Ala Thr Ser Leu Thr Ser
            740                 745                 750

Lys Asp Leu Ile Ala Ser Thr Asp Ile Arg Leu Leu Lys Pro Ser Ala
        755                 760                 765

Lys Asn Val His Val Pro Tyr Thr Gln Ala Ser Ser Gly Phe Glu Met
770                 775                 780

Trp Lys Asn Asn Ser Gly Arg Pro Leu Gln Glu Thr Ala Pro Phe Gly
785                 790                 795                 800

Cys Lys Ile Ala Val Asn Pro Leu Arg Ala Val Asp Cys Ser Tyr Gly
                805                 810                 815

Asn Ile Pro Ile Ser Ile Asp Ile Pro Asn Ala Ala Phe Ile Arg Thr
            820                 825                 830

Ser Asp Ala Pro Leu Val Ser Thr Val Lys Cys Glu Val Ser Glu Cys
        835                 840                 845

Thr Tyr Ser Ala Asp Phe Gly Gly Met Ala Thr Leu Gln Tyr Val Ser
850                 855                 860

Asp Arg Glu Gly Gln Cys Pro Val His Ser His Ser Ser Thr Ala Thr
865                 870                 875                 880

Leu Gln Glu Ser Thr Val His Val Leu Glu Lys Gly Ala Val Thr Val
                885                 890                 895

His Phe Ser Thr Ala Ser Pro Gln Ala Asn Phe Ile Val Ser Leu Cys
            900                 905                 910

Gly Lys Lys Thr Thr Cys Asn Ala Glu Cys Lys Pro Pro Ala Asp His
        915                 920                 925

Ile Val Ser Thr Pro His Lys Asn Asp Gln Glu Phe Gln Ala Ala Ile
930                 935                 940

Ser Lys Thr Ser Trp Ser Trp Leu Phe Ala Leu Phe Gly Gly Ala Ser
945                 950                 955                 960

Ser Leu Leu Ile Ile Gly Leu Met Ile Phe Ala Cys Ser Met Met Leu
                965                 970                 975

Thr Ser Thr Arg Arg
            980

<210> SEQ ID NO 15
<211> LENGTH: 982
<212> TYPE: PRT
```

-continued

<213> ORGANISM: Sindbis virus

<400> SEQUENCE: 15

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
            20                  25                  30

Arg Ala Leu Asp Ile Leu Glu Glu Asn Val Asn His Glu Ala Tyr Asp
        35                  40                  45

Thr Leu Leu Asn Ala Ile Leu Arg Cys Gly Ser Ser Gly Arg Ser Lys
    50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
            85                  90                  95

Glu Gln Val Trp Asp Glu Ala Asp Asp Asn Thr Ile Arg Ile Gln Thr
            100                 105                 110

Ser Ala Gln Phe Gly Tyr Asp Gln Ser Gly Ala Ala Ser Ala Asn Lys
        115                 120                 125

Tyr Arg Tyr Met Ser Leu Glu Gln Asp His Thr Val Glu Glu Gly Thr
    130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
            165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Gly Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
            245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
            325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp

```
                    405                 410                 415
Pro His Glu Ile Val Gln His Tyr Tyr His Arg His Pro Val Tyr Thr
            420                 425                 430
Ile Leu Ala Val Ala Ser Ala Thr Val Ala Met Met Ile Gly Val Thr
            435                 440                 445
Val Ala Val Leu Cys Ala Cys Lys Ala Arg Arg Glu Cys Leu Thr Pro
            450                 455                 460
Tyr Ala Leu Ala Pro Asn Ala Val Ile Pro Thr Ser Leu Ala Leu Leu
465                 470                 475                 480
Cys Cys Val Arg Ser Ala Asn Ala Glu Thr Phe Thr Glu Thr Met Ser
                485                 490                 495
Tyr Leu Trp Ser Asn Ser Gln Pro Phe Phe Trp Val Gln Leu Cys Ile
            500                 505                 510
Pro Leu Ala Ala Phe Ile Val Leu Met Arg Cys Cys Ser Cys Cys Leu
            515                 520                 525
Pro Phe Leu Val Val Ala Gly Ala Tyr Leu Ala Lys Val Asp Ala Tyr
            530                 535                 540
Glu His Ala Thr Thr Val Pro Asn Val Pro Gln Ile Pro Tyr Lys Ala
545                 550                 555                 560
Leu Val Glu Arg Ala Gly Tyr Ala Pro Leu Asn Leu Glu Ile Thr Val
                565                 570                 575
Met Ser Ser Glu Val Leu Pro Ser Thr Asn Gln Glu Tyr Ile Thr Cys
            580                 585                 590
Lys Phe Thr Thr Val Val Pro Ser Pro Lys Ile Lys Cys Cys Gly Ser
            595                 600                 605
Leu Glu Cys Gln Pro Ala Ala His Ala Asp Tyr Thr Cys Lys Val Phe
            610                 615                 620
Gly Gly Val Tyr Pro Phe Met Trp Gly Gly Ala Gln Cys Phe Cys Asp
625                 630                 635                 640
Ser Glu Asn Ser Gln Met Ser Glu Ala Tyr Val Glu Leu Ser Ala Asp
                645                 650                 655
Cys Ala Ser Asp His Ala Gln Ala Ile Lys Val His Thr Ala Ala Met
            660                 665                 670
Lys Val Gly Leu Arg Ile Val Tyr Gly Asn Thr Thr Ser Phe Leu Asp
            675                 680                 685
Val Tyr Val Asn Gly Val Thr Pro Gly Thr Ser Lys Asp Leu Lys Val
            690                 695                 700
Ile Ala Gly Pro Ile Ser Ala Ser Phe Thr Pro Phe Asp His Lys Val
705                 710                 715                 720
Val Ile His Arg Gly Leu Val Tyr Asn Tyr Asp Phe Pro Glu Tyr Gly
                725                 730                 735
Ala Met Lys Pro Gly Ala Phe Gly Asp Ile Gln Ala Thr Ser Leu Thr
            740                 745                 750
Ser Lys Asp Leu Ile Ala Ser Thr Asp Ile Arg Leu Leu Lys Pro Ser
            755                 760                 765
Ala Lys Asn Val His Val Pro Tyr Thr Gln Ala Ser Ser Gly Phe Glu
            770                 775                 780
Met Trp Lys Asn Asn Ser Gly Arg Pro Leu Gln Glu Thr Ala Pro Phe
785                 790                 795                 800
Gly Cys Lys Ile Ala Val Asn Pro Leu Arg Ala Val Asp Cys Ser Tyr
                805                 810                 815
Gly Asn Ile Pro Ile Ser Ile Asp Ile Pro Asn Ala Ala Phe Ile Arg
            820                 825                 830
```

```
Thr Ser Asp Ala Pro Leu Val Ser Thr Val Lys Cys Glu Val Ser Glu
        835                 840                 845

Cys Thr Tyr Ser Ala Asp Phe Gly Gly Met Ala Thr Leu Gln Tyr Val
        850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                885                 890                 895

Val His Phe Ser Thr Ala Ser Pro Gln Ala Asn Phe Ile Val Ser Leu
                900                 905                 910

Cys Gly Lys Lys Thr Thr Cys Asn Ala Glu Cys Lys Pro Pro Ala Asp
                915                 920                 925

His Ile Val Ser Thr Pro His Lys Asn Asp Gln Glu Phe Gln Ala Ala
                930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
                965                 970                 975

Leu Thr Ser Thr Arg Arg
                980

<210> SEQ ID NO 16
<211> LENGTH: 981
<212> TYPE: PRT
<213> ORGANISM: Sindbis virus

<400> SEQUENCE: 16

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
        50                  55                  60

Arg Ser Val Ile Asp Asp Phe Thr Leu Thr Ser Pro Tyr Leu Gly Thr
65                  70                  75                  80

Cys Ser Tyr Cys His His Thr Val Pro Cys Phe Ser Pro Val Lys Ile
                85                  90                  95

Glu Gln Val Trp Asp Glu Ala Asp Asp Asn Thr Ile Arg Ile Gln Thr
                100                 105                 110

Ser Ala Gln Phe Gly Tyr Asp Gln Ser Gly Ala Ala Ser Ala Asn Lys
            115                 120                 125

Tyr Arg Tyr Met Ser Leu Glu Gln Asp His Thr Val Glu Glu Gly Thr
        130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
        210                 215                 220
```

```
Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
            245                 250                 255

Ser Gly Lys Asn Ile Thr Tyr Glu Cys Lys Cys Gly Asp Tyr Lys Thr
                260                 265                 270

Gly Thr Val Ser Thr Arg Thr Glu Ile Thr Gly Cys Thr Ala Ile Lys
            275                 280                 285

Gln Cys Val Ala Tyr Lys Ser Asp Gln Thr Lys Trp Val Phe Asn Ser
290                 295                 300

Pro Asp Leu Ile Arg His Asp Asp His Thr Ala Gln Gly Lys Leu His
305                 310                 315                 320

Leu Pro Phe Lys Leu Ile Pro Ser Thr Cys Met Val Pro Val Ala His
                325                 330                 335

Ala Pro Asn Val Ile His Gly Phe Lys His Ile Ser Leu Gln Leu Asp
                340                 345                 350

Thr Asp His Leu Thr Leu Leu Thr Arg Arg Leu Gly Ala Asn Pro
            355                 360                 365

Glu Pro Thr Thr Glu Trp Ile Val Gly Lys Thr Val Arg Asn Phe Thr
370                 375                 380

Val Asp Arg Asp Gly Leu Glu Tyr Ile Trp Gly Asn His Glu Pro Val
385                 390                 395                 400

Arg Val Tyr Ala Gln Glu Ser Ala Pro Gly Asp Pro His Gly Trp Pro
                405                 410                 415

His Glu Ile Val Gln His Tyr Tyr His Arg Pro Val Tyr Thr Ile
            420                 425                 430

Leu Ala Val Ala Ser Ala Thr Val Ala Met Met Ile Gly Val Thr Val
            435                 440                 445

Ala Val Leu Cys Ala Cys Lys Ala Arg Arg Glu Cys Leu Thr Pro Tyr
            450                 455                 460

Ala Leu Ala Pro Asn Ala Val Ile Pro Thr Ser Leu Ala Leu Leu Cys
465                 470                 475                 480

Cys Val Arg Ser Ala Asn Ala Glu Thr Phe Thr Glu Thr Met Ser Tyr
                485                 490                 495

Leu Trp Ser Asn Ser Gln Pro Phe Phe Trp Val Gln Leu Cys Ile Pro
            500                 505                 510

Leu Ala Ala Phe Ile Val Leu Met Arg Cys Cys Ser Cys Cys Leu Pro
            515                 520                 525

Phe Leu Val Val Ala Gly Ala Tyr Leu Ala Lys Val Asp Ala Tyr Glu
530                 535                 540

His Ala Thr Thr Val Pro Asn Val Pro Gln Ile Pro Tyr Lys Ala Leu
545                 550                 555                 560

Val Glu Arg Ala Gly Tyr Ala Pro Leu Asn Leu Glu Ile Thr Val Met
                565                 570                 575

Ser Ser Glu Val Leu Pro Ser Thr Asn Gln Glu Tyr Ile Thr Cys Lys
            580                 585                 590

Phe Thr Thr Val Val Pro Ser Pro Lys Ile Lys Cys Cys Gly Ser Leu
            595                 600                 605

Glu Cys Gln Pro Ala Ala His Ala Asp Tyr Thr Cys Lys Val Phe Gly
610                 615                 620

Gly Val Tyr Pro Phe Met Trp Gly Gly Ala Gln Cys Phe Cys Asp Ser
625                 630                 635                 640

Glu Asn Ser Gln Met Ser Glu Ala Tyr Val Glu Leu Ser Ala Asp Cys
                645                 650                 655
```

```
Ala Ser Asp His Ala Gln Ala Ile Lys Val His Thr Ala Ala Met Lys
            660                 665                 670
Val Gly Leu Arg Ile Val Tyr Gly Asn Thr Thr Ser Phe Leu Asp Val
        675                 680                 685
Tyr Val Asn Gly Val Thr Pro Gly Thr Ser Lys Asp Leu Lys Val Ile
690                 695                 700
Ala Gly Pro Ile Ser Ala Ser Phe Thr Pro Phe Asp His Lys Val Val
705                 710                 715                 720
Ile His Arg Gly Leu Val Tyr Asn Tyr Asp Phe Pro Glu Tyr Gly Ala
                725                 730                 735
Met Lys Pro Gly Ala Phe Gly Asp Ile Gln Ala Thr Ser Leu Thr Ser
            740                 745                 750
Lys Asp Leu Ile Ala Ser Thr Asp Ile Arg Leu Leu Lys Pro Ser Ala
        755                 760                 765
Lys Asn Val His Val Pro Tyr Thr Gln Ala Ser Ser Gly Phe Glu Met
770                 775                 780
Trp Lys Asn Asn Ser Gly Arg Pro Leu Gln Glu Thr Ala Pro Phe Gly
785                 790                 795                 800
Cys Lys Ile Ala Val Asn Pro Leu Arg Ala Val Asp Cys Ser Tyr Gly
                805                 810                 815
Asn Ile Pro Ile Ser Ile Asp Ile Pro Asn Ala Ala Phe Ile Arg Thr
            820                 825                 830
Ser Asp Ala Pro Leu Val Ser Thr Val Lys Cys Glu Val Ser Glu Cys
        835                 840                 845
Thr Tyr Ser Ala Asp Phe Gly Gly Met Ala Thr Leu Gln Tyr Val Ser
850                 855                 860
Asp Arg Glu Gly Gln Cys Pro Val His Ser His Ser Ser Thr Ala Thr
865                 870                 875                 880
Leu Gln Glu Ser Thr Val His Val Leu Glu Lys Gly Ala Val Thr Val
                885                 890                 895
His Phe Ser Thr Ala Ser Pro Gln Ala Asn Phe Ile Val Ser Leu Cys
            900                 905                 910
Gly Lys Lys Thr Thr Cys Asn Ala Glu Cys Lys Pro Pro Ala Asp His
        915                 920                 925
Ile Val Ser Thr Pro His Lys Asn Asp Gln Glu Phe Gln Ala Ala Ile
930                 935                 940
Ser Lys Thr Ser Trp Ser Trp Leu Phe Ala Leu Phe Gly Gly Ala Ser
945                 950                 955                 960
Ser Leu Leu Ile Ile Gly Leu Met Ile Phe Ala Cys Ser Met Met Leu
                965                 970                 975
Thr Ser Thr Arg Arg
            980

<210> SEQ ID NO 17
<211> LENGTH: 982
<212> TYPE: PRT
<213> ORGANISM: Sindbis virus

<400> SEQUENCE: 17

Met Ser Ala Ala Pro Leu Val Thr Ala Met Cys Leu Leu Gly Asn Val
1               5                   10                  15
Ser Phe Pro Cys Asp Arg Pro Pro Thr Cys Tyr Thr Arg Glu Pro Ser
            20                  25                  30
Arg Ala Leu Asp Ile Leu Glu Glu Asn Val Asn His Glu Ala Tyr Asp
        35                  40                  45
```

-continued

```
Thr Leu Leu Asn Ala Ile Leu Arg Cys Gly Ser Ser Gly Arg Ser Lys
    50                  55                  60
Arg Ser Val Ile Asp Asp Phe Thr Leu Thr Ser Pro Tyr Leu Gly Thr
 65                  70                  75                  80
Cys Ser Tyr Cys His His Thr Val Pro Cys Phe Ser Pro Val Lys Ile
                 85                  90                  95
Glu Gln Val Trp Asp Glu Ala Asp Asn Thr Ile Arg Ile Gln Thr
            100                 105                 110
Ser Ala Gln Phe Gly Tyr Asp Gln Ser Gly Ala Ala Ser Ala Asn Lys
            115                 120                 125
Tyr Arg Tyr Met Ser Leu Lys Gln Asp His Thr Val Lys Glu Gly Thr
        130                 135                 140
Met Asp Asp Ile Lys Ile Ser Thr Ser Gly Pro Cys Arg Arg Leu Ser
145                 150                 155                 160
Tyr Lys Gly Tyr Phe Leu Leu Ala Lys Cys Pro Pro Gly Asp Ser Val
                165                 170                 175
Thr Val Ser Ile Val Ser Ser Asn Ser Ala Thr Ser Cys Thr Leu Ala
            180                 185                 190
Arg Lys Ile Lys Pro Lys Phe Val Gly Arg Glu Lys Tyr Asp Leu Pro
        195                 200                 205
Pro Val His Gly Lys Lys Ile Pro Cys Thr Val Tyr Asp Arg Leu Lys
    210                 215                 220
Glu Thr Thr Ala Gly Tyr Ile Thr Met His Arg Pro Arg Pro His Ala
225                 230                 235                 240
Tyr Thr Ser Tyr Leu Glu Glu Ser Ser Gly Lys Val Tyr Ala Lys Pro
                245                 250                 255
Pro Ser Gly Lys Asn Ile Thr Tyr Glu Cys Lys Cys Gly Asp Tyr Lys
            260                 265                 270
Thr Gly Thr Val Ser Thr Arg Thr Glu Ile Thr Gly Cys Thr Ala Ile
        275                 280                 285
Lys Gln Cys Val Ala Tyr Lys Ser Asp Gln Thr Lys Trp Val Phe Asn
    290                 295                 300
Ser Pro Asp Leu Ile Arg His Asp Asp His Thr Ala Gln Gly Lys Leu
305                 310                 315                 320
His Leu Pro Phe Lys Leu Ile Pro Ser Thr Cys Met Val Pro Val Ala
                325                 330                 335
His Ala Pro Asn Val Ile His Gly Phe Lys His Ile Ser Leu Gln Leu
            340                 345                 350
Asp Thr Asp His Leu Thr Leu Leu Thr Thr Arg Arg Leu Gly Ala Asn
        355                 360                 365
Pro Glu Pro Thr Thr Glu Trp Ile Val Gly Lys Thr Val Arg Asn Phe
    370                 375                 380
Thr Val Asp Arg Asp Gly Leu Glu Tyr Ile Trp Gly Asn His Glu Pro
385                 390                 395                 400
Val Arg Val Tyr Ala Gln Glu Ser Ala Pro Gly Asp Pro His Gly Trp
                405                 410                 415
Pro His Glu Ile Val Gln His Tyr Tyr His Arg His Pro Val Tyr Thr
            420                 425                 430
Ile Leu Ala Val Ala Ser Ala Thr Val Ala Met Met Ile Gly Val Thr
        435                 440                 445
Val Ala Val Leu Cys Ala Cys Lys Ala Arg Arg Glu Cys Leu Thr Pro
    450                 455                 460
Tyr Ala Leu Ala Pro Asn Ala Val Ile Pro Thr Ser Leu Ala Leu Leu
```

-continued

```
              465                 470                 475                 480
Cys Cys Val Arg Ser Ala Asn Ala Glu Thr Phe Thr Glu Thr Met Ser
                    485                 490                 495

Tyr Leu Trp Ser Asn Ser Gln Pro Phe Phe Trp Val Gln Leu Cys Ile
                500                 505                 510

Pro Leu Ala Ala Phe Ile Val Leu Met Arg Cys Cys Ser Cys Cys Leu
                515                 520                 525

Pro Phe Leu Val Val Ala Gly Ala Tyr Leu Ala Lys Val Asp Ala Tyr
            530                 535                 540

Glu His Ala Thr Thr Val Pro Asn Val Pro Gln Ile Pro Tyr Lys Ala
545                 550                 555                 560

Leu Val Glu Arg Ala Gly Tyr Ala Pro Leu Asn Leu Glu Ile Thr Val
                565                 570                 575

Met Ser Ser Glu Val Leu Pro Ser Thr Asn Gln Glu Tyr Ile Thr Cys
                580                 585                 590

Lys Phe Thr Thr Val Val Pro Ser Pro Lys Ile Lys Cys Cys Gly Ser
                595                 600                 605

Leu Glu Cys Gln Pro Ala Ala His Ala Asp Tyr Thr Cys Lys Val Phe
            610                 615                 620

Gly Gly Val Tyr Pro Phe Met Trp Gly Gly Ala Gln Cys Phe Cys Asp
625                 630                 635                 640

Ser Glu Asn Ser Gln Met Ser Glu Ala Tyr Val Glu Leu Ser Ala Asp
                    645                 650                 655

Cys Ala Ser Asp His Ala Gln Ala Ile Lys Val His Thr Ala Ala Met
                660                 665                 670

Lys Val Gly Leu Arg Ile Val Tyr Gly Asn Thr Thr Ser Phe Leu Asp
                675                 680                 685

Val Tyr Val Asn Gly Val Thr Pro Gly Thr Ser Lys Asp Leu Lys Val
            690                 695                 700

Ile Ala Gly Pro Ile Ser Ala Ser Phe Thr Pro Phe Asp His Lys Val
705                 710                 715                 720

Val Ile His Arg Gly Leu Val Tyr Asn Tyr Asp Phe Pro Glu Tyr Gly
                    725                 730                 735

Ala Met Lys Pro Gly Ala Phe Gly Asp Ile Gln Ala Thr Ser Leu Thr
                740                 745                 750

Ser Lys Asp Leu Ile Ala Ser Thr Asp Ile Arg Leu Leu Lys Pro Ser
                755                 760                 765

Ala Lys Asn Val His Val Pro Tyr Thr Gln Ala Ser Ser Gly Phe Glu
                770                 775                 780

Met Trp Lys Asn Asn Ser Gly Arg Pro Leu Gln Glu Thr Ala Pro Phe
785                 790                 795                 800

Gly Cys Lys Ile Ala Val Asn Pro Leu Arg Ala Val Asp Cys Ser Tyr
                805                 810                 815

Gly Asn Ile Pro Ile Ser Ile Asp Ile Pro Asn Ala Ala Phe Ile Arg
                820                 825                 830

Thr Ser Asp Ala Pro Leu Val Ser Thr Val Lys Cys Glu Val Ser Glu
                835                 840                 845

Cys Thr Tyr Ser Ala Asp Phe Gly Gly Met Ala Thr Leu Gln Tyr Val
            850                 855                 860

Ser Asp Arg Glu Gly Gln Cys Pro Val His Ser His Ser Ser Thr Ala
865                 870                 875                 880

Thr Leu Gln Glu Ser Thr Val His Val Leu Glu Lys Gly Ala Val Thr
                    885                 890                 895
```

```
Val His Phe Ser Thr Ala Ser Pro Gln Ala Asn Phe Ile Val Ser Leu
            900                 905                 910

Cys Gly Lys Thr Thr Cys Asn Ala Glu Cys Lys Pro Ala Asp
            915                 920                 925

His Ile Val Ser Thr Pro His Lys Asn Asp Gln Glu Phe Gln Ala Ala
            930                 935                 940

Ile Ser Lys Thr Ser Trp Ser Trp Leu Phe Ala Leu Phe Gly Gly Ala
945                 950                 955                 960

Ser Ser Leu Leu Ile Ile Gly Leu Met Ile Phe Ala Cys Ser Met Met
            965                 970                 975

Leu Thr Ser Thr Arg Arg
            980

<210> SEQ ID NO 18
<211> LENGTH: 423
<212> TYPE: PRT
<213> ORGANISM: Sindbis virus

<400> SEQUENCE: 18

Ser Val Ile Asp Asp Phe Thr Leu Thr Ser Pro Tyr Leu Gly Thr Cys
1               5                   10                  15

Ser Tyr Cys His His Thr Val Pro Cys Phe Ser Pro Val Lys Ile Glu
            20                  25                  30

Gln Val Trp Asp Glu Ala Asp Asp Asn Thr Ile Arg Ile Gln Thr Ser
            35                  40                  45

Ala Gln Phe Gly Tyr Asp Gln Ser Gly Ala Ala Ser Ala Asn Lys Tyr
        50                  55                  60

Arg Tyr Met Ser Leu Lys Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Val Ser Ser Asn Ser Ala Thr Ser Cys Thr Leu Ala Arg
            115                 120                 125

Lys Ile Lys Pro Lys Phe Val Gly Arg Glu Lys Tyr Asp Leu Pro Pro
        130                 135                 140

Val His Gly Lys Lys Ile Pro Cys Thr Val Tyr Asp Arg Leu Lys Glu
145                 150                 155                 160

Thr Thr Ala Gly Tyr Ile Thr Met His Arg Pro Arg Pro His Ala Tyr
                165                 170                 175

Thr Ser Tyr Leu Glu Glu Ser Ser Gly Lys Val Tyr Ala Lys Pro Pro
            180                 185                 190

Ser Gly Lys Asn Ile Thr Tyr Glu Cys Lys Cys Gly Asp Tyr Lys Thr
        195                 200                 205

Gly Thr Val Ser Thr Arg Thr Glu Ile Thr Gly Cys Thr Ala Ile Lys
210                 215                 220

Gln Cys Val Ala Tyr Lys Ser Asp Gln Thr Lys Trp Val Phe Asn Ser
225                 230                 235                 240

Pro Asp Leu Ile Arg His Asp Asp His Thr Ala Gln Gly Lys Leu His
                245                 250                 255

Leu Pro Phe Lys Leu Ile Pro Ser Thr Cys Met Val Pro Val Ala His
            260                 265                 270

Ala Pro Asn Val Ile His Gly Phe Lys His Ile Ser Leu Gln Leu Asp
        275                 280                 285
```

```
Thr Asp His Leu Thr Leu Leu Thr Arg Arg Leu Gly Ala Asn Pro
            290                 295                 300

Glu Pro Thr Thr Glu Trp Ile Val Gly Lys Thr Val Arg Asn Phe Thr
305                 310                 315                 320

Val Asp Arg Asp Gly Leu Glu Tyr Ile Trp Gly Asn His Glu Pro Val
                325                 330                 335

Arg Val Tyr Ala Gln Glu Ser Ala Pro Gly Asp Pro His Gly Trp Pro
            340                 345                 350

His Glu Ile Val Gln His Tyr Tyr His Arg His Pro Val Tyr Thr Ile
                355                 360                 365

Leu Ala Val Ala Ser Ala Thr Val Ala Met Met Ile Gly Val Thr Val
            370                 375                 380

Ala Val Leu Cys Ala Cys Lys Ala Arg Arg Glu Cys Leu Thr Pro Tyr
385                 390                 395                 400

Ala Leu Ala Pro Asn Ala Val Ile Pro Thr Ser Leu Ala Leu Leu Cys
                405                 410                 415

Cys Val Arg Ser Ala Asn Ala
            420

<210> SEQ ID NO 19
<211> LENGTH: 65
<212> TYPE: PRT
<213> ORGANISM: Sindbis virus

<400> SEQUENCE: 19

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Arg Ser Lys
        50                  55                  60

Arg
65

<210> SEQ ID NO 20
<211> LENGTH: 488
<212> TYPE: PRT
<213> ORGANISM: Sindbis virus

<400> SEQUENCE: 20

Met Ser Ala Ala Pro Leu Val Thr Ala Met Cys Leu Leu Gly Asn Val
1               5                   10                  15

Ser Phe Pro Cys Asp Arg Pro Pro Thr

```
                115                 120                 125
Tyr Arg Tyr Met Ser Leu Lys Gln Asp His Thr Val Lys Glu Gly Thr
            130                 135                 140

Met Asp Asp Ile Lys Ile Ser Thr Ser Gly Pro Cys Arg Arg Leu Ser
145                 150                 155                 160

Tyr Lys Gly Tyr Phe Leu Leu Ala Lys Cys Pro Pro Gly Asp Ser Val
                165                 170                 175

Thr Val Ser Ile Val Ser Ser Asn Ser Ala Thr Ser Cys Thr Leu Ala
            180                 185                 190

Arg Lys Ile Lys Pro Lys Phe Val Gly Arg Glu Lys Tyr Asp Leu Pro
        195                 200                 205

Pro Val His Gly Lys Lys Ile Pro Cys Thr Val Tyr Asp Arg Leu Lys
    210                 215                 220

Glu Thr Thr Ala Gly Tyr Ile Thr Met His Arg Pro Arg Pro His Ala
225                 230                 235                 240

Tyr Thr Ser Tyr Leu Glu Glu Ser Ser Gly Lys Val Tyr Ala Lys Pro
                245                 250                 255

Pro Ser Gly Lys Asn Ile Thr Tyr Glu Cys Lys Cys Gly Asp Tyr Lys
            260                 265                 270

Thr Gly Thr Val Ser Thr Arg Thr Glu Ile Thr Gly Cys Thr Ala Ile
        275                 280                 285

Lys Gln Cys Val Ala Tyr Lys Ser Asp Gln Thr Lys Trp Val Phe Asn
    290                 295                 300

Ser Pro Asp Leu Ile Arg His Asp Asp His Thr Ala Gln Gly Lys Leu
305                 310                 315                 320

His Leu Pro Phe Lys Leu Ile Pro Ser Thr Cys Met Val Pro Val Ala
                325                 330                 335

His Ala Pro Asn Val Ile His Gly Phe Lys His Ile Ser Leu Gln Leu
            340                 345                 350

Asp Thr Asp His Leu Thr Leu Leu Thr Thr Arg Arg Leu Gly Ala Asn
        355                 360                 365

Pro Glu Pro Thr Thr Glu Trp Ile Val Gly Lys Thr Val Arg Asn Phe
    370                 375                 380

Thr Val Asp Arg Asp Gly Leu Glu Tyr Ile Trp Gly Asn His Glu Pro
385                 390                 395                 400

Val Arg Val Tyr Ala Gln Glu Ser Ala Pro Gly Asp Pro His Gly Trp
                405                 410                 415

Pro His Glu Ile Val Gln His Tyr Tyr His Arg His Pro Val Tyr Thr
            420                 425                 430

Ile Leu Ala Val Ala Ser Ala Thr Val Ala Met Met Ile Gly Val Thr
        435                 440                 445

Val Ala Val Leu Cys Ala Cys Lys Ala Arg Arg Glu Cys Leu Thr Pro
    450                 455                 460

Tyr Ala Leu Ala Pro Asn Ala Val Ile Pro Thr Ser Leu Ala Leu Leu
465                 470                 475                 480

Cys Cys Val Arg Ser Ala Asn Ala
                485

<210> SEQ ID NO 21
<211> LENGTH: 683
<212> TYPE: DNA
<213> ORGANISM: Human immunodeficiency virus type 1

<400> SEQUENCE: 21
cctagaaaaa catggagcaa tcacaagtag caatacagca gctaccaatg ctgattgtgc    60
```

```
ctggctagaa gcacaagagg aggaggaggt gggttttcca gtcacacctc aggtaccttt      120
aagaccaatg acttacaagg cagctgtaga tcttagccac ttttttaaaag aaaaggggggg    180 actggaaggg ctaattcact cccaacgaag acaagatatc cttgatctgt ggatctacca     240
cacacaaggc tacttccctg attggcagaa ctacacacca gggccaggga tcagatatcc    300
actgaccttt ggatggtgct acaagctagt accagttgag caagagaagg tagaagaagc    360
caatgaagga gagaacaccc gcttgttaca ccctgtgagc ctgcatggga tggatgaccc    420
ggagagagaa gtattagagt ggaggtttga cagccgccta gcatttcatc acatggcccg    480
agagctgcat ccggactgta ctgggtctct ctggttagac cagatctgag cctgggagct    540
ctctggctaa ctagggaacc cactgcttaa gcctcaataa agcttgcctt gagtgcttca    600
agtagtgtgt gcccgtctgt tgtgtgactc tggtaactag agatccctca gacccttta     660 gtcagtgtgg aaaatctcta gca                                             683

<210> SEQ ID NO 22
<211> LENGTH: 416
<212> TYPE: DNA
<213> ORGANISM: Human immunodeficiency virus type 1

<400> SEQUENCE: 22
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac ttttttaaaag aaaaggggggg   180 actggaaggg ctaattcact cccaacgaag acaagatctg ctttttgcct gtactgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagacccct ttagtcagtg tggaaaatct ctagca         416

<210> SEQ ID NO 23
<211> LENGTH: 401
<212> TYPE: DNA
<213> ORGANISM: Human immunodeficiency virus type 1

<400> SEQUENCE: 23
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac ttttttactgg aagggctaat    180 tcactcccaa cgaagacaag atctgctttt tgcctgtact gggtctctct ggttagacca    240
gatctgagcc tgggagctct ctggctaact agggaaccca ctgcttaagc ctcaataaag    300
cttgccttga gtgcttcaag tagtgtgtgc ccgtctgttg tgtgactctg gtaactagag    360
atccctcaga cccttttagt cagtgtggaa aatctctagc a                         401

<210> SEQ ID NO 24
<211> LENGTH: 8
<212> TYPE: PRT
<213> ORGANISM: Gallus gallus

<400> SEQUENCE: 24

Ser Ile Ile Asn Phe Glu Lys Leu
1               5

<210> SEQ ID NO 25
```

```
<211> LENGTH: 9
<212> TYPE: PRT
<213> ORGANISM: Mus musculus

<400> SEQUENCE: 25

Ser Pro Ser Tyr Ala Tyr His Gln Phe
1               5

<210> SEQ ID NO 26
<211> LENGTH: 5
<212> TYPE: PRT
<213> ORGANISM: Sindbis virus

<400> SEQUENCE: 26

Arg Ser Lys Arg Ser
1               5

<210> SEQ ID NO 27
<211> LENGTH: 4
<212> TYPE: PRT
<213> ORGANISM: Sindbis virus

<400> SEQUENCE: 27

Arg Ser Lys Arg
1

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Asp Tyr Lys Asp Asp Asp Asp Lys
1               5

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide

<400> SEQUENCE: 29

Ala Ala Val Lys Asn Trp Met Thr Gln Thr Leu
1               5                   10
```

US 8,187,872 B2

LENTIVIRAL VECTORS PSEUDOTYPED WITH A SINDBIS VIRUS ENVELOPE GLYCOPROTEIN

CROSS-REFERENCE TO RELATED APPLICATIONS

This patent application is a continuation of U.S. patent application Ser. No. 12/842,609, filed Jul. 23, 2010, which claims priority to U.S. Provisional Application No. 61/228,491, filed 24 Jul. 2009, and to PCT/US10/042870, filed 22 Jul. 2010, all of which applications are incorporated by reference in their entirety.

REFERENCE TO SEQUENCE LISTING

The sequence listing of this patent application is provided separately in a file named "46434B SeqListing.txt". The content of this file, which was created on Dec. 28, 2011 and consists of a 150,574 byte ASCII text file, is incorporated by reference in its entirety.

TECHNICAL FIELD

This patent application relates generally to targeted gene delivery, and more particularly to the use of a pseudotyped lentivirus comprising an envelope that targets dendritic cells and can thus be used for dendritic cell vaccination.

BACKGROUND

Dendritic cells (DCs) are essential antigen presenting cells for the initiation and control of immune responses. DCs can capture and process antigens, migrate from the periphery to a lymphoid organ, and present the antigens to resting T cells in a major histocompatibility complex (MHC)-restricted fashion. These cells are derived from bone marrow (BM) and display dendritic morphology and high mobility. The discovery of DCs as specialized antigen-presenting cells (APCs) has fueled attempts at DC-based immunization/vaccination strategies that involve loading DCs in vitro with specific antigens (Banchereau and Palucka, A. K. 2005. Nat. Rev. Immunol. 5:296-306; Figdor, et al. 2004. Nat. Med. 10:475-480). All of these attempts however, involve the labor-intensive preparation of a patient-specific therapy that includes the loading of autologous DCs ex vivo with specific antigens, which are then administered to the patient.

An alternative strategy is to utilize recombinant virus-based vectors as a mechanism to directly deliver a gene encoding a designated antigen(s) to host cells. In this instance, through induction of a desired adaptive immune response, the expressed gene product provides therapeutic benefit. There are a number of challenges however to achieving a safe and effective system. Some of these challenges include designing a vector that targets a desired set of host cells, providing a suitable delivery system, expressing a desired antigen to elicit an effective immune response and consistently manufacturing a sufficiently high titered pharmaceutical composition of the recombinant virus vector virus so that it can be utilized broadly across a designated human subject population. The latter is a particular challenge in developing laboratory scale systems into products that can be produced by the pharmaceutical industry.

In the laboratory, many lentiviral vectors are pseudotyped with the VSV-G envelope proteins. This is widely used as a model system as the VSV envelope proteins are able to target many cell types (a "pantropic" envelope), and production systems generally provide a high titre.

The envelope glycoproteins of Sindbis virus and other alphaviruses disclosed herein incorporate into the lipid bilayer of the viral particle membrane. Typically, the viral membrane (envelope) includes multiple copies of trimers of two glycoprotein heterodimers. E1 and E2, which are produced from cleavage of a single precursor protein. The precursor protein comprises, from its N- to C-terminal, the E3, E2, 6K and E1 proteins. The small E3 glycoprotein serves as a signal sequence for translocation of the E2 protein into the membrane, and is cleaved from E2 by furin or some other Ca2+-dependent serine proteinase. The 6K protein serves as a signal sequence for translocation of the E1 protein into the membrane and is then cleaved from the precursor protein.

The E1 and E2 glycoproteins each have membrane-spanning regions; E2 has an about 33 residue cytoplasmic domain whereas the cytoplasmic tail of E1 is very short (about 2 residues). Both E1 and E2 have palmitic acids attached in or near the membrane-spanning regions.

Isolates of Sindbis virus described in the art are believed to infect cells via an interaction with heparan sulfate (HS). In WO 2008/011636 a lentiviral packaging system was described in which the E3/E2 envelope fusion protein (called SVGmu) contains a number of modifications, intended to reduce binding of the protein to HS but to retain binding to and infection of DCs, via the DC-SIGN surface molecule. Though the SVGmu pseudotyped viral particles were able to selectively transduce cells expressing the DC-SIGN antigen, several aspects of the system make it unsuitable for therapeutic use. For example, the E3/E2 fusion protein displays an antigenic epitope of influenza hemagglutinin, and significantly. Sindbis virus strains with a mutation preventing correct processing of E3 from the E2 glycoprotein (so-called "pE2 mutants"), such as SVGmu, grow poorly in permissive cell lines and are severely attenuated in mouse pathogenicity.

SUMMARY OF THE INVENTION

This patent application is directed to pseudotyped lentiviral vectors that comprise a genome having a sequence of interest and an envelope comprising a glycoprotein of an arbovirus. The arbovirus glycoprotein can be from Sindbis virus, Dengue virus, and Venezuelan equine encephalitis virus. In particular, when the glycoprotein is an E2 protein from Sindbis virus, the E2 protein has at least one amino acid alteration at residue 160 compared to SEQ ID NO: 1. The amino acid alteration can be a deletion or an amino acid other than glutamic acid. The glycoprotein facilitates infection of dendritic cells. In all cases the E2 glycoprotein is not part of a fusion protein with Sindbis virus E3. In some embodiments, the E2 glycoprotein or variant binds DC-SIGN. The lentiviral vector also comprises a lentiviral genome that comprises a sequence of interest.

In certain embodiments, residue 160 is absent or is glycine, alanine, valine, leucine or isoleucine. In one embodiment, residue 160 is glycine. In addition, other alterations of E2 glycoprotein can occur in combination with the mentioned alterations of residue 160. One such alteration is a change of an amino acid to reduce the net positive charge of E2. One way to reduce the net positive charge is to change one of the lysines to an amino acid that is not basic. In particular embodiments, one or more of lysine 70, lysine 76 or lysine 159 is altered. In certain embodiments, one or more of these lysines is changed to a glutamic acid or an aspartic acid. In specific embodiments, the E2 glycoprotein is one of sequences contained in SEQ ID NOs: 3-16. Examples of combinations of alterations include, without limitation, an alteration of glutamic acid at position 160, and alteration of one or more of lysine 70, lysine 76, or lysine 159 to a non-basic residue. Other alterations may be also be made, in combination with the alteration of residue 160 and optionally any of the other alterations disclosed herein. For example, any of the previously mentioned E2 glycoproteins may optionally comprise one or more further substitutions, insertions or deletions. As one specific example, the protein cleavage site between E2 and E3 can be either the native sequence or an altered sequence that is cleaved by a different endopeptidase. In other embodiments, which can be in combination with any of the above, the sequence of residues 71-75 of SEQ ID NO:1 is unchanged or has one or two amino acid substitutions which do not affect the ability of the variant to infect DCs.

In certain embodiments, the lentiviral vector genome of any of the foregoing viral particles comprises a sequence of interest that encodes a tumor-specific antigen or a virus-derived antigen, such as an HIV or SIV antigen. In some embodiments, any of the vector particles described are produced at a titer of at least $10^5$/mL IU.

In another aspect, a lentiviral vector packaging system for producing a pseudotyped lentiviral vector particle is provided, comprising: a first nucleic acid molecule encoding a Sindbis virus E2 glycoprotein of SEQ ID NO:1 in which residue 160 is absent or an amino acid other than glutamic acid, a lentiviral vector genome comprising a sequence of interest, a third nucleic acid molecule encoding gag and pol proteins; a fourth nucleic acid molecule encoding rev. The E2 glycoprotein or variant of the packaging system has an amino acid sequence as defined in any of the embodiments above. In some embodiments, the pol protein has a non-functional integrase. In a particular embodiment, the non-functional Integrase has a D64V mutation. In some embodiments, the second nucleic acid molecule is a non-integrating lentiviral genome. In particular embodiments, the att site is mutated or deleted or the PPT site is mutated or deleted or both. The non-integrating lentiviral genome can be used in combination with a non-functional Integrase and in combination with any of the E2 proteins or variants. It is preferred that lentiviral vector particles are produced to a titer of at least $10^5$ IU/mL. In some instances, a cell is transfected with the first and second nucleic acid molecules described above. The cell may already comprise the second and third nucleic acid molecules, in a stable transformation.

An isolated nucleic acid molecule is provided that encodes the glycoprotein as described above or an E3/E2 glycoprotein optionally in the form of a Sindbis E3/E2/6K/E1 polyprotein, or an E3/E2 glycoprotein wherein the E3 sequence corresponds to residues 1-65 of SEQ ID NO:20, or a variant thereof having at least 80% sequence identity to residues 1-65 of SEQ ID NO:20, wherein residues 62-65 are RSKR (SEQ ID NO: 27) and the variant is capable of being incorporated into a pseudotyped viral envelope, optionally further wherein residue 1 of the E2 polyprotein is Ser. The E2 glycoprotein can be any of the variants described above, including the combinations of alterations. In addition, an expression vector comprising the nucleic acid molecule is provided, as is a host cell comprising the expression vector.

A method of making a lentiviral vector particle of any one of the variants or combinations above is provided, comprising expressing in a cell a first nucleic acid molecule encoding a Sindbis virus E2 glycoprotein of SEQ ID NO:1 in which residue 160 is other than glutamic acid, and; a second nucleic acid molecule wherein the second nucleic acid molecule is a lentiviral vector that can be transcribed and the transcript assembled into a pseudotyped lentiviral vector particle.

Any of the lentiviral vector particles can be used in a method of treatment of a human or animal subject. The treatment can be a vaccine for immunization, in which the vaccine is prophylactic or therapeutic. A vaccine comprises the lentiviral vector particle with a pharmaceutically acceptable excipient. Alternatively, lentiviral vector particles can be administered to cells in vitro, comprising mixing the cells with any of the lentiviral vector particles above.

These and other aspects of the present invention will become evident upon reference to the following detailed description and attached drawings.

BRIEF DESCRIPTION OF THE DRAWINGS

FIG. 5B presents sequences of the U3 region of three vector constructs. (A) The elements contained in all lentivirus vectors are shown in the exemplary vector genome at the top. Promoters utilized include the human Ubiquitin-C promoter (UbiC), the cytomegalovirus immediate early promoter (CMV), or the Rous sarcoma virus (RSV) promoter. In addition to the standard SIN U3 region, a series of extended deletions are shown. Sequence alignments of the U3 regions from all 3 vectors are shown in (B). The sequence shown includes the polypurine tract (PPT), which is deleted in construct 704, and the extended U3 deletion present in both 703 and 704 constructs.

FIGS. 6A and 6B show GFP expression from lentivirus vector following transduction of 293T cells. In FIG. 6A, GFP was operatively linked to a UbiC promoter, and in FIG. 6B, GFP was operatively linked to a CMV promoter. GFP expression levels were determined from integrase deficient lentivirus vectors 48 hr following transduction of 293T cells expressing DC-SIGN. GFP expression in transduced cells was determined by standard flow cytometric methods; a total of 50,000 events were collected from each tranduced cell pool to determine mean expression levels.

Figure 1A:
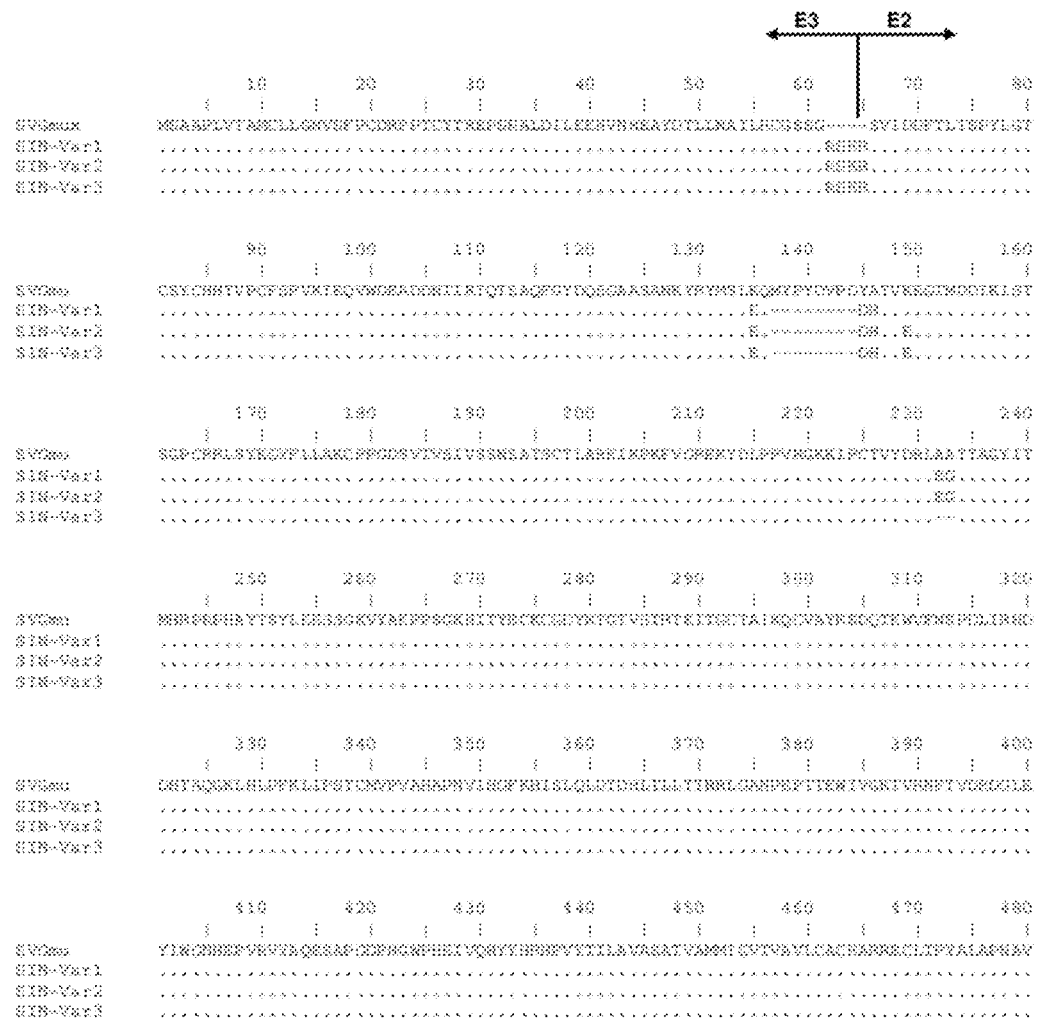
FIG. 1 is a sequence alignment of the envelope protein for four Sindbis virus envelopes, SVGmu, SIN-Var1, SIN-Var2, and SIN-Var3. The alignment is shown relative to SVGmu, a previously described Sindbis envelope. Main differences to SVGmu include the regeneration of the furin like protease cleavage site (RSKR; SEQ ID NO: 27) between E3 and E2, removal of the HA epitope tag, and a series of lysine substitutions to reduce heparin binding.

The envelope of Sindbis virus and other alphaviruses incorporates into the lipid bilayer of the viral particle membrane, and typically includes multiple copies of two glycoproteins, E1 and E2. Each glycoprotein has membrane-spanning regions; E2 has an about 33 residue cytoplasmic domain whereas the cytoplasmic tail of E1 is very short (about 2 residues). Both E1 and E2 have palmitic acids attached in or near the membrane-spanning regions. E2 is initially synthesized as a precursor protein that is cleaved by furin or other Ca2+-dependent serine proteinase into E2 and a small glycoprotein called E3. Located between sequences encoding E2 and E1 is a sequence encoding a protein called 6K. E3 and 6K are signal sequences which serve to translocate the E2 and E1 glycoproteins, respectively, into the membrane. In the Sindbis virus genome, the coding region for Sindbis envelope proteins includes sequence encoding E3, E2, 6K, and E1. As used herein, "envelope" of an arbovirus virus includes at least E2, and may also include E1, 6K and E3. An exemplary sequence of envelope glycoproteins of Sindbis virus, strain HR, is presented as SEQ ID NO: 17. Sequences of envelope glycoproteins for other arboviruses can be found in e.g., GenBank. For example, sequence encoding Dengue virus glycoproteins can be found in Accession GQ252677 (among others in GenBank) and in the virus variation database at NCBI (GenBank accessions and virus variation database are incorporated by reference for envelope glycoprotein sequences) and sequence encoding Venezuelan equine encephalitis virus envelope glycoproteins in Accession NP 040824 (incorporated by reference for sequences of envelope glycoproteins).

Although the cellular receptor(s) on dendritic cells for alphaviruses, and Sindbis virus in particular, have not been definitively identified to date, one receptor appears to be DC-SIGN (Klimstra et al., J Virol 77: 12022, 2003). The use of the terms "attachment", "binding", "targeting" and the like are used interchangeably and are not meant to indicate a mechanism of the interaction between Sindbis virus envelope glycoprotein and a cellular component. DC-SIGN (Dendritic Cell Specific ICAM-3 (Intracellular Adhesion Molecules 3)-Grabbing Nonintegrin; also known as CD209) is a C-type lectin-like receptor capable of rapid binding and endocytosis of materials (Geijtenbeek, T. B., et al. Annu. Rev. Immunol. 22: 33-54, 2004). E2 appears to target virus to dendritic cells through DC-SIGN. As shown herein, cells expressing DC-SIGN are transduced by viral vector particles pseudotyped with Sindbis virus E2 better (at least 2-fold, at least 3-fold, at least 4-fold, at least 5-fold, at least 6-fold, at least 7-fold, at least 8-fold, at least 9-fold, or at least 10-fold better) than isogenic cells that don't express DC-SIGN. The mechanism of how E2 glycoprotein facilitates viral infection appears to involve DC-SIGN, possibly through direct binding to DC-SIGN or causing a change in conformation or some other mechanism. Regardless of the actual mechanism, the targeting by E2 is preferential for cells expressing DC-SIGN, namely dendritic cells.

Sindbis virus also appears to bind to cells via heparan sulfate (Klimstra et al., J Virol 72: 7357, 1998; Burmes and Griffin, J Virol 72: 7349, 1998). Because heparan sulfate and other cell surface glycosaminoglycans are found on the surface of most cell types, it is desirable to reduce interaction between heparan sulfate and Sindbis envelope glycoproteins. This can be accomplished by diminishing the binding of Sindbis virus envelope to heparan sulfate or increasing the binding, e.g., increasing avidity, of Sindbis virus envelope to dendritic cells or both. As a result, nonspecific binding to other molecules, which may be expressed by other cell types and which may occur even if the envelope is specific for DC-SIGN, is reduced, and the improved specificity may serve to avoid undesired side effects, such as side effects that may reduce the desired immune response, or side effects associated with off-target transduction of other cell types. Alternatively or in addition to the advantages of relatively specific transduction of cells expressing DC-SIGN, viral particles pseudo-typed with Sindbis virus envelope E2 glycoprotein may offer other advantages over viral particles pseudo-typed with glycoproteins such as VSVG. Examples of such advantages include reduced complement-mediated lysis and/or reduced neuronal cell targeting, both of which are believed to associate with administration of VSV-G pseudo-typed viral particles.

In various exemplifications, the lentiviral vector particles specifically bind to cells expressing DC-SIGN and have reduced or abrogated binding to heparan sulfate. That is, a Sindbis virus envelope E2 glycoprotein may be modified to preferentially direct the virus to dendritic cells that express DC-SIGN relative to other cell types. Based on information obtained from structural studies and molecular modeling among other studies, variant sequences of envelope proteins, especially E2 and E1 glycoproteins, are designed and generated such that the glycoproteins maintain their functions as envelope proteins, but have the desired binding specificity, avidity, or level of binding. Candidate variant sequences may be created for each glycoprotein and assayed using the methods described below, or other methods known in the art, to identify envelope glycoproteins with the most desirable characteristics.

Certain variant sequences of Sindbis E2 have at least one amino acid alteration at residue 160 as compared to SEQ ID NO: 1. Residue 160 is deleted or changed to an amino acid other than glutamic acid. An alteration is most commonly a substitution of at least one amino acid, but alternatively can be an addition or deletion of one or more amino acids. Preferably, any additional amino acids are few in number and do not comprise an antigenic epitope (e.g., hemagglutinin tag sequence), which may compromise safety. When there are two or more alterations, they can both be of the same type (e.g., substitution) or differing types (e.g., a substitution and a deletion). Multiple alterations can be scattered or located contiguously in the protein sequence.

In the first instance, variant sequences comprise at least one amino acid alteration in the region of about residue 50 to about residue 180. Within this region are amino acids that are involved with binding to heparan sulfate. By reducing the net positive charge of E2, electrostatic interaction with heparan sulfate can be reduced, resulting in decreased binding to heparan sulfate. Candidate positively charged amino acids in this region include lysines at residues 63, 70, 76, 84, 97, 104, 129, 131, 133, 139, 148, 149, 159 and arginine at residues 65, 92, 128, 137, 157, 170, 172 (Bear et al., Virology 347: 183-19(1 2006). At least several of these amino acids are directly implicated in E2 binding to heparan sulfate. Net positive charge can be reduced by deletion of lysine or arginine or substitution of lysine or arginine with a neutral or negatively charged amino acid. For example, one or more of these lysines and arginines may be replaced with glutamic or aspartic acid. Certain embodiments have at least one substitution of lysine 70, 76 or 159. In cases where E2 is expressed as a polyprotein with E3, the lysine located adjacent to the natural E3/E2 cleavage site is maintained—that is, the recognition sequence and cleavage site is unaltered. Alternatively, the native endopeptidase cleavage site sequence is replaced with a recognition sequence for a different endopeptidase.

Certain variants of E2 are also modified in a way that positively impacts binding to dendritic cells. Alteration of the glutamic acid found at residue 160 in the reference HR sequence can improve binding to dendritic cells (see Gardner et al., J Virol 74, 11849, 2000, which is incorporated in its entirety). Alterations, such as a deletion of residue 160 or substitution of residue 160 are found in certain variants. In particular variants, a non-charged amino acid is substituted for Glu, in other variants, a non-acidic amino acid is substituted for Glu. Typically, Glu160 is replaced with one of the small or aliphatic amino acids, including glycine, alanine, valine, leucine or isoleucine.

Other variants comprise two or more amino acid alterations. Typically in these variants one of the alterations is Glu160 and the remaining alteration(s) are changes of one or more of the lysines and arginines in the region spanning residue about 50 to about 180. Certain of the variants comprise an alteration of Glu160 to a non-acidic residue or deletion and one or more alterations of lysine 70, lysine 76, or lysine 159 with a non-basic amino acid. Some specific variants comprise a Glu160 to Gly, Lys 70 to Glu, and Lys 159 to Glu; a Glu 160 to Gly, Lys 70, 76 and 159 to Glu; a deletion of Glu 160 and Lys 70 and 159 to Glu; and a deletion of Glu 160 and Lys 70, 76, and 159 to Glu.

In certain cases. E2 protein is first expressed as a polyprotein in fusion with at least E3 or in fusion with a leader sequence. Regardless of whether the leader sequence is E3 or another sequence, E2 in the viral envelope should be free of the E3 or other leader sequence. In other words, E2 is preferably not an E3/E2 fusion protein (e.g., the E3/E2 fusion protein called SVGmu). In certain embodiments, E2 is expressed as part of E3-E2-6K-E1 polyprotein. Sindbis virus naturally expresses E2 as part of a polyprotein and the junction regions for E3/E2. E2/6K, and 6K/E1 have sequences recognized and cleaved by endopeptidases. Normally, the E3/E2 junction is cleaved by furin or a furin-like serine endopeptidase between residues 65 and 66. Furin has specificity for paired arginine residues that are separated by two amino acids. To maintain E3/E2 cleavage by furin, residues 62-66 (RSKRS; SEQ ID NO: 26) should maintain the two arginine residues with two amino acid separation and the serine residue. Alternatively, a different cleavage sequence can be used in place of the E3/E2 furin cleavage sequence or any of the other cleavage sequences. Recognition and cleavage sites can be incorporated for endopeptidases, including, without limitation, aspartic endopeptidases (e.g., cathepsin D. chymosin, HIV protease), cysteine endopeptidases (bromelains, papain, calpain), metalloendopeptidases, (e.g., collagenase, thermolysin), serine endopeptidases (e.g., chymotrypsin, factor IXa, factor X, thrombin, trypsin), streptokinases. The recognition and cleavage site sequences for these enzymes are well known.

Amino acids in E2, other than those already mentioned, may also be altered. Generally, a variant E2 sequence will have at least 80% sequence amino acid identity to the reference E2 sequence, or it may have at least 82%, at least 85%, at least 87%, at least 90%, at least 92%, at least 95%, or at least 98% sequence identity. The variant glycoprotein should exhibit biological function, such as the ability to facilitate infection of dendritic cells by a viral particle having an envelope comprising E2. Experiments have identified regions of envelope glycoproteins that appear to have an important role in various aspects of viral assembly, attachment to cell surface, and infection. When making variants, the following information can be used as guidelines. The cytoplasmic tail of E2—approximately residues 408 to 415—is important for virus assembly (West et al. J Virol 80: 4458-4468, 2006; incorporated in its entirety). Other regions are involved in forming secondary structure (approximately residues 33-53); and involved in transport and protein stability (approximately residues 86-119) (Navaratnnarajah et al., J Virol 363: 124-147, 2007; incorporated in its entirety). The variant may retain hydrophobic character of a region that spans the membrane, approximately residues 370-380. The variant may retain one or both N-linked glycosylation sites residues NIT (residues 196-198) and NFT (residues 318-320) and may retain one or more of the sites that are palmitoylated (C-396. C416 and C417) (Strauss and Strauss Microbiol Rev 58, 491-562, 1994; pp. 499-509 incorporated). On the other hand, many regions of E2 may be altered without deleterious event. For example, insertions of transposons at many different locations in E2 still resulted in viable virus (Navaratmarajah, ibid).

In certain embodiments, a tag peptide may be incorporated into E3, 6K, or E1 proteins. For some purposes, a tag may be incorporated into E2, but a tag is not desirable for use in a product for administration to human patients. A tag peptide, which is a short sequence (e.g., 5-30 amino acids), can be used to facilitate detection of envelope expression and its presence in viral particles. For detection purposes, a tag sequence will typically be detectable by antibodies or chemicals. Another use for a tag is to facilitate purification of viral particles A substrate containing a binding partner for the tag can be used to absorb virus. Elution of the virus can be accomplished by treatment with a moiety that displaces the tag from the binding partner or when the tag sequence is in linkage with a cleavable sequence, treatment with the appropriate endopeptidase will conveniently allow release of virus. (See, for example, Qiagen catalog, Factor Xa Protease System). Removal of the tag peptide is generally desirable for safety purposes of the virus particles use in animal subjects. If the tag is not removed, an immune response to the tag may occur.

Suitable tags include, without limitation, FLAG (DYKD-DDDK) (SEQ ID NO: 28) (U.S. Pat. No. 4,703,004, incorporated in its entirety), for which antibodies are commercially available, chitin binding protein, maltose binding protein, glutathione-S-transferase, poly(His) (U.S. Pat. No. 4,569,794, incorporated in its entirety), thioredoxiin, HA (hemagglutinin)-tag, among others. Poly(His) can be adsorbed onto affinity media containing bound metal ions, e.g., nickel or cobalt, and eluted with a low pH medium.

The viral particles may be evaluated to determine the specificity of the envelope glycoprotein incorporated into the virus that targets dendritic cells. For example, a mixed population of bone marrow cells can be obtained from a subject and cultured in vitro. Alternatively, isogenic cells lines that express or don't express DC-SIGN can be obtained and used. The recombinant virus can be administered to the mixed population of bone marrow cells or isogenic cell lines, and expression of a reporter gene incorporated into the virus can be assayed in the cultured cells. Certain embodiments may employ a limiting dilution analysis, in which the mixed population of cells is split into separate parts, which are then separately incubated with decreasing amounts of virus (e.g., 2-fold, 5-fold, 10-fold less virus in each part). In some embodiments, at least about 50%, more preferably at least about 60%, 70%, 80% or 90%, still more preferably at least about 95% of infected cells in the mixed cell population are dendritic cells that express DC-SIGN. In certain embodiments, the ratio of infected dendritic cells to infected non-dendritic cells (or non DC-SIGN expressing cells) is at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 40:1, at least about 50:1, at least about 100:1, at least about 200:1, at least about 500:1, at least about 1000:1, at least about 5000:1, at least about 10,000:1, or more. For limiting dilution, greater selectivity is typically seen at higher dilutions (i.e., lower amounts) of input virus.

Activity of pseudotyped viral particles can be determined by any of a variety of techniques. For example, a preferred method to measure infectivity efficiency (IU, infectious units) is by administering viral particles to cells and measuring expression of a product encoded in the vector genome. Any product that can be assayed may be used. One convenient type of product is a fluorescent protein, such as green fluorescent protein (GFP). GFP and assay is exemplified in the Examples, such as Example 3. Other products that can be used include proteins expressed on a cell surface (e.g., detection by antibody binding), enzymes, and the like. If the product is an antigen and cells are dendritic cells, infectivity/activity can be assessed by determining an immune response. Furthermore, it is possible to ascertain side effects in a mammal. The ability to specifically target dendritic cells can also be tested directly, for example, in cell culture as described below.

Viral particles can also be prepared and tested for their selectivity and/or their ability to facilitate penetration of the target cell membrane. Viral particles that have an envelope with unmodified glycoproteins can be used as controls for comparison. Briefly, cells expressing a receptor for an envelope glycoprotein are infected by the virus using a standard infection assay. After a specified time, for example 48 hours post-infection, cells can be collected and the percentage of cells infected by the virus can be determined by flow cytometry, for example. Selectivity can be scored by calculating the percentage of cells infected by virus. Similarly, the effect of a variant envelope glycoprotein on viral titer can be quantified by dividing the percentage of cells infected by virus comprising a variant envelope by the percentage of cells infected by virus comprising the corresponding wild type (unmodified) envelope glycoprotein. A particularly suitable variant will have the best combination of selectivity and infectious titer. Once a variant is selected, viral concentration assays may be performed to confirm that these viruses can be concentrated without compromising activity. Viral supernatants are collected and concentrated by ultracentrifugation. The titers of viruses can be determined by limited dilution of viral stock solution and infection of cells expressing the receptor for the envelope glycoprotein, measuring the expression of a product expressed by the viruses as described above.

The entry of a lentiviral vector particle into a target cell is another type of evaluation of activity. BlaM-Vpr (beta-lactamase Vpr) fusion protein has been utilized to evaluate HIV-1 viral penetration; a fusion of BlaM and a Sindbis virus envelope glycoprotein, such as E1 or an E2/E1 fusion protein can be used to assess the efficacy of an envelope protein in facilitating fusion and penetration into a target cell. Viral particles may be prepared, for example, by transient transfection of packaging cells with one or more vectors comprising the viral elements. BlaM-Vpr, and the variant envelope of interest (and an affinity molecule if appropriate). The resulting viruses can be used to infect cells expressing a molecule the targeting molecule (or affinity molecule) specifically binds in the absence or presence of the free inhibitor of binding (such as an antibody). Cells can then be washed with $CO_2$-independent medium and loaded with CCF2 dye (Aurora Bioscience). After incubation at room temperature to allow completion of the cleavage reaction, the cells can be fixed by paraformaldehyde and analyzed by flow cytometry and microscopy. The presence of blue cells indicates the penetration of viruses into the cytoplasm; fewer blue cells would be expected when blocking antibody is added (Cavrois et al. Nat Biotechnol 20: 1151-1154, 2002; incorporated in its entirety).

To investigate whether penetration is dependent upon a low pH, and to identify envelope glycoproteins with the desired pH dependence. $NH_4Cl$ or other compound that alters pH can be added at the infection step ($NH_4Cl$ will neutralize the acidic compartments of endosomes). In the case of $NH_4Cl$, the disappearance of blue cells will indicate that penetration of viruses is low pH-dependent. In addition, to confirm that the activity is pH-dependent, lysosomotropic agents, such as ammonium chloride, chloroquine, concanamycin, bafilomycin Al, monensin, nigericin, etc., may be added into the incubation buffer. These agents elevate the pH within the endosomal compartments (e.g., Drose and Altendorf, J. Exp. Biol. 200, 1-8, 1997). The inhibitory effect of these agents will reveal the role of pH for viral fusion and entry. The different entry kinetics between viruses displaying different fusogenic molecules may be compared and the most suitable selected for a particular application.

PCR-based entry assays can be utilized to monitor reverse transcription and measure kinetics of viral DNA synthesis as an indication of the kinetics of viral entry. For example, viral particles comprising a particular envelope protein molecule are incubated with target cells, such as 293T cells, DCs, or any other cells that have been engineered to express, or which naturally express, the appropriate binding partner (receptor) for the envelope protein molecule. Either immediately, or after a time increment (to allow infection to occur), unbound viruses are removed and aliquots of the cells are analyzed for viral nucleic acids. DNA is extracted from these aliquots and subjected to amplification analysis, generally in a semi-quantitative assay, primed with LTR-specific primers. The appearance of LTR-specific DNA products indicates the success of viral entry.

B. Lentiviral Vector Genome

The viral vector particle comprises a genome, which comprises the sequence(s) of interest. Other sequences may included, such as sequences that allow the genome to be packaged into the virus particle and sequences that promote expression of the sequence(s) of interest following transduction of the target cell. The genome can be derived from any of a large number of suitable, available lentiviral genome based vectors, including those identified for human gene therapy applications, such as those described by Pfeifer and Verma (Annu. Rev. Genomics Hum. Genet. 2:177-211, 2001; which is incorporated herein by reference in its entirety). For the sake of simplicity, the genome is also referred to as "viral vector genome" or "vector genome".

1. Backbone

Suitable lentiviral vector genomes include those based on Human Immunodeficiency Virus (HIV-1), HIV-2, feline immunodeficiency virus (FIV), equine infectious anemia virus, Simian Immunodeficiency Virus (SIV) and maedi/visna virus. A desirable characteristic of lentiviruses is that they are able to infect both dividing and non-dividing cells, it is not necessary for target cells to be dividing (or to stimulate the target cells to divide). Generally, the genome and envelope glycoproteins will be based on different viruses, such that the resulting viral vector particle is pseudotyped. Safety features of the vector genome are desirably incorporated. Safety features include self-inactivating LTR and a non-integrating genome. Exemplary vectors are discussed further in Example 5 and FIG. 5 and such vectors may be used in embodiments of the invention for expression of antigens of interest.

In some exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Typically, the LTR sequences are HIV LTR sequences.

The vector genome may comprise an inactivated or self-inactivating 3' LTR (Zufferey et al. J Virol 72: 9873, 1998; Miyoshi et al., J Virol 72:8150, 1998; both of which are incorporated in their entirety). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the TATA box, Sp1 and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art.

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (U.S. Pat. No. 5,385,839 and U.S. Pat. No. 5,168,062, each of which is incorporated in its entirety).

In certain embodiments, the risk of insertional mutagenesis is minimized by constructing the lentiviral vector genome to be integration defective. A variety of approaches can be pursued to produce a non-integrating vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

As stated above, one approach is to make and use a non-functional integrase. Integrase is involved in cleavage of viral double-stranded blunt-ended DNA and joining the ends to 5'-phosphates in the two strands of a chromosomal target site. Integrase has three functional domains: N-terminal domain, which contains a zinc-binding motif (HHCC), the central domain core, which contains the catalytic core and a conserved DD35E motif (D64, D116, E152 in HIV-1), and a C-terminal domain, which has DNA binding properties. Point mutations introduced into integrase are sufficient to disrupt normal function. Many integrase mutations have been constructed and characterized (see, Philpott and Thrasher, Human Gene Therapy 18:483, 2007; Apolonia, Thesis submitted to University College London, April 2009, pp, 82-97; Engelman et al. J Virol 69: 2729, 1995; Nightingale et al. Mol Therapy, 13: 1121, 2006; all of which are incorporated in their entirety). The sequence encoding the integrase protein can be deleted or mutated to render the protein inactive, preferably without significantly impairing reverse transcriptase activity or nuclear targeting, thereby only preventing integration of the provirus into the target cell genome. Acceptable mutations can reduce integrase catalysis, strand transfer, binding to att sites, binding to host chromosomal DNA, and other functions. For example, a single aspartic acid to asparagine substitution at residue 35 of HIV or SIV integrase completely abolishes viral DNA integration. Deletions of integrase will generally be confined to the C-terminal domain. Deletion of coding sequence for residues 235-288 result in a useful non-functional integrase (Engelman et al. J Viral 69:2729, 1995). As further examples, mutations can be generated, for example, Asp64 (residue numbers are given for HIV-1, corresponding residue numbers for integrase from other lentiviruses or retroviruses can be readily determined by one of ordinary skill) (e.g., D64E, D64V), Asp116 (e.g., D116N), Asn120 (e.g., N120K), Glu152, Gln148 (e.g., Q148A), Lys156, Lys159, Trp235 (e.g. W235E), Lys264 (e.g., K264R), Lys266 (e.g., K266R), Lys273 (e.g., K273R). Other mutations can be constructed and tested for integration, transgene expression, and any other desirable parameter. Assays for these functions are well known. Mutations can be generated by any of a variety of techniques, including site-directed mutagenesis and chemical synthesis of nucleic acid sequence. One mutation may be made or more than one of these mutations can be present in integrase. For example, an integrase may have mutations at two amino acids, three amino acids, four amino acids, and so on.

Alternatively or in combination with the use of integrase mutant(s), the attachment sites (att) in U3 and U5 can also be mutated. Integrase binds to these sites and the 3'-terminal dinucleotide is cleaved at both ends of the vector genome. A CA dinucleotide is located at the recessed 3' end; the CA is required for processing, mutation of the nucleotides blocks integration into the host chromosome. The A of the CA dinucleotide is the most critical nucleotide for integration, and mutations at both ends of the genome will give the best results (Brown et al J Virol 73:9011 (1999). In one exemplification, the CA at each end is changed to TG. In other exemplifications, the CA at each end is changed to TG at one and and GT at the other end. In other exemplifications, the CA at each end is deleted; in other exemplifications, the A of the CA is deleted at each end.

Integration can also be inhibited by mutation or deletion of polypurine tract (PPT) (WO 2009/076524; incorporated in its entirety), located proximally to the 3' LTR. The PPT is a polypurine sequence of about 15 nucleotides that can serve as a primer binding site for plus-strand DNA synthesis. In this case, mutations or deletions of PPT targets the reverse transcription process. Without wishing to be held to a mechanism, by mutating or deleting PPT, production of linear DNA is radically reduced and essentially only 1-LTR DNA circles are produced. Integration requires a linear double-stranded DNA vector genome, and integration is essentially eliminated without it. As stated above, a PPT can be made non-functional by mutation or by deletion. Typically, the entire about 15 nt PPT is deleted, although in some embodiments, shorter deletions of 14 nt, 13, nt, 12 nt, 11 nt, 10 nt, 9 nt, 8 nt, 7 nt, 6 nt, 5 nt, 4 nt, 3 nt and 2 nt may be made. When mutations are made, typically multiple mutations are made, especially in the 5' half of the PPT (McWilliams et al., J Virol 77:11150, 2003), although single and double mutations in the first four bases still reduce transcription. Mutations made at the 3' end of PPT generally have a more dramatic effect (Powell and Levin J Virol 70:5288, 1996).

These different approaches to make a vector genome non-integrating can be used individually or in combination. Using more than one approach may be used to build a fail-safe vector through redundant mechanisms. Thus. PPT mutations or deletions can be combined with att site mutations or deletions or with Integrase mutations or PPT mutations or deletions can be combined with both att site mutations or deletions and Integrase mutations. Similarly, att site mutations or deletions and Integrase mutations may be combined with each other or with PPT mutations or deletions.

2. Regulatory Elements

As discussed herein, the viral vector genome comprises a sequence of interest that is desirable to express in target cells. Typically, the sequence of interest is located between the 5' LTR and 3' LTR sequences. Further, the sequence of interest is preferably in a functional relationship with other genetic elements, for example transcription regulatory sequences including promoters or enhancers, to regulate expression of the sequence of interest in a particular manner. In certain instances, the useful transcriptional regulatory sequences are those that are highly regulated with respect to activity, both temporally and spatially. Expression control elements that may be used for regulating the expression of the components are known in the art and include, but are not limited to, inducible promoters, constitutive promoters, secretion signals, enhancers and other regulatory elements.

The sequence of interest and any other expressible sequence is typically in a functional relationship with internal promoter/enhancer regulatory sequences. An "internal" promoter/enhancer is one that is located between the 5' LTR and the 3' LTR sequences in the viral vector construct and is operably linked to the sequence of interest. The internal promoter/enhancer may be any promoter, enhancer or promoter/enhancer combination known to increase expression of a gene with which it is in a functional relationship. A "functional relationship" and "operably linked" mean, without limitation, that the sequence is in the correct location and orientation with respect to the promoter and/or enhancer that the sequence of interest will be expressed when the promoter and/or enhancer is contacted with the appropriate molecules.

The choice of an internal promoter/enhancer is based on the desired expression pattern of the sequence of interest and the specific properties of known promoters/enhancers. Thus, the internal promoter may be constitutively active. Non-limiting examples of constitutive promoters that may be used include the promoter for ubiquitin (U.S. Pat. No. 5,510,474; WO 98/32869, each of which is incorporated herein by reference in its entirety), CMV (Thomsen et al., PNAS 81:659, 1984; U.S. Pat. No. 5,168,062, each of which is incorporated herein by reference in its entirety), beta-actin (Gunning et al. 1989 Proc. Natl. Acad. Sci. USA 84:4831-4835, which is incorporated herein by reference in its entirety) and pgk (see, for example, Adra et al. 1987 Gene 60:65-74; Singer-Sam et al. 1984 Gene 32:409-417; and Dobson et al. 1982 Nucleic Acids Res. 10:2635-2637, each of the foregoing which is incorporated herein by reference in its entirety).

Alternatively, the promoter may be a tissue specific promoter. In some preferred embodiments, the promoter is a target cell-specific promoter. For example, the promoter can be from any product expressed by dendritic cells, including CD11c, CD103, TLRs, DC-SIGN, BDCA-3, DEC-205, DCIR2, mannose receptor, Dectin-1, Clec9A, MHC classII. In addition, promoters may be selected to allow for inducible expression of the sequence of interest. A number of systems for inducible expression are known in the art, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. A combination of promoters may also be used to obtain the desired expression of the gene of interest. The artisan of ordinary skill will be able to select a promoter based on the desired expression pattern of the gene in the organism or the target cell of interest.

The viral genome may comprise at least one RNA Polymerase II or III responsive promoter. This promoter can be operably linked to the sequence of interest and can also be linked to a termination sequence. In addition, more than one RNA Polymerase II or III promoters may be incorporated. RNA polymerase II and III promoters are well known to one of skill in the art. A suitable range of RNA polymerase III promoters can be found, for example, in Paule and White. Nucleic Acids Research., Vol. 28, pp 1283-1298 (2000), which is incorporated herein by reference in its entirety. RNA polymerase II or III promoters also include any synthetic or engineered DNA fragment that can direct RNA polymerase II or III to transcribe downstream RNA coding sequences. Further, the RNA polymerase II or III (Pol II or III) promoter or promoters used as part of the viral vector genome can be inducible. Any suitable inducible Pol II or III promoter can be used with the methods of the invention. Particularly suited Pol II or III promoters include the tetracycline responsive promoters provided in Ohkawa and Taira, Human Gepe Therapy, Vol. 11, pp 577-585 (2000) and in Meissner et al. Nucleic Acids Research, Vol. 29, pp 1672-1682 (2001), each of which is incorporated herein by reference in its entirety.

An internal enhancer may also be present in the viral construct to increase expression of the gene of interest. For example, the CMV enhancer (Boshart et al. Cell, 41:521, 1985: which is incorporated herein by reference in its entirety may be used. Many enhancers in viral genomes, such as HIV. CMV, and in mammalian genomes have been identified and characterized (see GenBank). An enhancer can be used in combination with a heterologous promoter. One of ordinary skill in the art will be able to select the appropriate enhancer based on the desired expression pattern.

A viral vector genome will usually contain a promoter that is recognized by the target cell and that is operably linked to the sequence of interest, viral components, and other sequences discussed herein. A promoter is an expression control element formed by a nucleic acid sequence that permits binding of RNA polymerase and transcription to occur. Promoters may be inducible, constitutive, temporally active or tissue specific. The activity of inducible promoters is induced by the presence or absence of biotic or abiotic factors. Inducible promoters can be a useful tool in genetic engineering because the expression of genes to which they are operably linked can be turned on or off at certain stages of development of an organism, its manufacture, or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are described elsewhere, for example, in "Promoters used to regulate gene expression" on Patent Lens web site, accessed 18 May 2009 (incorporated herein by reference in its entirety).

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. Heterologous promoters are preferred, however, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

The viral vector genome may also contain additional genetic elements. The types of elements that may be included in the construct are not limited in any way and may be chosen to achieve a particular result. For example, a signal that facilitates nuclear entry of the viral genome in the target cell may be included. An example of such a signal is the HIV-1 flap signal. Further, elements may be included that facilitate the characterization of the provirus integration site in the target cell. For example, a tRNA amber suppressor sequence may be included in the construct. An insulator sequence from e.g.,
chicken β-globin may also be included in the viral genome construct. This element reduces the chance of silencing an integrated provirus in the target cell due to methylation and heterochromatinization effects. In addition, the insulator may shield the internal enhancer, promoter and exogenous gene from positive or negative positional effects from surrounding DNA at the integration site on the chromosome. In addition, the vector genome may contain one or more genetic elements designed to enhance expression of the gene of interest. For example, a woodchuck hepatitis virus responsive element (WRE) may be placed into the construct (Zufferey et al. 1999. J. Virol. 74:3668-3681; Deglon et al. 2000. Hum. Gene Ther. 11:179-190, each of which is incorporated herein by reference in its entirety).

The viral vector genome is typically constructed in a plasmid form that may be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline.

Plasmids containing one or more of the components described herein are readily constructed using standard techniques well known in the art. For analysis to confirm correct sequences in plasmids constructed, the plasmid may be replicated in *E. coli*, purified, and analyzed by restriction endonuclease digestion or its DNA sequence determined by conventional methods.

Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. See Sambrook et al., supra, pp. 16.17-16.22. Other vectors and methods suitable for adaptation to the expression of polypeptides are well known in the art and are readily adapted to the specific circumstances.

Using the teachings provided herein, one of skill in the art will recognize that the efficacy of a particular expression system can be tested by transfecting packaging cells with a vector comprising a gene encoding a reporter protein and measuring the expression using a suitable technique, for example, measuring fluorescence from a green fluorescent protein conjugate. Suitable reporter genes are well known in the art.

3. Types of Sequences of Interest

The sequence of interest is not limited in any way and includes any nucleic acid that one of ordinary skill desires to have integrated, transcribed, and expressed in the target cell. The product can be a protein or a nucleic acid. The sequence of interest can encode a protein or a nucleic acid molecule, including siRNA, microRNA, a self-complementary double stranded RNA in which the complementary region is greater than about 20 ribonucleotides in length, or an RNA that is complementary to a message RNA, where binding of said complementary (anti-sense) RNA to the message RNA blocks its ability to be translated into protein. In some instances, the sequence of interest can encode an antigen against which an immune response is desired. In particular, tumor antigens and infectious diseases antigens from agents such as HIV, HSV, HCV, HPV, malaria, or tuberculosis are desirable.

In certain cases, the sequence of interest can be a gene encoding a small inhibiting RNA (siRNA) or a microRNA (miRNA) of interest that down-regulates expression of a molecule. For example, the gene encoding an siRNA or a microRNA can be used to down-regulate expression of negative regulators in a cell, including those that inhibit activation or maturation of dendritic cells. siRNAs and microRNAs are well known in the art (Fire et al., Nature 391:806, 1998; see also "The RNA Interference Resource" of Applied Biosystems, Trang et al., Oncogene Suppl 2:S52, 2008; Taganov, K., et al. 2007. Immunity 26:133-137; Dahlberg, J. E. and E. Lund. 2007. Sci. STKE 387:pe25; Tiemann and Rossi, EMBO Mol Med 1: 142, 2009). Alternatively, the sequence of interest can encode a self-complementary double stranded RNA in which the complementary region is greater than about 20 ribonucleotides in length, or an anti-sense RNA that is greater than about 20 ribonucleotides in length. Those of ordinary skill in the art will appreciate that siRNA, miRNA, dsRNA and anti-sense RNA molecules can be expressed from an RNA polymerase III promoter, or, alternatively, can be a component of a non-coding RNA that is transcribed from an RNA polymerase II promoter.

In addition, the sequence of interest may encode more than one product. In some configurations, the sequence to be delivered can comprise multiple genes encoding at least one protein, at least one siRNA, at least one microRNA, at least one dsRNA or at least one anti-sense RNA molecule or any combinations thereof. For example, the sequence to be delivered can include one or more genes that encode one or more antigens against which an immune response is desired. The one or more antigens can be associated with a single disease or disorder, or they can be associated with multiple diseases and/or disorders. In some instances, a gene encoding an immune regulatory protein can be included along with a gene encoding an antigen against which an immune response is desired, and the combination can elicit and regulate the immune response to the desired direction and magnitude. In other instances, a sequence encoding an siRNA, microRNA, dsRNA or anti-sense RNA molecule can be constructed with a gene encoding an antigen against which an immune response is desired, and the combination can regulate the scope of the immune response. The products may be produced as an initial fusion product in which the encoding sequence is in functional relationship with one promoter. Alternatively, the products may be separately encoded and each encoding sequence in functional relationship with a promoter. The promoters may be the same or different.

In certain configurations, vectors contain polynucleotide sequences that encode dendritic cell maturation/stimulatory factors. Exemplary stimulatory molecules include GM-CSF, IL-2, IL-4, IL-6, IL-7, IL-15, IL-21, IL-23, TNFα, B7.1, B7.2, 4-1BB, CD40 ligand (CD40L), drug-inducible CD40 (iCD40), and the like. These polynucleotides are typically under the control of one or more regulatory elements that direct the expression of the coding sequences in dendritic cells. Maturation of dendritic cells contributes to successful vaccination (Banchereau. J and Palucka, A. K. Nat. Rev. Immunol. 5:296-306 (2005); Schuler, G. et al. Curr. Opin. Immunol. 15:138-147 (200; Figdor, C. G. et al. Nat. Med. 10:475-480 (2004). Maturation can transform DCs from cells actively involved in antigen capture into cells specialized for T cell priming. For example, engagement Of CD40 by CD40L on CD4-helper T cells is a critical signal for DC maturation, resulting in potent activation of CD8 T cells. Such stimulatory molecules are also referred to as maturation factors or maturation stimulatory factors. Immune checkpoints represent significant barriers to activation of functional cellular immunity in cancer, and antagonistic antibodies specific for inhibitory ligands on T cells including CTLA4 and programmed death-1 (PD-1) are examples of targeted agents being evaluated in the clinics. A significant tolerance mechanism in chronic infections and cancer is the functional exhaustion of Ag-specific T cells that express high levels of PD-1. As the potency of therapeutic immunization has been shown to be significantly enhanced by combination with immune checkpoint control, as a non-limiting example, it can be appreciated by those of ordinary skill in the art that an alternative approach to inhibiting immune checkpoint is to inhibit the expression of programmed death (PD) ligands one and two (PD-L1/L2). One way to accomplish inhibition is by the expression of RNA molecules such as those described herein, which repress the expression of PD-L1/L2 in the DCs transduced with the lentivirus vector encoding one or more of the RNA molecules. Maturation of DCs or expression of particular elements such as immune checkpoints, for example PD-1 ligands, can be characterized by flow cytometry analysis of up-regulation of surface marker such as MHC II, and profile of expressed chemokines and cytokines.

A sequence encoding a detectable product, usually a protein, can be included to allow for identification of cells that are expressing the desired product. For example, a fluorescent marker protein, such as green fluorescent protein (GFP), is incorporated into the construct along with a sequence of interest (e.g., encoding an antigen). In other cases, the protein may be detectable by an antibody or the protein may be an enzyme that acts on a substrate to yield a detectable product, or a product that allows selection of a transfected or transduced target cell, for example confers drug resistance, such as hygromycin resistance. Typical selection genes encode proteins that confer resistance to antibiotics or other toxins suitable for use in eukaryotic cells, e.g., neomycin, methotrexate, blasticidine, among others known in the art, or complement auxotrophic deficiencies, or supply critical nutrients withheld from the media. The selectable marker can optionally be present on a separate plasmid and introduced by co-transfection.

One or more multicistronic expression units may be utilized that include two or more of the elements (e.g., sequence(s) of interest, the envelope molecule. DC maturation factors) necessary for production of the desired virus in packaging cells. The use of multicistronic vectors reduces the total number of nucleic acid molecules required and thus avoids the possible difficulties associated with coordinating expression from multiple vector genomes. In a multicistronic vector the various elements to be expressed are operably linked to one or more promoters (and other expression control elements as necessary). In some configurations, a multicistronic vector comprises a sequence of interest, a sequence encoding a reporter product, and viral elements. The sequence of interest typically encodes an antigen and, optionally, a DC maturation factor. At times, the multicistronic vector comprises a gene encoding an antigen, a gene encoding a DC maturation factor and viral elements.

Each component to be expressed in a multicistronic expression vector may be separated, for example, by an internal ribosome entry site (IRES) element or a viral 2A element, to allow for separate expression of the various proteins from the same promoter. IRES elements and 2A elements are known in the art (U.S. Pat. No. 4,937,190; de Felipe et al. 2004. Traffic 5: 616-626, each of which is incorporated herein by reference in its entirety). In one embodiment, oligonucleotides encoding furin cleavage site sequences (RAKR) (Fang et al. 2005. Nat. Biotech 23: 584-590, which is incorporated herein by reference in its entirety) linked with 2A-like sequences from foot-and-mouth diseases virus (FMDV), equine rhinitis A virus (ERAV), and thosea asigna virus (TaV) (Szymczak et al. 2004. Nat. Biotechnol. 22: 589-594, which is incorporated herein by reference in its entirety) are used to separate genetic elements in a multicistronic vector. The efficacy of a particular multicistronic vector can readily be tested by detecting expression of each of the genes using standard protocols.

In a specific exemplification, the viral vector genome comprises: a cytomegalovirus (CMV) enhancer/promoter sequence; the R and U5 sequences from the HIV 5' LTR; a packaging sequence (ψ); the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR. In some exemplifications, the vector genome comprises an intact lentiviral 5' LTR and a self-inactivating 3' LTR. (Iwakuma et al. Virology 15:120, 1999, incorporated by reference in its entirety)

Construction of the vector genome can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989. Molecular Cloning: A Laboratory Manual. Cold Spring Harbor Laboratory Press, N.Y.), Coffin et al. (Retroviruses. Cold Spring Harbor Laboratory Press, N.Y. (1997)) and "RNA Viruses: A Practical Approach" (Alan J. Cann, Ed., Oxford University Press, (2000), each of the foregoing which is incorporated herein by reference in its entirety.

4. Production of Viral Particles

Any of a variety of methods already known in the art may be used to produce infectious lentiviral particles whose genome comprises an RNA copy of the viral vector genome. In one method, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences of interest. In order to prevent replication of the genome in the target cell, however, endogenous viral genes required for replication will usually be removed and provided separately in the packaging cell line.

In general, the lentiviral vector particles are produced by a cell line that is transfected with one or more plasmid vectors containing the components necessary to generate the particles. These lentiviral vector particles are typically not replication-competent, i.e., they are only capable of a single round of infection. Most often, multiple plasmid vectors are utilized to separate the various genetic components that generate the lentiviral vector particles, mainly to reduce the chance of recombination events that might otherwise generate replication competent viruses. A single plasmid vector having all of the lentiviral components can be used if desired, however. As one example of a system that employs multiple plasmid vectors, a cell line is transfected with at least one plasmid containing the viral vector genome (i.e., the vector genome plasmid), including the LTRs, the cis-acting packaging sequence, and the sequence(s) of interest, which are often operably linked to a heterologous promoter, at least one plasmid encoding the virus enzymatic and structural components (i.e., the packaging plasmid that encodes components such as. Gag and Pol), and at least one envelope plasmid encoding an Arbovirus envelope glycoprotein. Additional plasmids can be used to enhance retrovirus particle production, e.g., Rev-expression plasmids, as described herein and known in the art. Viral particles bud through the cell membrane and comprise a core that includes a genome containing the sequence of interest and an Arbovirus envelope glycoprotein that targets dendritic cells. When the Arbovirus glycoprotein is Sindbis virus E2 glycoprotein, the glycoprotein is engineered to have reduced binding to heparan sulfate compared to the reference strain HR.

Transfection of packaging cells with plasmid vectors of the present invention can be accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein A G. (2001. Non-Viral Vectors in Cancer Gene Therapy: Principles and Progresses. Anticancer Drugs, which is incorporated herein by reference in its entirety). Cationic lipid or salt treatment methods are typically employed, see, for example. Graham et al. (1973. Virol. 52:456; Wigler et al. (1979. Proc. Natl. Acad. Sci. USA 76:1373-76), each of the foregoing which is incorporated herein by reference in its entirety. The calcium phosphate precipitation method is most often used. However, other methods for introducing the vector into cells may also be used, including nuclear microinjection and bacterial protoplast fusion.

The packaging cell line provides the components, including viral regulatory and structural proteins, that are required in trans for the packaging of the viral genomic RNA into lentiviral vector particles. The packaging cell line may be any cell line that is capable of expressing lentiviral proteins and producing functional lentiviral vector particles. Some suitable packaging cell lines include 293 (ATCC CCL X), 293T, HeLa (ATCC CCL 2), D17 (ATCC CCL 183), MDCK (ATCC CCL 34), BHK (ATCC CCL-10) and Cf2Th (ATCC CRL 1430) cells. The packaging cell line may stably express the necessary viral proteins. Such a packaging cell line is described, for example, in U.S. Pat. No. 6,218,181, which is incorporated herein by reference in its entirety. Alternatively a packaging cell line may be transiently transfected with nucleic acid molecules encoding one or more necessary viral proteins along with the viral vector genome. The resulting viral particles are collected and used to infect a target cell. The gene(s) encoding envelope glycoprotein(s) is usually cloned into an expression vector, such as pcDNA3 (Invitrogen, CA USA). Eukaryotic cell expression vectors are well known in the art and are available from a number of commercial sources. Packaging cells, such as 293T cells are then co-transfected with the viral vector genome encoding a sequence of interest (typically encoding an antigen), at least one plasmid encoding virus packing components, and a vector for expression of the targeting molecule. The envelope is expressed on the membrane of the packaging cell and incorporated into the viral vector.

In one scenario, one or more vectors are used to introduce polynucleotide sequences into a packaging cell line for the preparation of a lentiviral vector particle pseudotyped with a Sindbis virus envelope glycoprotein such as E2, as described herein. The vectors can contain polynucleotide sequences encoding the various components of the virus including the Sindbis virus envelope, a sequence(s) of interest (typically encoding an antigen), and any components necessary for the production of the virus that are not provided by the packaging cell.

In yet other scenarios, packaging cells are co-transfected with a viral vector genome encoding an antigen and one or more additional vectors. For example, in addition to the viral vector encoding an antigen, a second vector preferably carries the genes encoding a modified (also called a variant) Sindbis virus envelope. In some situations, the viral vector genome encoding an antigen also includes a polynucleotide sequence encoding a selected immune modulating factor, including non-limiting examples of a chemokine, a cytokine, a DC maturation factor, or a factor that regulates immune checkpoint mechanisms. In other situations, the polynucleotide sequence encoding a selected immune modulating factor is contained in a third vector that is co-transfected with the viral vector encoding an antigen and the one or more additional vectors into the packaging cells.

Production of virus is measured as described herein and expressed as IU per volume. IU is infectious unit, or alternatively transduction units (TU); IU and TU can be used interchangeably as a quantitative measure of the titer of a viral vector particle preparation. As described herein, virus is produced in which the genome can express a product that is readily measurable. A fluorescent protein, green fluorescent protein, is preferred. The lentiviral vector is typically non-integrating. The virus is then administered to target cells and the number of target cells that express GFP is determined, such as by flow cytometry (see Example 3). The titer is then calculated. The titer is preferably as high as possible, but at least $1\times10^5$ IU/mL, at least $3\times10^5$ IU/mL, at least $1\times10^6$ IU/mL, at least $3\times10^6$ IU/mL, or at least $1\times10^7$ IU/mL of cell supernatant (before any concentration). Alternatively, the titer is at least 80%, at least 90%, at least 95%, at least 100% of the titer of the same lentiviral vector pseudotyped in the same cells with VSV-G envelope.

C. Delivery of the Virus

The virus may be delivered to a target cell in any way that allows the virus to contact the target dendritic cells (DCs) in which delivery of a polynucleotide of interest is desired. At times, a suitable amount of virus will be introduced into a human or other animal directly (in vivo), e.g., though injection into the body. Suitable animals include, without limitation, horses, dogs, cats, cattle, pigs, sheep, rabbits, chickens or other birds. Viral particles may be injected by a number of routes, such as intravenous, intra-dermal, subcutaneous, intranodal, intra-peritoneal cavity, or mucosal. The virus may be delivered using a subdermal injection device such the devices disclosed in U.S. Pat. Nos. 7,241,275, 7,115,108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499, all of which are incorporated by reference in their entirety. Other injection locations also are suitable, such as directly into organs comprising target cells. For example intra-lymph node injection, intra-spleen injection, or intra-bone marrow injection may be used to deliver virus to the lymph node, the spleen and the bone marrow, respectively. Depending on the particular circumstances and nature of the target cells, introduction can be carried out through other means including for example, inhalation, or direct contact with epithelial tissues, for example those in the eye, mouth or skin.

Alternatively, target cells are provided and contacted with the virus in vitro, such as in culture plates. The target cells are typically populations of cells comprising dendritic cells obtained from a healthy subject or a subject in need of treatment or in whom it is desired to stimulate an immune response to an antigen. Methods to obtain cells from a subject are well known in the art and includes phlebotomy, surgical excision, and biopsy. Human DCs may also be generated by obtaining CD34α+ human hematopoietic progenitors and using an in vitro culture method as described elsewhere (e.g., Banchereau et al. Cell 106, 271-274 (2001) incorporated by reference in its entirety).

The virus may be suspended in media and added to the wells of a culture plate, tube or other container. Media containing the virus may be added prior to the plating of the cells or after the cells have been plated. Cells are typically incubated in an appropriate amount of media to provide viability and to allow for suitable concentrations of virus in the media such that transduction of the host cell occurs. The cells are preferably incubated with the virus for a sufficient amount of time to allow the virus to infect the cells. Preferably the cells are incubated with virus for at least 1 hour, at least 5 hours or at least 10 hours.

In both in vivo and in Who delivery, an aliquot of viral particles containing sufficient number to infect the desired target cells may be used. When the target cell is to be cultured, the concentration of the viral particles is generally at least 1 IU/$\mu$L, more preferably at least 10 IU/$\mu$l, even more preferably at least 300 IU/$\mu$L, even more preferably at least $1\times10^4$ IU/$\mu$l, even more preferably at least $1\times10^5$ IU/$\mu$L, even more preferably at least $1\times10^6$ IU/$\mu$L, or even more preferably at least $1\times10^7$ IU/$\mu$L Following infection with the virus in vitro, target cells can be introduced (or re-introduced) into a human or other animal. The cells can be introduced into the dermis, under the dermis, or into the peripheral blood stream. The cells introduced into an animal are preferably cells derived from that animal, to avoid an adverse immune response. Cells derived from a donor having a similar immune background may also be used. Other cells that also can be used include those designed to avoid an adverse immunologic response.

Target cells may be analyzed for integration, transcription and/or expression of the sequence or gene(s) of interest, the number of copies of the gene integrated, and the location of the integration, for examples. Such analysis may be carried out at any time and may be carried out by any method known in the art.

Subjects in which a virus or virus-infected dendritic cells are administered can be analyzed for location of infected cells, expression of the virus-delivered polynucleotide or gene of interest, stimulation of an immune response, and monitored for symptoms associated with a disease or disorder by any methods known in the art.

The methods of infecting cells disclosed above do not depend upon individual-specific characteristics of the cells. As a result, they are readily extended to a variety of animal species. In some instances, viral particles are delivered to a human or to human dendritic cells, and in other instances they are delivered to an animal such as a mouse, horse, dog, cat, or mouse or to birds. As discussed herein, the viral vector genome is pseudotyped to confer upon it a broad host range as well as target cell specificity. One of skill in the art would also be aware of appropriate internal promoters and other elements to achieve the desired expression of a sequence of interest in a particular animal species. Thus, one of skill in the art will be able to modify the method of infecting dendritic cells from any species.

Dendritic cells may be infected with a lentivirus vector particle as described herein for the prevention of or treatment of a disease or disorder, particularly those for which activation of an immune response in a patient would be beneficial. The immunizations may thus be therapeutic or prophylactic. Many such diseases are well known. For example, diseases or disorders that are amenable to treatment or prevention by the methods of the present invention include, without limitation, cancers, autoimmune diseases, and infections, including viral, bacterial, fungal and parasitic infections. In one method, a disease is treated by viral particles described herein in order to deliver a sequence of interest to dendritic cells, wherein expression of the sequence of interest produces a disease-specific antigen and leads to stimulation of antigen-specific cellular immune responses and humoral immune responses. Generally, the sequence of interest encodes an antigen against which an immune response is desired, but is not normally expressed in a dendritic cell. The antigen is expressed and presented by the dendritic cell. The viral vector genome may further encode a DC maturation factor.

In a typical usage, viral particles deliver to dendritic cells sequences encoding an antigen against which an immune response is desired. The delivery can be achieved by contacting dendritic cells with the virus in vitro, whereupon the infected dendritic cells are provided to a patient. Other times, delivery can be achieved by delivering the virus to a subject for infecting dendritic cells in vivo. The dendritic cells then stimulate antigen-specific T cells or B cells in a patient to induce cellular and humoral immune responses to the expressed antigen. In such ways, a patient that is suffering from a disease or disorder is treated by generating immune cells with a desired specificity.

Any antigen that is associated with a disease or disorder can be delivered to dendritic cells using the viral particles as described herein. An antigen that is associated with the disease or disorder is identified for preparation of a viral particle that targets dendritic cells. Antigens associated with many diseases and disorders are well known in the art. An antigen may be previously known to be associated with the disease or disorder, or may be identified by any method known in the art. For example, an antigen to a type of cancer from which a patient is suffering may be known, such as a tumor-associated antigen or may be identified from the tumor itself by any of a variety of methods known in the art.

Tumor-associated antigens are known for a variety of cancers including, for example, renal cell carcinoma, prostate cancer, melanoma, and breast cancer. In some breast cancers, for example, the Her-2 receptor is overexpressed on the surface of cancerous cells. Exemplary tumor antigens include, but are not limited to, MAGE, BAGE, RAGE, and NY-ESO-1, which are unmutated antigens expressed in the immune-privileged areas of the testes and in a variety of tumor cells; lineage-specific tumor antigens such as the melanocyte-melanoma lineage antigens MART-1/Melan-A, gp100, gp75, mda-7, tyrosinase and tyrosinase-related protein, renal cell carcinoma—5T4, SM22-alpha, carbonic anhydrases I and IX (also known as G250), hypoxia-inducible factors (e.g., HIF-1alpha and HIF-2alpha). VEGF or prostate specific membrane antigen (PSMA), prostate-specific antigen (PSA), prostatic acid phosphates, and six-transmembrane epoithelial antigen of the prostate (STEAP). NKX3.1, which are antigens expressed in normal and neoplastic cells derived from the same tissue; epitope proteins/peptides derived from genes mutated in tumor cells or genes transcribed at different levels in tumor compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; epitope proteins/peptides derived from oncoviral processes, such as human papilloma virus proteins E6 and E7; nonmutated oncofetal proteins with a tumor-selective expression, such as carcinoembryonic antigen and alpha-fetoprotein. A number of tumor associated antigens have been reviewed (see, for example, "Tumor-Antigens Recognized By T-Lymphocytes," Boon T, Cerottini J C. Vandeneynde B. Vanderbruggen P. Vanpel A. Annual Review Of Immunology 12: 337-365, 1994; "A listing of human tumor antigens recognized by T cells," Renkvist N, Castelli C. Robbins P F. Parmiani G. Cancer Immunology Immunotherapy 50: (1) 3-15 MAR 2001, each of which is incorporated herein by reference in its entirety.)

The antigen can also be an antigen associated with an infectious disease, such as, for example, HIV/AIDS. The antigen can be, for example, gp120 (Klimstra, W. B., et al. 2003. J Virol 77:12022-12032; Bernard, K. A., et al. 2000. Virology 276:93-103; Byrnes, A. P., et al. 1998. J Virol 72: 7349-7356, each of which is incorporated herein by reference in its entirety). Other exemplary antigens include, but are not limited to: gag, pol, env, tat, nef and rev (Lieberman. J. et al. 1997. AIDS Res Hum Retroviruses 13(5): 383-392; Menendez-Arias, L. et al. 1998. Viral Immunol 11(4): 167-181, each of which is incorporated herein by reference in its entirety).

Examples of viral antigens include, but are not limited to, adenovirus polypeptides, alphavirus polypeptides, calicivirus polypeptides, e.g., a calicivirus capsid antigen, coronavirus polypeptides, distemper virus polypeptides. Ebola virus polypeptides, enterovirus polypeptides, flavivirus polypeptides, hepatitis virus (AE) polypeptides, e.g., a hepatitis B core or surface antigen, or a hepatitis C virus E1 or E2 glycoproteins, core, or non-structural proteins, herpesvirus polypeptides, e.g., a herpes simplex virus or varicella zoster virus glycoprotein, immunodeficiency virus polypeptides, e.g., human immunodeficiency virus envelope or protease, infectious peritonitis virus polypeptides, influenza virus polypeptides, e.g., and influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein g, reovirus polypeptides, retrovirus polypeptides, and rotavirus polypeptides.

Examples of bacterial antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxialla* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenza* type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyrogenes* M proteins, *Treponema* polypeptides, and *Yersinia* polypeptides, e.g., *Y. pestis* F1 and V antigens.

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite antigens include, but are not limited to, polypeptides (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Once an antigen has been identified and selected, a sequence that encodes the desired antigen is identified. Preferably the sequence comprises a cDNA. Following viral infection, the sequence of interest (e.g., one encoding the antigen) is expressed by the target dendritic cells. If contacted ex vivo, the target dendritic cells are then transferred back to the patient, for example by injection, where they interact with immune cells that are capable of generating an immune response against the desired antigen. In preferred embodiments, the recombinant virus is injected into the patient where it transduces the targeted dendritic cells in situ. The dendritic cells then express the particular antigen associated with a disease or disorder to be treated, and the patient is able to mount an effective immune response against the disease or disorder.

The viral vector genome may contain a polynucleotide sequence encoding more than one antigen, and upon transduction of a target dendritic cell, generates immune responses to the multitude of antigens delivered to the cell. In some embodiments, the antigens are related to a single disease or disorder. In other embodiments, the antigens are related to multiple diseases or disorders.

In some of the viruses. DC maturation factors that activate and/or stimulate maturation of the DCs are delivered in conjunction with the sequence of interest. In alternatives, the DCs are activated by delivery of DC maturation factors prior to, simultaneously with, or after delivery of the virus. DC maturation factors may be provided separately from administration of the virus.

As described herein, one or more immune modulation or DC maturation factors can be encoded by one or more sequences that are contained in the viral genome and expressed after the virus infects a dendritic cell. The sequences encoding immune modulation factors can also be provided in a separate vector that is co-transfected with the viral vector encoding one or more antigens in a packaging cell line.

The methods described herein can be used for adoptive immunotherapy in a patient. As described above, an antigen against which an immune response is desired is identified. A polynucleotide encoding the desired antigen is obtained and packaged into a recombinant virus. Target dendritic cells are obtained from the patient and transduced with a recombinant virus containing a polynucleotide that encodes the desired antigen. The dendritic cells are then transferred back into the patient.

The viral particles may be injected in vivo, where they infect DCs and deliver a sequence of interest, typically encoding an antigen. The amount of viral particles is at least $3 \times 10^6$ IU, and can be at least $1 \times 10^7$ IU, at least $3 \times 10^7$ IU, at least $1 \times 10^8$ IU, at least $3 \times 10^8$ IU, at least $1 \times 10^9$ IU, or at least $3 \times 10^9$ IU. At selected intervals. DCs from the recipient's lymphoid organs may be used to measure expression, for example, by observing marker expression, such as GFP or luciferase. Nucleic acid monitoring techniques and measurements of reverse transcriptase (RT) activity can also be used to analyze the biodistribution of viral particles. T cells from peripheral blood mononuclear cells, lymph nodes, spleens, or malignant or target pathogen-infected tissue of lentiviral vector particle-treated recipients may be measured from the magnitude and durability of response to antigen stimulation. Tissue cells other than DCs, such as epithelial cells and lymphoid cells, may be analyzed for the specificity of in vivo gene delivery.

It is widely agreed that the most effective potential method to end the AIDS epidemic (and other viral diseases) is an effective preventative vaccine. To date, no vaccination method against HIV has successfully passed a phase III trial. Thus, there is an urgent need for new, effective vaccination strategies. One strategy is vaccination of DCs. In this implementation, a sequence encoding a viral protein, such as those described above, is cloned into a viral vector. Patients are infected with viruses constructed as described herein. In an animal model, molecularly cloned HIV reporter viruses (NFNSZ-r-HSAS. NL-r-HSAS) and clinical isolates may be used to challenge the animals by tail vein injection. Evidence of infection may be monitored over time in splenocytes, lymph nodes, and peripheral blood. PCR amplification for HIV-gag protein and flow cytometry for HAS in the reporter viruses may be used to test for viral integration and replication. Productive in situ DC vaccination may increase resistance to a HIV challenge.

Vaccines often include an adjuvant. The lentiviral vector particles described herein may also be administered along with an adjuvant. The adjuvant may be administered with the recombinant virus particles, before the recombinant virus particles, or after the recombinant virus particles. If administered with the virus particles, desirable adjuvants do not significantly disrupt the integrity of the virus particle, such as disrupting the viral membrane containing the envelope glycoproteins.

A variety of adjuvants can be used in combination with the virus to elicit an immune response to the antigen encoded in the viral vector genome. Preferred adjuvants augment the intrinsic response to an antigen without causing conformational changes in the antigen that affect the qualitative form of the response. Preferred adjuvants include alum, 3 De-O-acylated monophosphoryl lipid A (MPL) (see GB 2220211). QS21 is a triterpene glycoside or saponin isolated from the bark of the Quillaja *Saponaria* Molina tree found in South America (see Kensil et al., in Vaccine Design: The Subunit and Adjuvant Approach (eds. Powell and Newman, Plenum Press, NY, 1995); U.S. Pat. No. 5,057,540). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Alternatively, Aβ can be coupled to an adjuvant. For example, a lipopeptide version of Aβ can be prepared by coupling palmitic acid or other lipids directly to the N-terminus of Aβ as described for hepatitis B antigen vaccination (Livingston, J. Immunol. 159, 1383-1392 (1997)). However, such coupling should not substantial/change the conformation of A13 so as to affect the nature of the immune response thereto. Adjuvants can be administered as a component of a therapeutic composition with an active agent or can be administered separately, before, concurrently with, or after administration of the therapeutic agent.

One class of adjuvants is aluminum salts (alum), such as aluminum hydroxide, aluminum phosphate, aluminum sulfate. Such adjuvants can be used with or without other specific immunostimulating agents such as MPL or 3-DMP. QS21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isogluta mine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS21, Aquila, Worcester, Mass.) or particles generated there from such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

Another adjuvant can be used with the compositions herein is identified by chemical formula (I):

(I)

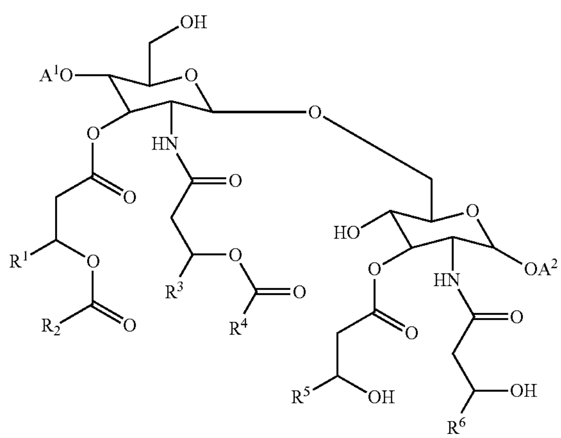

wherein the moieties A1 and A2 are independently selected from the group of hydrogen, phosphate, and phosphate salts. Sodium and potassium are exemplary counterions for the phosphate salts. The moieties $R^1$, $R^2$, $R^3$, $R^4$, $R^5$, and $R^6$ are independently selected from the group of hydrocarbyl having 3 to 23 carbons, represented by $C_3$-$C_{23}$. For added clarity it will be explained that when a moiety is "independently selected from" a specified group having multiple members, it should be understood that the member chosen for the first moiety does not in any way impact or limit the choice of the member selected for the second moiety. The carbon atoms to which $R^1$, $R^3$, $R^5$ and $R^6$ are joined are asymmetric, and thus may exist in either the R or S stereochemistry. In one embodiment all of those carbon atoms are in the R stereochemistry, while in another embodiment all of those carbon atoms are in the S stereochemistry.

"Hydrocarbyl" refers to a chemical moiety formed entirely from hydrogen and carbon, where the arrangement of the carbon atoms may be straight chain or branched, noncyclic or cyclic, and the bonding between adjacent carbon atoms maybe entirely single bonds, i.e., to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl", respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

The adjuvant of formula (I) may be obtained by synthetic methods known in the art, for example, the synthetic methodology disclosed in PCT International Publication No. WO 2009/035528, which is incorporated herein by reference, as well as the publications identified in WO 2009/035528, where each of those publications is also incorporated herein by reference. Certain of the adjuvants may also be obtained commercially. A preferred adjuvant is Product No. 699800 as identified in the catalog of Avanti Polar Lipids, Alabaster A L, see E1 in combination with E10, below.

In various embodiments of the invention, the adjuvant has the chemical structure of formula (1) but the moieties A1, A2, R1, R2, R3, R4, R5, and R6 are selected from subsets of the options previously provided for these moieties, where these subsets are identified below by E1, E2, etc.

E1: $A_1$ is phosphate or phosphate salt and $A_2$ is hydrogen.
E2: $R^1$, $R^3$, $R^5$ and $R^6$ are $C_3$-$C_{21}$ alkyl; and $R^2$ and $R^4$ are $C_5$-$C_{23}$ hydrocarbyl.
E3: $R^1$, $R^3$, $R^5$ and $R^6$ are $C_5$-$C_{17}$ alkyl; and $R^2$ and $R^4$ are $C_7$-$C_{19}$ hydrocarbyl.
E4: $R^1$, $R^3$, $R^5$ and $R^6$ are $C_7$-$C_{15}$ alkyl; and $R^2$ and $R^4$ are $C_9$-$C_7$ hydrocarbyl.
E5: $R^1$, $R^3$, $R^5$ and $R^6$ are $C_9$-$C_{13}$ alkyl; and $R^2$ and $R^4$ are $C_{11}$-$C_{15}$ hydrocarbyl.
E6: $R^1$, $R^3$, $R^5$ and $R^6$ are $C_9$-$C_{15}$ alkyl; and $R^2$ and $R^4$ are $C_{11}$-$C_{17}$ hydrocarbyl.
E7: $R^1$, $R^3$, $R^5$ and $R^6$ are $C_7$-$C_{13}$ alkyl; and $R^2$ and $R^4$ are $C_9$-$C_{15}$ hydrocarbyl.
E8: $R^1$, $R^3$, $R^5$ and $R^6$ are $C_{11}$-$C_{20}$ alkyl; and $R^2$ and $R^4$ are $C_{12}$-$C_{20}$ hydrocarbyl.
E9: $R^1$, $R^3$, $R^5$ and $R^6$ are $C_{11}$alkyl; and $R^2$ and $R^4$ are $C_{13}$ hydrocarbyl.
E10: $R^1$, $R^3$, $R^5$ and $R^6$ are undecyl and $R^2$ and $R^4$ are tridecyl.

In certain options, each of E2 through E10 is combined with embodiment E1, and/or the hydrocarbyl groups of E2 through E9 are alkyl groups, preferably straight chain alkyl groups.

The adjuvant of formula (I) may be formulated into a pharmaceutical composition, optionally with a co-adjuvant, each as discussed below. In this regard reference is made to US Patent Publication No. 2008/0131466 which provides formulations, e.g., aqueous formulation (AF) and stable emulsion formulations (SE) for GLA adjuvant, where these formulations may be utilized for any of the adjuvants of formula (I).

An adjuvant can be administered with the virus of the invention as a single composition, or can be administered before, concurrent with or after administration of the recombinant virus of the invention. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum. MPL and QS21 are preferred. Optionally, two or more different adjuvants can be used simultaneously, such as alum with MPL, alum with QS21. MPL with QS21, and alum. QS21 and MPL together. Also, Incomplete Freund's adjuvant can be used (Chang et al., Advanced Drug Delivery Reviews 32, 173-186 (1998)), optionally in combination with any of alum. QS21, and MPL and all combinations thereof.

D. Pharmaceutical Compositions and Kits

Also contemplated herein are pharmaceutical compositions and kits containing a virus provided herein and one or more components. Pharmaceutical compositions can include viralvector particles as provided herein and a pharmaceutical carrier. Kits can include the pharmaceutical compositions and/or combinations provided herein, and one or more components, such as instructions for use, a device for administering a compound to a subject, and a device for administering a compound to a subject.

Provided herein are pharmaceutical compositions containing viral particles as provided herein and a suitable pharmaceutical carrier. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body.

The viral vector particles provided herein can be packaged as kits. Kits can optionally include one or more components such as instructions for use, devices, and additional reagents, and components, such as tubes, containers and syringes for practice of the methods. Exemplary kits can include the viruses provided herein, and can optionally include instructions for use, a device for detecting a virus in a subject, a device for administering the virus to a subject, and a device for administering a compound to a subject.

Kits comprising polynucleotides encoding a gene of interest (typically an antigen) are also contemplated herein. The kit may include at least one plasmid encoding virus packaging components and vector encoding Sindbis virus E2 glycoprotein variant. Some kits will contain at least one plasmid encoding virus packaging components, a vector encoding Sindbis virus E2 glycoprotein variant, and a vector encoding at least one DC maturation factor.

Kits comprising a viral vector encoding a sequence of interest (typically an antigen) and optionally, a polynucleotide sequence encoding a DC maturation factor are also contemplated herein. In some kits, the kit includes at least one plasmid encoding virus packaging components and a vector encoding Sindbis virus E2 glycoprotein variant.

A kit may also contain instructions. Instructions typically include a tangible expression describing the virus and, optionally, other components included in the kit, and methods for administration, including methods for determining the proper state of the subject, the proper dosage amount, and the proper administration method, for administering the virus. Instructions can also include guidance for monitoring the subject over the duration of the treatment time.

Kits provided herein also can include a device for administering a virus to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high pressure injection device can be included in kits with viruses not damaged by high pressure injection, but is typically not included in kits with viruses damaged by high pressure injection.

Kits provided herein also can include a device for administering a compound, such as a DC activator or stimulator, to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically the device for administering the compound of the kit will be compatible with the desired method of administration of the compound.

The following examples are offered by way of illustration, and not by way of limitation.

EXAMPLES

Example 1

Engineering of a Sindbis Virus Envelope Variant

Figure 1B:
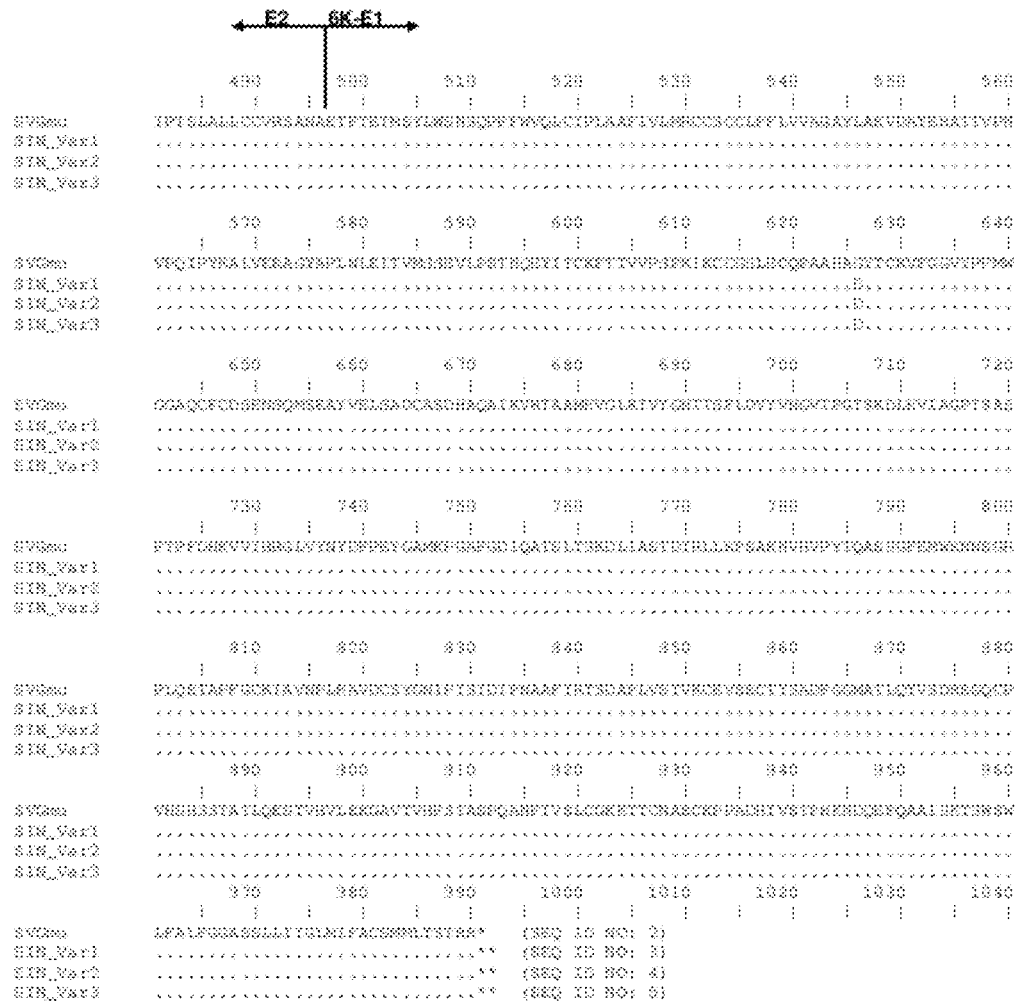
Figure 2:
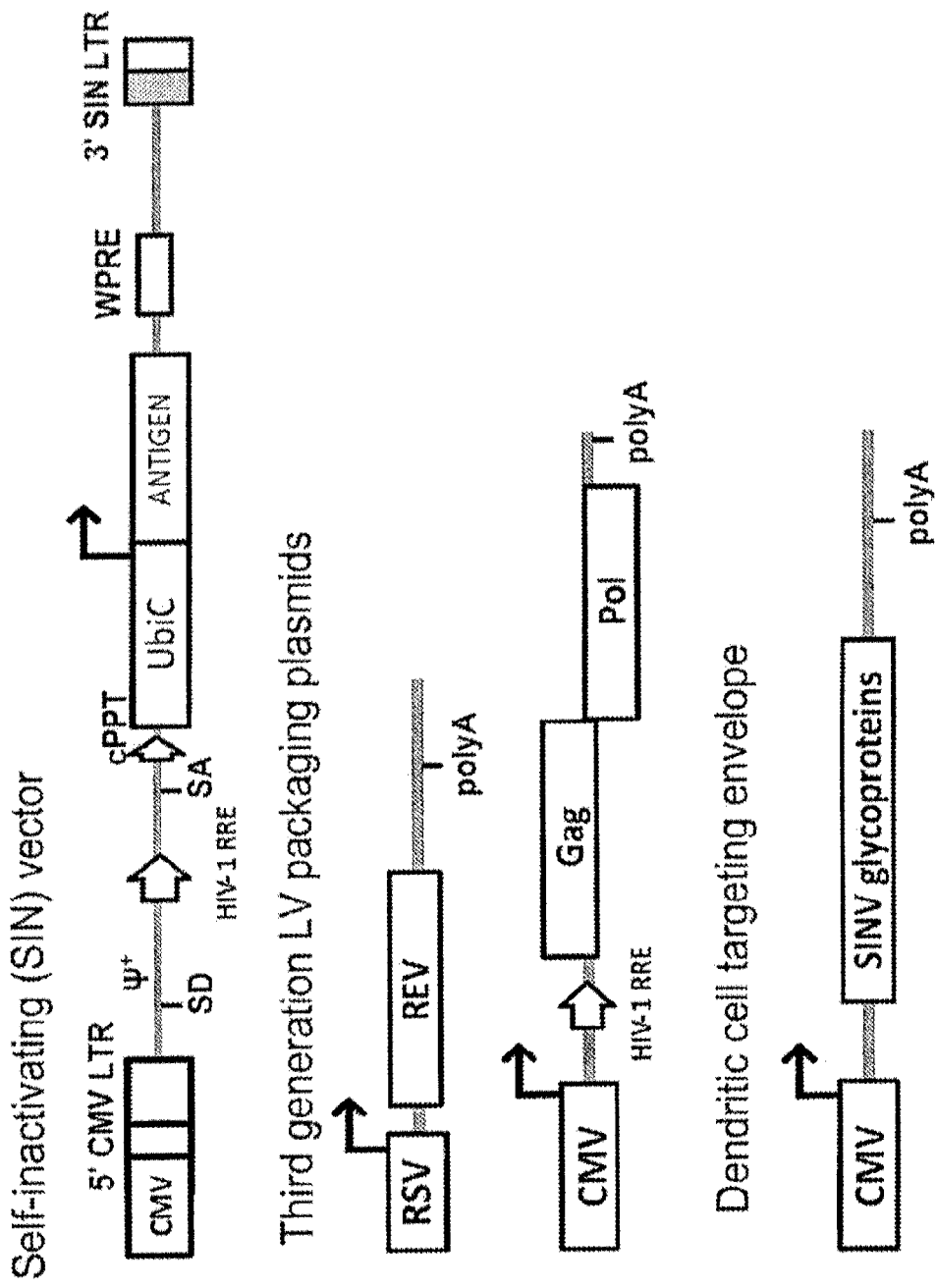
FIG. 2 is a schematic of exemplary vectors used in packaging viral particles.

Sindbis virus (SV)—a member of the *Alphavirus* genus and the Togaviridae family—is able to infect DCs, probably through DC-SIGN (Klimstra, W. B., et al. 2003. J. Virol. 77: 12022-12032, which is incorporated herein by reference in its entirety). The canonical viral receptor for the laboratory strain of SV however, is cell-surface heparan sulfate (HS), which is found on many cell types (Strauss, J. H., et al. 1994. Arch. Virol. 9: 473-484; Byrnes, A. P., and D. E. Griffin. 1998. J. Virol. 72: 7349-7356, each of which is incorporated herein by reference in its entirety). To try to reduce heparan sulfate binding, a mutant E2 envelope (called SVGmu) was constructed by Wang et al. (US 2008/0019998, incorporated in its entirety). Part of their strategy involved deleting four amino acids at the E3/E2 pro-protein junction and a deletion of two amino acids with a subsequent addition of a 10 amino acid sequence from hemagglutinin (see FIGS. 1A and 1B). The resulting E2 protein is expressed as a fusion of E3 and E2 (also known as pE2) because the natural cleavage sequence was disrupted, and it also displays a foreign epitope (hemagglutinin). As shown below, SVGmu suffers from low expression levels among other problems.

Using a different strategy, the inventors have engineered the E2 glycoprotein of Sindbis virus to decrease binding to heparan sulfate, increase specificity with dendritic cells, and improve expression. A general approach to attain these characteristics is to increase infectivity of dendritic cells by changing residue 160 of E2 (residues 233 in FIG. 1) to a non-acidic amino acid, especially an amino acid other than alanine, or delete it, to decrease heparin binding by reducing net positive charge of the protein, to remove the HA (hemagglutinin) epitope, and to restore a cleavage site at the N-terminus of E2, in this case a furin cleavage site. As part of a viral envelope, these E2 glycoproteins are able to mediate infection of DCs as well as have reduced or abrogated infection of other cell types.

Following these principles, several variant sequences of E2 were designed and are shown in the following table. The bold typeface indicates a change from the HR strain Sindbis virus envelope sequence (GenBank NC 001547.1).

| SEQ ID No: | 70 | 76 | 159 | 160 |
|---|---|---|---|---|
| 3 | E | K | E | G |
| 4 | E | E | E | G |
| 5 | E | K | Δ | Δ |
| 6 | E | E | E | Δ |
| 7 | K | K | E | G |
| 8 | K | K | E | Δ |
| 9 | K | E | E | G |
| 10 | K | E | E | Δ |
| 11 | K | E | K | G |
| 12 | K | E | K | Δ |
| 13 | E | K | K | G |
| 14 | E | K | K | Δ |
| 15 | E | E | K | G |
| 16 | E | E | K | Δ |

Nucleic acid sequences encoding some of the variants were synthesized (see also FIG. 1), including nucleic acid sequences that are codon-optimized for humans. The DNAs for the variants were cloned into an expression vector, such as pcDNA3.

Example 2

Preparation of a Viral Particle Comprising a Sindbis Virus E2 Envelope Glycoprotein Variant A Sindbis envelope-pseudotyped virus is prepared by standard calcium phosphate-mediated transient transfection of 293T cells with a lentiviral vector, such as FUGW or its derivatives, packaging plasmids encoding gag, pol and rev, and a variant Sindbis virus envelope sequence. FUGW is a self-inactivating lentiviral vector carrying the human ubiquitin-C promoter to drive the expression of a GFP reporter gene (Lois, C., et al. 2002. Science 295: 868-872, which is incorporated herein by reference in its entirety). The lentiviral transfer vectors (FUGW and its derivatives) are third generation HIV-based lentiviral vectors (see generally, Cockrell and Kafri Mol. Biotechnol. 36: 184, 2007), in which most of the U3 region of the 3' LTR is deleted, resulting in a self-inactivating 3'-LTR.

Production of recombinant lentivirus vectors was accomplished by calcium phosphate ($CaPO_4$)-mediated transient transfection of 293T cells (293LTV cell line; CELL BIOLABS INC, LTV-100). 293T cells were transfected with four plasmids precipitated together with $CaPO_4$. The following four plasmids were used to produce lentiviral vector preparations are shown schematically in FIG. 3 and corresponded to the following: i) lentiviral vector; ii) HIV Rev encoding plasmid; iii) HIV Gag/Pol encoding plasmid; and, iv) envelope encoding plasmid. Lentiviral vectors may encode desired antigens or immunomodulatory elements, and contain particular targeted deletions to prevent integration into the host chromosome of the infected cells. Further examples of alternative plasmids that can be utilized for transient transfection include those that encode a Polymerase holoenzyme that harbors a mutation in its integrase rendering it defective, such as the D64V mutation described herein. For certain purposes, the envelope encoding plasmid may encode a non-DC targeting pantropic envelope such as VSV-G.

For the experiments described herein. CaPO$_4$ precipitations containing 120 µg vector and 60 µg each of Gag/Pol and Rev plasmids and 240 µg of envelope plasmid that were filtered through a 0.45 µm pore size filter and were added to approximately 6×10$^7$ 293T cells grown in roller bottles and containing 75 mL of DMEM media supplemented with 10% fetal calf serum. At 6 hours post transfection, the media was replaced with 100 mL of fresh media and collected at 36 hours post transfection. Culture supernatants were centrifuged at low speed (1200 rpm) to pellet cell debris followed by filtration through 0.45 µm filters. The filtrate containing the lentivirus vector preparation was optionally concentrated by centrifugation at 17,700×g for 5 hours at 20° C. The pelleted lentivirus vector was then resuspended in PBS at a desired volume. This process typically yielded >5×10$^5$ IU/mL using the Sindbis virus glycoprotein envelope described herein, or 5×10$^7$ IU total for each roller bottle culture. More typically this process yielded at least 1×10$^8$ IU total for each roller bottle culture.

In more detail, at day −4, 150 mL cell culture medium is added to Roller Bottles (RB) that are placed in a 37° C. roller rack incubator (0.2 rpm) for ~1 hr. Into each RB is passed confluent 15 cm dishes. At day −2, medium is aspirated from RBs and replaced with 100 mL pre-warmed medium. On day −1, the cells are seeded in preparation for transfection. RBs are prewarmed with 100 mL cell culture medium for ~1 hr. Medium is aspirated and 10-12 mL of PBS is added. The RBs are placed on their side and rotated twice around to coat the cells. The PBS is aspirated and 10-12 mL of trypsin solution is added. RBs are again placed on their sides and rotated twice around to coat the cells. The trypsin solution is aspirated and the RBs are placed in the incubator for 5 min. To the RBs, 10 mL of warm medium is added and the RBs are rotated vigorously once around to detach the cells. Using a 10 mL pipet, cells are pipetted up and down for e.g., 10 times to ensure a single cell suspension. Cells are removed to a new container and diluted with medium (40 mL medium per RB). Cells are counted and seeded into fresh RBs at 7×10$^7$/ml and kept in the incubator overnight.

On day 0, at approximately 22 hr post-seeding, the plasmid solution was prepared as follows. For each RB, mix together a plasmid solution (120 µg vector, 60 µg Gag/Pol, 60 µg Rev, 60 µg envelope), 2.5 mL 1.25M CaCl$_2$, and filtered-sterile water to 12.5 mL final volume. Add 2.7 ml 2×HBS (50 mM HEPES, 10 mM KCl, 12 mM dextrose, 280 mM NaCl, 1.5 mM Na2HPO4.7H2O, pH 7.0, sterile filtered) buffer to a 50 ml tube (one tube/RB). Add 12.7 mL water-CaCl2-DNA mix dropwise to 12.7 mL 2×HBS while vortexing at medium setting. Cap the tube and continue to vortex (max speed) for 5-10 seconds. Remove 25 ml medium from RB and add precipitate (25 ml) to RB. Incubate 6 hr, then aspirate off medium and add 100 ml of fresh, pre-warmed cell culture medium. Place back in 37° incubator.

At 36 to 48 hr post-transfection, the supernatants from RB were collected into a 250 mL conical tube and processed as follows. Centrifuge supernatants for 10 min @ 2000 rpm. Filter supernatants through 0.45 um filter. Centrifuge supernatants in 500 ml tube for 5 hr @ 10,000rpm @ 20° C. Resuspend vector in PBS or HBSS to desired concentration and store at −80° C.

The resultant pseudo-typed viral vectors are hereafter referred to as FUGW/V1, FUGW/V2, and so on. Viral vector genomes enveloped with the VSV-G glycoprotein are hereafter referred to as FUGW/VSV-G.

Example 3

Production of Lentiviral Vector Particles Comprising Sindbis Virus Envelope Glycoproteins In this example, titers are determined for lentivirus vectors pseudotyped with different Sindbis virus envelopes. The E2 glycoproteins used were those contained in the sequences SIN-Var1 (SEQ ID No. 3), SIN-Var2 (SEQ ID No. 4), SIN-Var3 (SEQ ID No. 5), SVGmu (SEQ ID No. 2), HR (SEQ ID No. 18).

Sindbis virus glycoprotein pseudotyped lentiviral vector particles were generated by transfection of 293T cells as described in Example 2. Crude supernatants were harvested 48 hours post-transfection and used to transduce 293T cells expressing human DC-SIGN (293-DCSIGN) that had been plated in 6-well dishes the previous day at 2E5 cells/well. Titer was determined following a 72 hr incubation at 37° C. by analyzing transduced cells on a Guava Easy-Cyte cytometer (Millipore). 25,000 total events were counted to determine the percentage of GFP+ transduced cells, which was in turn used to calculate the GFP titer (IU, infectious unit) for each virus.

To facilitate the study of targeted transduction, cell lines expressing human DC-SIGN are constructed. The cell lines are generated by stable transduction of parental 293T cells with a VSVG-pseudotyped lentivector containing the coding sequence for human DC-SIGN. cDNA for human DC-SIGN is amplified from plasmids pUNO-hDCSIGN1Aa (InvivoGene) and cloned downstream of the human ubiquitin-C promoter in the lentiviral plasmid FUW to generate FUW-hDC-SIGN. Alternatively, cell lines are generated by stable transduction of parental 293T cells with a VSVG-pseudotyped amphotrophic (non-lentiviral) vector containing the coding sequence for DC-SIGN, to better facilitate downstream nucleic acid-based analyses of transduction by lentiviral vector particles. The lentivectors or amphotrophic vectors are then pseudotyped with VSVG and used to transduce 293T cells. Alternatively, cell lines are generated by stable transduction of parental 293T cells with a plasmid encoding human DC-SIGN. The resulting cells are subjected to antibody staining (anti-human DC-SIGN antibody (BD Biosciences) and cell sorting to yield a uniform population of DC-SIGN+ cell lines.

Figure 3:
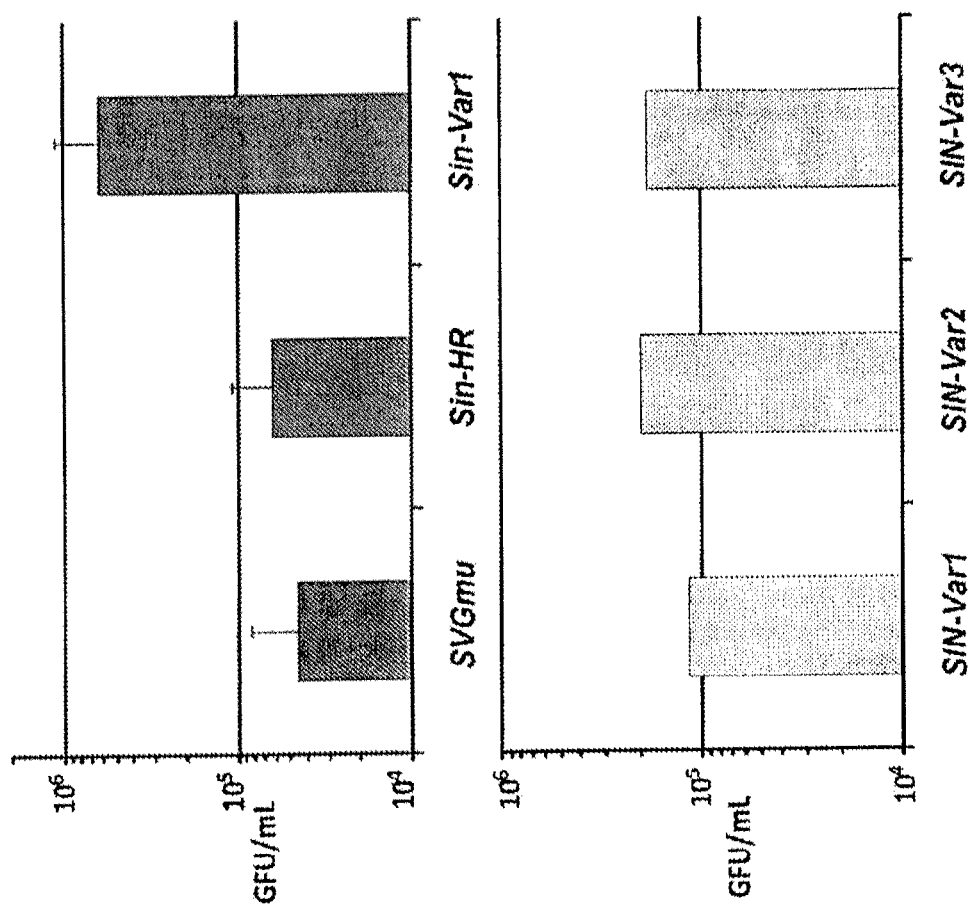
FIG. 3 presents graphs of crude supernatant titers of lentiviral vector particle preparations in which the vector genome was pseudotyped with three different Sindbis virus envelope proteins. SVGmu and SIN-HR. Virus supernatants were generated by transient transfection using standard methods, and collected 48 hours post transfection. Titers were determined on 293T cells expressing human DC-SIGN (293T-DC-SIGN). Titers are expressed as the number of GFP-expressing units per ml of supernatant and are means of three independent transfections. Error bars represent the standard deviation from the mean.

In three independent experiments, lentiviral vector pseudotyped with SIN-Var1 envelope had titers approximately 10-fold higher titer than those pseudotyped with SVGmu or with the HR strain of Sindbis virus (FIG. 3, upper graph). In a subsequent study, the productivity of three Sindbis envelope variants was compared. A representative result is shown. Sin-Var1, Sin-Var2 and SIN-Var3 envelopes generate lentivirus vector particles with similar overall titer.

The specificity of viral vector particles that comprise a Sindbis virus variant E2 glycoprotein is assessed by transduction of the 293T.hDC-SIGN or the parental 293T cells and measurement of expression of a visible marker (e.g., GFP) within the cell lines.

Target cells (293T.hDC-SIGN or 293T cells) are seeded in a 24-well culture dish (0.2×10⁶ cells per well) and transduced with viral supernatants (1 ml per well) by centrifuging the dishes at 2,500 rpm and 30° C. for 90 min. Subsequently, the supernatants are replaced with fresh culture medium and incubated for 3 days at 37° C. The percentage of cells expressing the marker is measured by flow cytometry.

As shown in the table below, both E2 variant 1 and E2 variant 3 preferentially targeted cells (are specific for cells) expressing hDC-SIGN.

TABLE 1

| Envelope | Cell Type | GFU/mL | Ratio |
|---|---|---|---|
| VSV-G | hDC-SIGN | 1.35E+08 | 1.19 |
| | 293T | 1.13E+08 | |
| Sin-Var3 (Exp 1) | 293-hDC-SIGN | 4.2E+07 | 35.4 |
| | 293T | 1.2E+06 | |
| Sin-Var3 (Exp 2) | hDC-SIGN | 8.12E+07 | 11.09 |
| | 293T | 7.33E+06 | |
| Sin-Var2 | 293-hDC-SIGN | 1.7E+08 | 18.2 |
| | 293T | 9.1E+06 | |
| Sin-VAR-1 | hDC-SIGN | 2.93E+08 | 13.75 |
| | 293T | 2.13E+07 | |
| Sin-HR | 293-hDC-SIGN | 6.4E+06 | 9.4 |
| | 293T | 6.8E+05 | |
| SVGmu (Exp 1) | 293-hDC-SIGN | 3.4E+06 | 27.0 |
| | 293T | 1.3E+05 | |
| SVGmu (Exp 2) | hDC-SIGN | 4.65E+06 | 12.24 |
| | 293T | 3.80E+05 | |

Example 4

Immunogenicity of Lentiviral Vector Particles Comprising Sindbis Virus Envelope Glycoproteins In this Example, immunogenicity is assessed for lentivirus vectors pseudotyped with different Sindbis virus envelopes. More specifically, the amount of antigen-specific CD8 T cells and their cytokine secretion profiles were determined. The E2 glycoproteins used are found in the sequences set forth as SIN-Var1 (SEQ ID No. 3), SIN-Var2 (SEQ ID No. 4), SIN-Var3 (SEQ ID No. 5), SVGmu (SEQ ID No. 2).

The viral genome comprises sequence encoding Ovalbumin (OVA). Lentivirus vector particles were generated by transfecting 293T cells as described in Example 2. Supernatants were collected, and the amount of p24 determined using an ELISA kit (Advanced Bioscience Labs, Kensington, Md.). The protein p24 is an HIV core protein found in the pseudotyped virions and a product of the gag gene. C57BL/6 mice (5 mice per group) were immunized subcutaneously with integration-deficient lentivector encoding ovalbumin OVA. The number and function of OVA257 (SIINFEKL) (SEC) ID NO 24) peptide-specific CD8 T cells and cytokine secretion profiles in the spleen was determined at day 9 by MHC-I/peptide multimer and intracellular cytokine staining.

Briefly, spleens were extracted and homogenized by pressing through a 70 μM nylon filter. Red blood cells were lysed by hypotonic shock by brief exposure to distilled water and immediately restored to an isotonic environment with addition of 10× PBS. Approximately 5×10⁶ splenocytes per sample were stained with PE-labeled H-2 Kb/OVA257 pentamer (ProImmune) at 25° C. in PBS with 2% FCS and 2 mM EDTA (FACS buffer). Cells were then washed twice and stained with the viability dye LIVE/DEAD Near-Infrared (L/D NIR; Invitrogen) and the following fluorochrome-labeled antibodies: CD44 FITC, CD19 PerCP-Cy5.5, and CD8 Pacific Blue (eBioscience) at 4° C. Data were collected on a BD LSR II flow cytometer (50,000 CD8+ events) and analyzed with FlowJo software (TreeStar). The gating strategy to identify CD8 T cells was as follows: lymphocytes (forward scatter lo-med, side scatter lo), single cells (side scatter area=side scatter height), live cells (L/D NIR−), CD8 T cells (CD8+ CD19−). The percentage of cells expressing IFN-γ within the CD8+ gate was determined and depicted in FIGS. 4A and 4B. The horizontal line depicts mean values. Non-specific IFN-γ staining was determined in spleen cells of vehicle (HBSS)-injected mice in which the cells were stimulated in vitro with peptide. IFN-γ staining was below 0.2% for all samples cultured without peptide (not shown). In addition to the fraction of CD8 T cells producing IFN-γ, the fraction of IFN-γ+ cells also producing TNFα and/or IL-2 is also depicted, as indicated in the key.

Figure 4A:
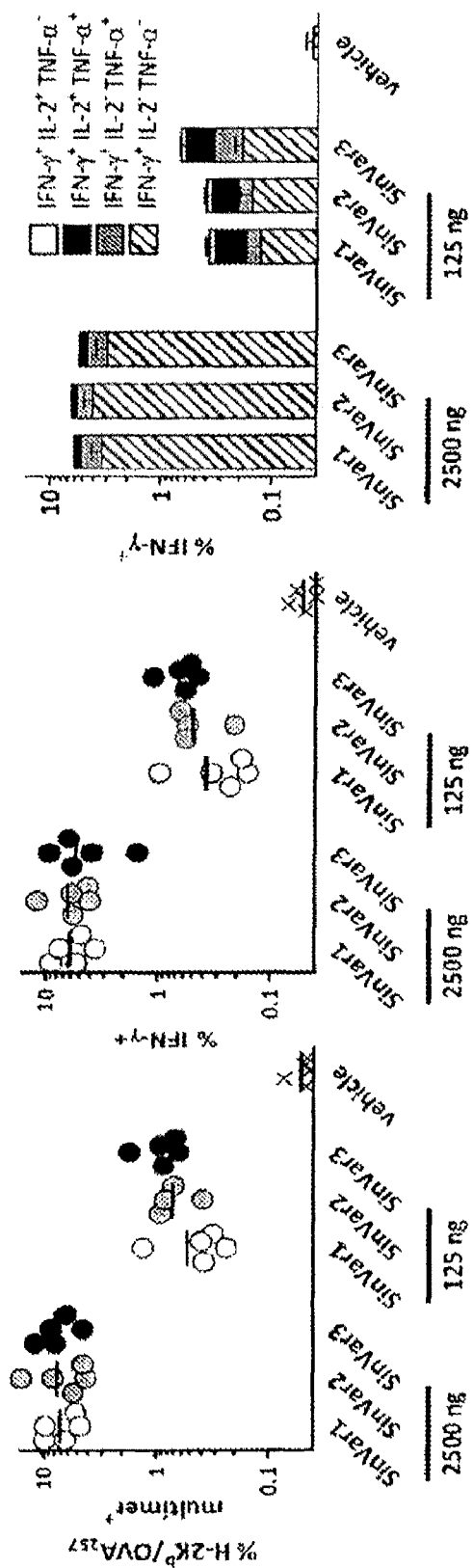
FIGS. 4A, 4B, and 4C are graphs showing immunological responses of T cells in mice following administration of pseudotyped lentiviral vector particles. (A) C57BL/6 mice were immunized subcutaneously with one of two doses (indicated in ng p24) of integration-deficient lentiviral vector encoding OVA. The number and function of OVA257-specific CD8 T cells in the spleen was determined at day 9 by MHC-I/peptide multimer and intracellular cytokine staining. (B) C57BL/6 mice were immunized subcutaneously with a dose range of integration-deficient lentiviral vector encoding OVA. The percentage of OVA257-specific CD8 T cells in the spleen was determined at day 11 by MHC-I/peptide multimer staining. (C) C57BL/6 mice were immunized subcutaneously with a dose range of integration-deficient lentiviral vector encoding OVA. The percentage of OVA257-specific CD8 T cells in the spleen was determined at day 9 by intracellular cytokine staining.

In one set of experiments, the amount of virus used contained either 2500 ng or 125 ng of p24. FIG. 4A illustrates that lentivectors pseudotyped with Sindbis variant envelopes have similar activity in vivo. As shown in the leftmost panel, the mean of antigen-specific CD8 T cells is essentially the same at two different dosing amounts. In addition, the mean percentage of IFN-γ cells is also similar. Patterns of cytokine secretion, specifically the fraction of IFN-gamma positive cells also expressing IL-2 or TNF-alpha, is also similar, with the highest percentage of I IFN-γ cells being negative for IL-2 and TNF-α.

Figure 4B:
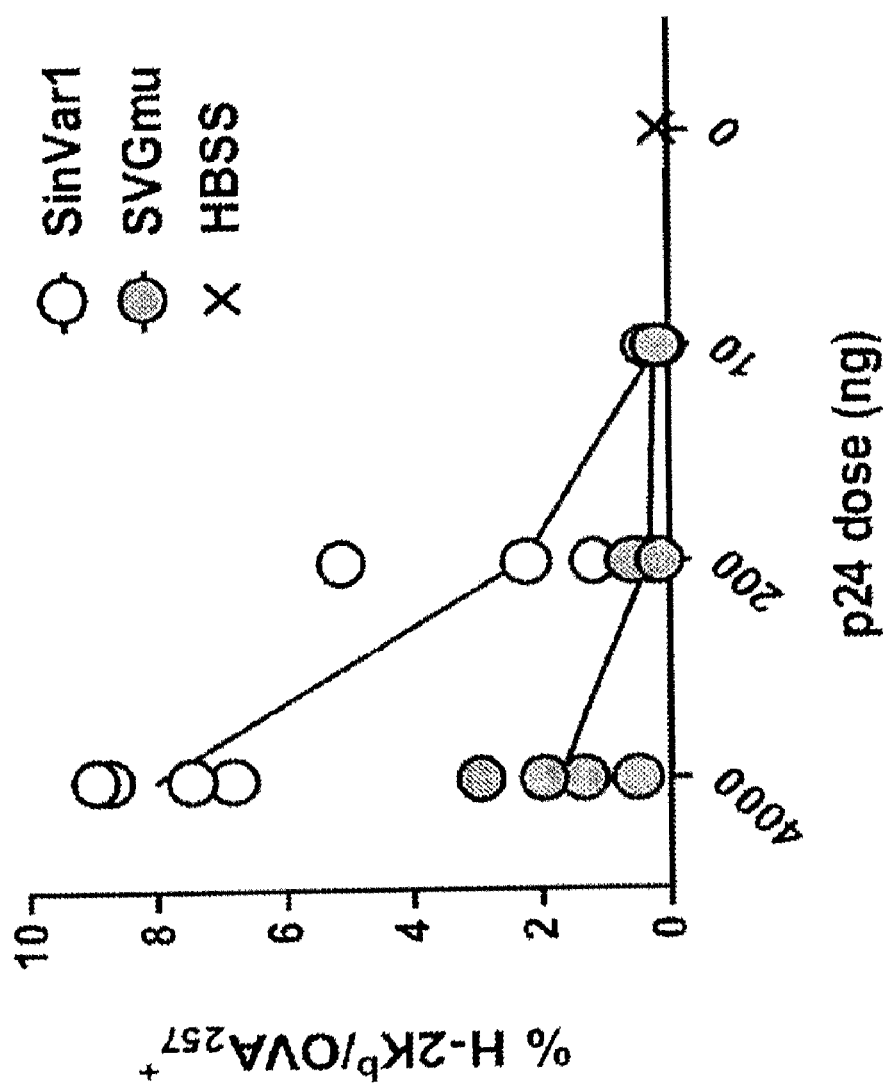
Figure 4C:
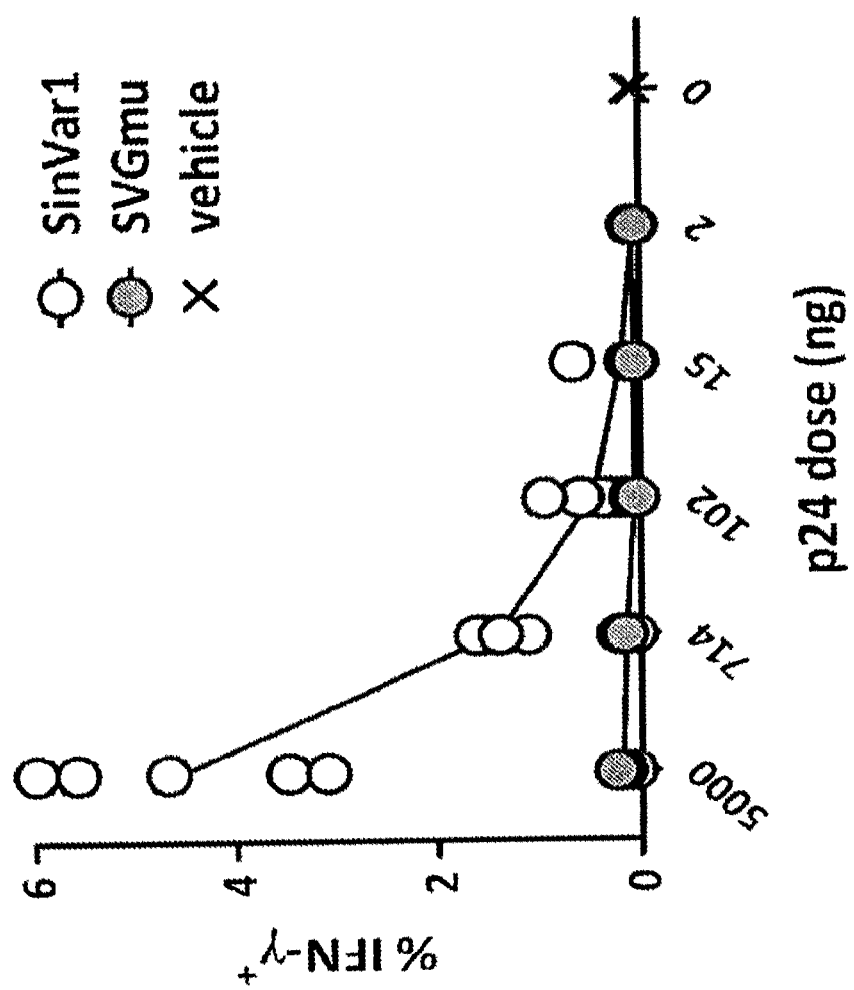

In another set of experiments, groups of 5 mice received a serial dilution dose of virus or vehicle. The virus was pseudotyped with either SinVar1 or SVGmu. The percentage of cells with a CD44hi H-2Kb/OVA257 pentamer+ phenotype is depicted in FIG. 4B. The connecting line depicts mean values. As shown in FIG. 4B, SinVar1-pseudotyped LV induced substantially greater expansion of antigen-specific CD8 T cells than SVGmu. Moreover, the SinVar1-pseudotyped lentivectors induced a greater functional CD8 T cell response than SVGmu (FIG. 4C). Non-specific IFN-γ staining was determined in HBSS-injected (vehicle) mice restimulated with peptide. IFN-γ staining was below 0.2% for all samples cultured without peptide (not shown).

Example 5

Construction of Non-Integrating Lentiviral Vectors (NILV)

Figure 5A:
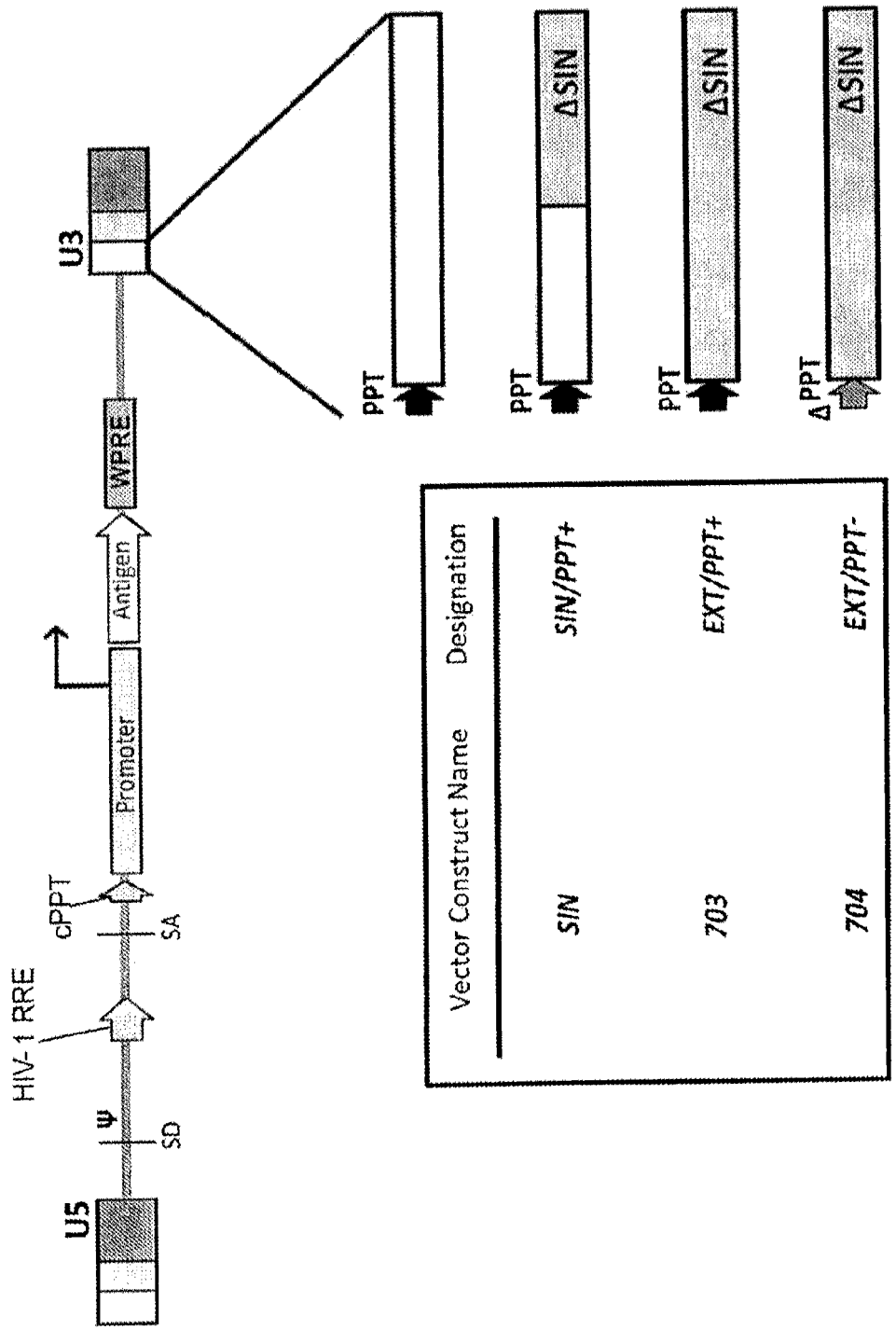
FIG. 5A presents drawings of exemplary lentiviral genomes.

A variety of non-integrating lentiviral vectors were constructed. A schematic of the exemplary lentivirus vectors is shown in FIG. 5A. The top drawing shows a vector in a provirus form. All vectors contain splice donor, packaging signal (psi), a Rev-responsive element (RRE), splice donor, splice acceptor, central poly-purine tract (cPPT) and WPRE element. In addition, all vector constructs contain a promoter for expression in mammalian cells, and a sequence of interest, labeled "antigen" in the exemplary construct. Promoters utilized in the Examples include the human ubiquitin C promoter (UbiC), the cytomegalovirus immediate early promoter (CMV), and the Rous sarcoma virus promoter (RSV).

Figure 5B:
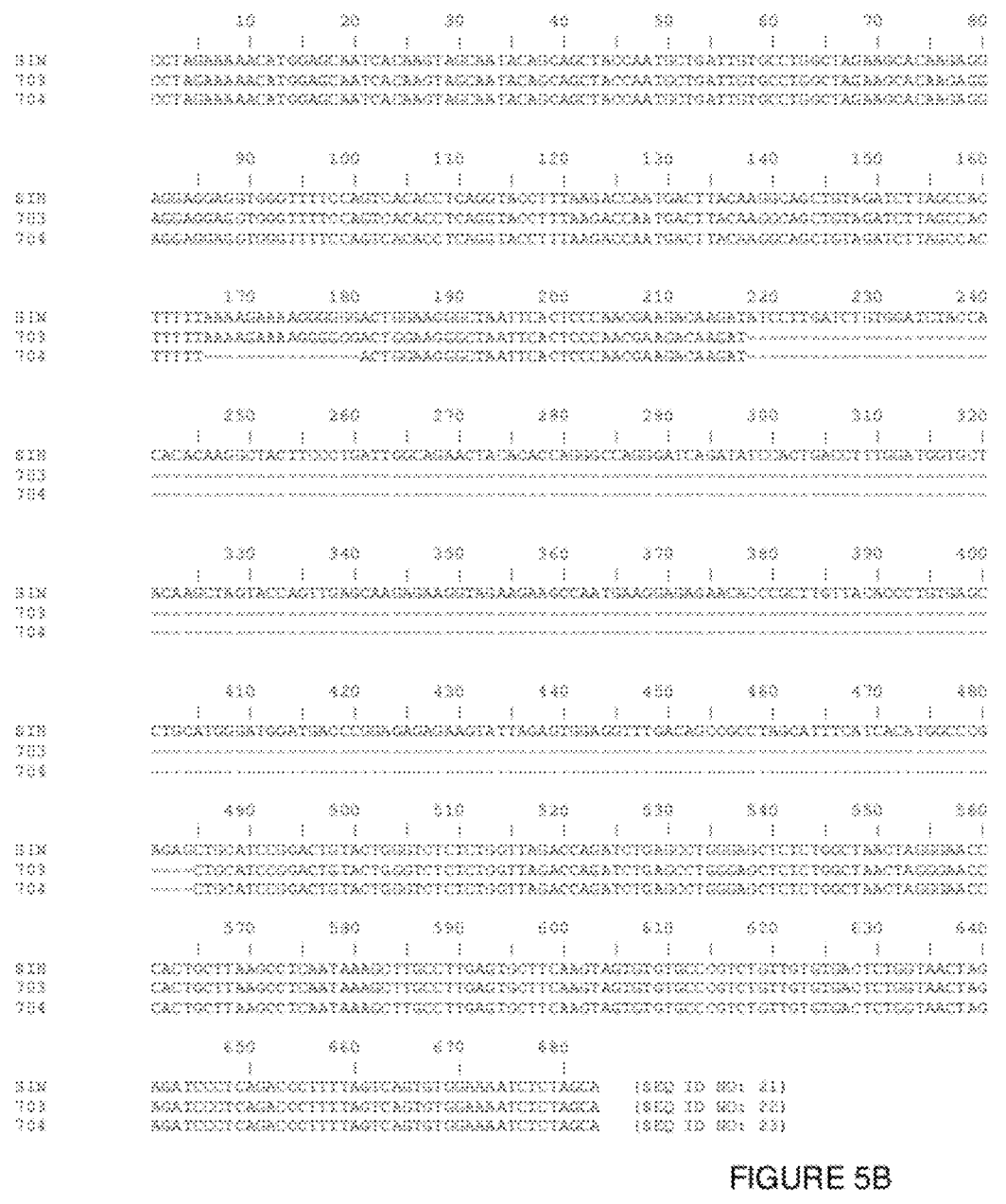

A zoom view of the U3 region is shown below as an open box with the PPT (polypurine tract) sequence immediately upstream. Below are shown three different U3 regions in schematic form; their sequences are shown in FIG. 5B and SEQ ID NOs: 21-23. The constructs contain deletions in the U3 regions. The SIN construct has a deletion of about 130 nucleotides in the U3 (Miyoshi, et al. J Virol 72: 8150, 1998;

Yu et al. PNAS 83: 3194, 1986), which removes the TATA box, abolishing LTR promoter activity. The deletions in constructs 703 and 704 increase expression from lentivirus vectors (Bayer et al. Mol Therapy 16: 1968, 2008, incorporated in its entirety). In addition, construct 704 contains a deletion of the 3' PPT, which decreases integration of the vector (WO 2009/076524, incorporated in its entirety). Sequences of the U3 region of all constructs are shown in FIG. 5B. The 3' PPT begins at position 3, and extended deletions relative to the SIN-deleted vector are shown.

Example 6

Expression in Dendritic Cells Following Transduction with Lentiviral Vector Particles This Example shows the GFP (green fluorescent protein) expression level in dendritic cells generated from vectors with extended U3 deletions.

A series of viruses were produced by transfection of 293T cells as described above. All viruses comprised a SIN-Var1 envelope, a vector genome containing a UbiC or CMV promoter in operative linkage with a GFP transgene, and a deficient integrase by virtue of containing a D64V mutation. Crude supernatants were harvested 48 hours post transduction, and equivalent volumes of each supernatant were used to transduce 293T-DCSIGN cells. GFP expression was determined 72 hours post-transduction using a GUAVA Easy-Cyte flow cytometer. A total of 50,000 events were counted for each transduced cell population. Data was analyzed using FlowJo cytometric analysis software.

Similar results were obtained with both UbiC (FIG. 6, panel A) and CMV (FIG. 6, panel B) promoters. Lentivirus vectors containing extended U3 deletions (703 and 704) showed a higher overall transgene expression relative to SIN deleted vectors. Deletion of the PPT in construct 704 decreased expression slightly relative to construct 703.

Example 7

Vectors with Large Deletions in U3 are Non-Integrating

This example demonstrates the relative integration efficiency of SIN-Var1 pseudotyped vectors containing combinations of different vector deletions with deficient or wild-type integrase following transduction of 293-DC-SIGN cells.

Vector stocks were generated with a number of different combinations of Integrase genes and U3 deletions. Vectors with the U3 deletions (see FIGS. 5A and 5B). SIN, 703, and 704 were transfected as above with either a wild-type integrase gene or a mutant integrase gene. The vectors in these experiments contain a GFP-2A-Neo transgene that encodes both GFP and G418 resistance. The reading frames are linked via a 2A self-cleaving peptide to generate individual proteins. GFP titers for all vector stocks were determined using standard flow cytometric methods. Vector stocks were then used to infect 293-DC-SIGN cells plated the previous day in 6 well dishes at $5 \times 10^5$ cells/well. Following transduction, cells were treated with trypsin every 72 hours. At each passage, $2 \times 10^5$ cells were re-plated into 6 well dishes in 2 mL of DMEM+ 10% FBS. Remaining cells were used to determine the number of GFP+ cells by flow cytometry.

Figure 7:
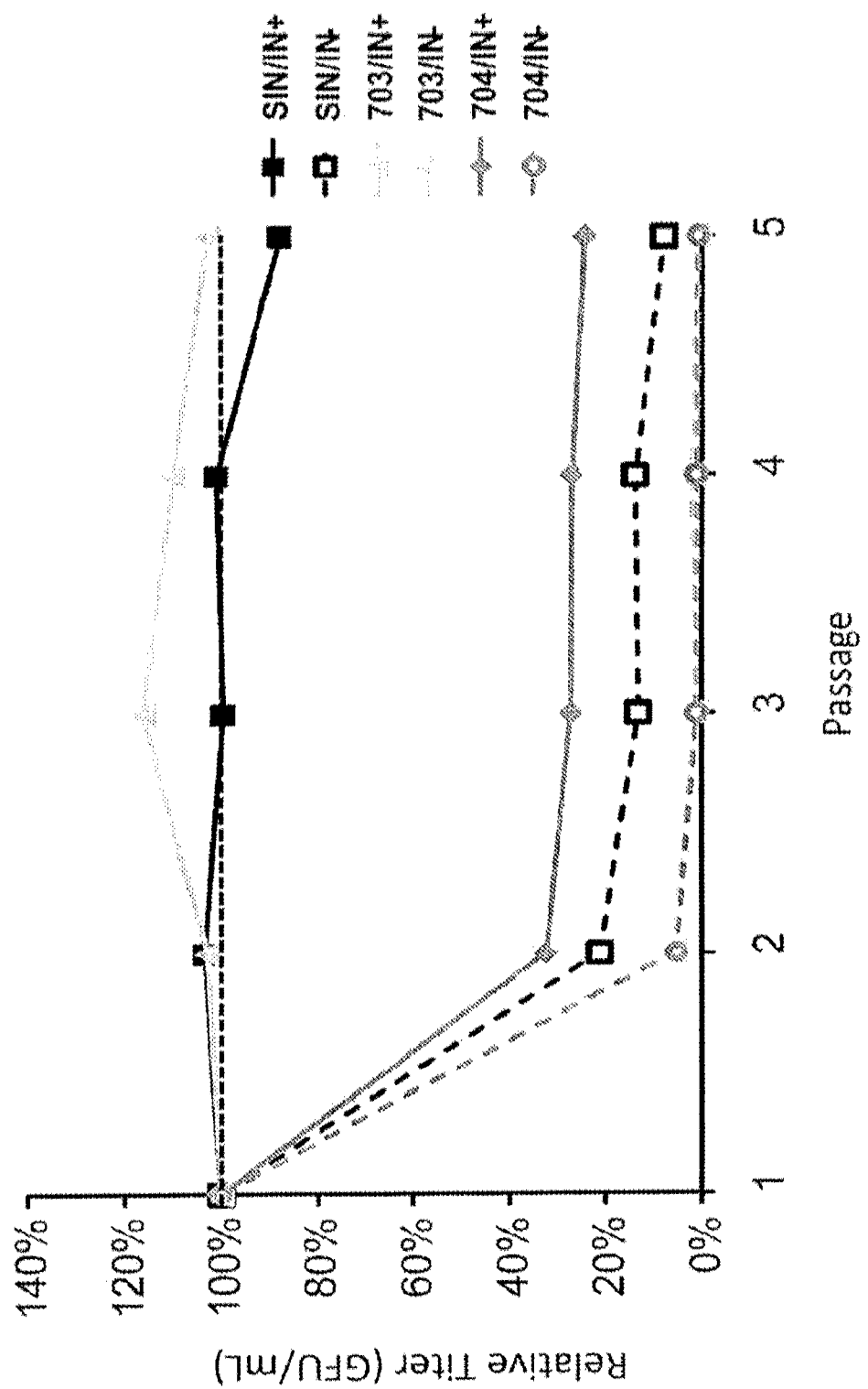
FIG. 7 shows the number of GFP positive cells during five passages. Cells were transduced with different vector preparations and passaged every 72 hrs. Relative GFP titers were determined in 293T cell cultures transduced with different NILV constructs. Vectors were packed using either wild-type Integrase (IN+) or a D64V mutant Integrase (IN−), and used to transduce 293 cells expressing DC-SIGN. Transduced cell cultures were then passaged every 72 hours for 15 days. At each passage, the number of GFP+ cells in the culture was determined using standard flow-cytometric methods. Loss of GFP expression with pass As discussed above, an arbovirus envelope glycoprotein can be used to pseudotype a lentiviral-based vector genome. A "pseudotyped" lentivirus is a lentiviral particle having one or more envelope glycoproteins that are encoded by a virus that is distinct from the lentiviral genome. The envelope glycoprotein may be modified, mutated or engineered as described herein.

In FIG. 7, the relative GFP titer is presented as a fraction of the titer observed at passage one. Loss of GFP expression reflects loss of the GFP transgene, which is a consequence of lack of integration at the initial transduction step. As expected, all viruses containing a D64V mutant integrase (IN−) were found to be non-integrating. In addition, viruses containing a PPT deletion (704) were found to be integration deficient even in the presence of a wild-type IN gene. This shows that deletion of the 3' PPT provides a redundant safety mechanism in combination with an integrase mutation.

Example 8

Integrating and Non-Integrating Lentivirus Vectors are Equivalently Immunogenic

In this Example, CD8 T cell responses are assessed following immunization with integrating or non-integrating viruses.

Figure 8:
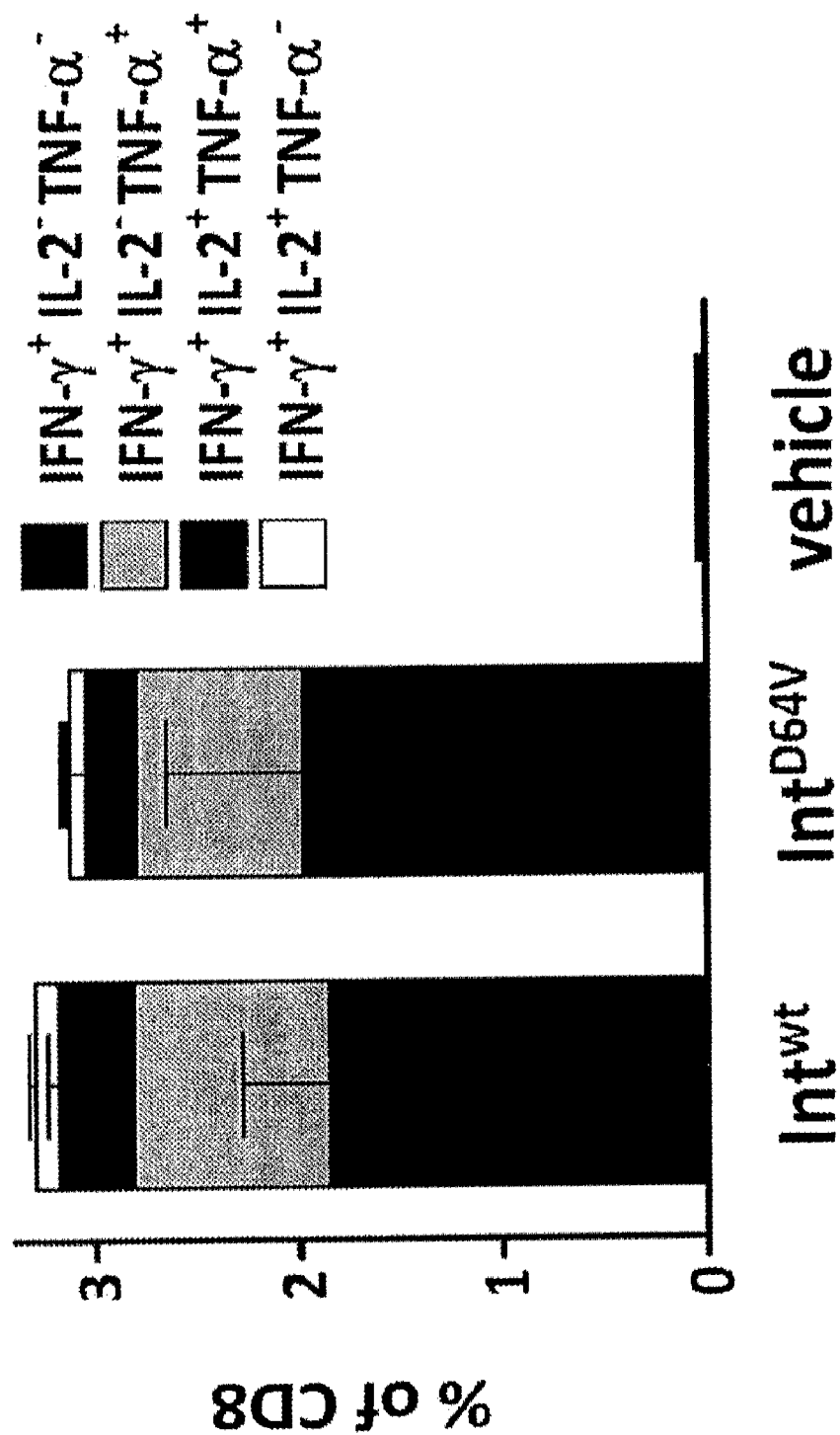

C57BL/6 mice were immunized subcutaneously with $2.5 \times 10^1$ genomes of integrating ($Int^{wt}$) or nonintegrating ($Int^{D64V}$) lentivector encoding the Gag antigen from simian immunodeficiency virus (SIV). The number and function of SIV Gag-specific CD8 T cells in the spleen was determined at day 10 by intracellular cytokine staining, as described above, with the exception that the SW Gag-derived peptide AAVKN-WMTQTL (SEQ ID NO: 29) was used for restimulation. FIG. 8 illustrates that nonintegrating lentivectors can elicit a CD8 T cell response equivalent to integrating lentivectors. Moreover, the pattern of cytokine expression is similar.

Example 9

Immunization with DC-NILV Provide Therapeutic Effect

In this Example, mice that have received tumor cells are treated by immunization with DC-NILV expressing a tumor antigen.

Figure 9:
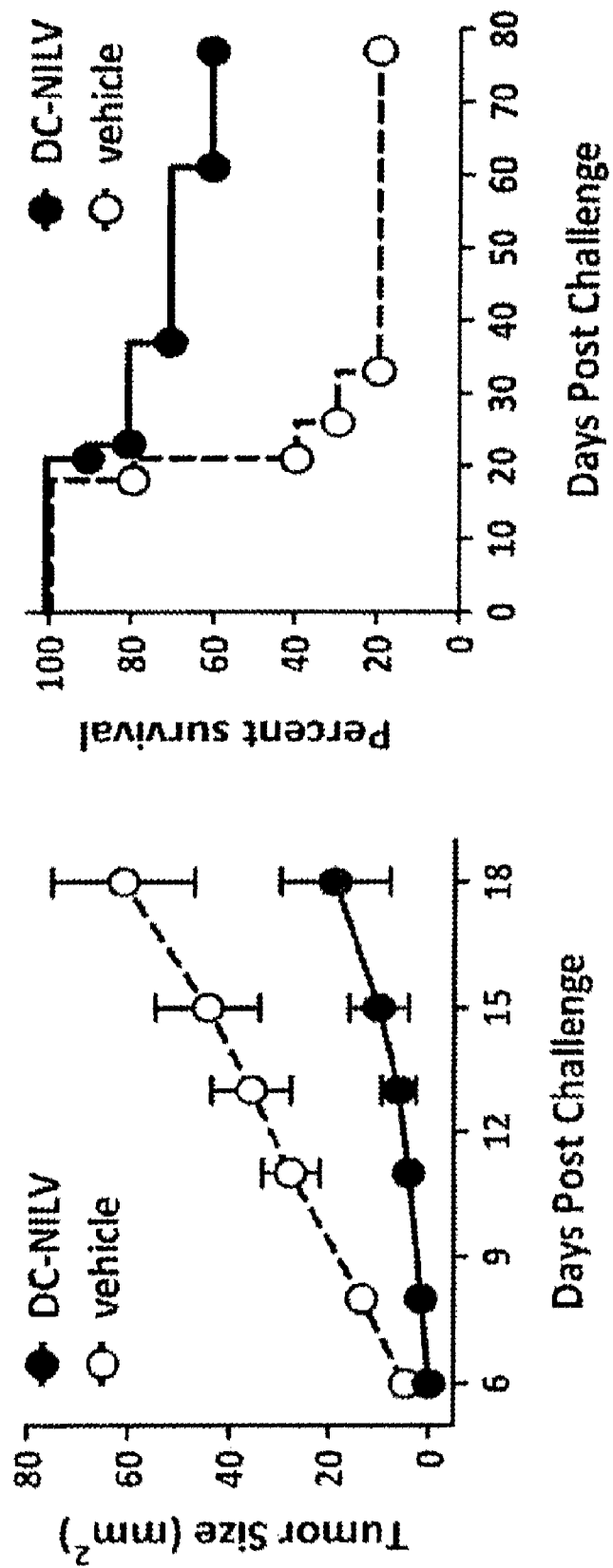

BALB/c mice were injected subcutaneously with $2 \times 10^4$ CT26 colon carcinoma cells. One day later, mice were treated subcutaneously with either vehicle or a SINvar1 pseudotyped lentivirus vector particle preparation containing 3.2 µg of p24 capsid protein. The viral vector envelope comprises a variant of Sindbis virus E2 as described above, and the vector is non-integrating and encodes the AH1A5 peptide (SPSYAY-HQF; SEQ ID NO: 25), a modified MMTV gp70 CD8 T cell epitope that is a rejection antigen relevant to CT26 tumor cells. The initial tumor growth as well as long-term survival of immunized versus control mice is depicted. FIG. 9 shows that the tumor grew more slowly in mice receiving DC-NILV and furthermore, the survival rate (measured out 75 days) was substantially better (60% survival compared to 20%). Therefore, DC-targeting non-integrating lentivectors (DC-NILV) are effective in the therapeutic treatment of tumors.

| SEQUENCE LISTING TABLE | |
|---|---|
| SEQ ID NO: | Name |
| 1 | E2 |
| 2 | SVGmu (E3/E2/6K/E1) |
| 3 | E2 variant 1 (E3/E2/6K/E1) |
| 4 | E2 variant 2 (E3/E2/6K/E1) |
| 5 | E2 variant 3 (E3/E2/6K/E1) |
| 6 | E2 variant 4 (E3/E2/6K/E1) |
| 7 | E2 variant 5 (E3/E2/6K/E1) |
| 8 | E2 variant 6 (E3/E2/6K/E1) |
| 9 | E2 variant 7 (E3/E2/6K/E1) |
| 10 | E2 variant 8 (E3/E2/6K/E1) |
| 11 | E2 variant 9 (E3/E2/6K/E1) |
| 12 | E2 variant 10 (E3/E2/6K/E1) |

SEQUENCE LISTING TABLE

| SEQ ID NO: | Name |
|---|---|
| 13 | E2 variant 11 (E3/E2/6K/E1) |
| 14 | E2 variant 12 (E3/E2/6K/E1) |
| 15 | E2 variant 13 (E3/E2/6K/E1) |
| 16 | E2 variant 14 (E3/E2/6K/E1) |
| 17 | E3/E2/6K/E1 - HR strain |
| 18 | E2 - HR strain |
| 19 | E3 - HR strain |
| 20 | E3/E2 - HR strain |
| 21 | SIN vector - 3' portion |
| 22 | 703 vector - 3' portion |
| 23 | 704 vector - 3' portion |
| 24 | OVA peptide |
| 25 | AH1A5 peptide |
| 26 | E3 peptide |
| 27 | E3 peptide |

We claim:

1. A lentiviral vector particle capable of infecting dendritic cells comprising:
   (a) an envelope comprising an E2 glycoprotein variant having at least 90% identity to amino acids 66 to 488 of SEQ ID NO: 3, wherein (i) residue 160 of the E2 glycoprotein variant (corresponding to amino acid 225 of SEQ ID NO: 3) is absent or is an amino acid other than glutamic acid, (ii) residue 70 of the E2 glycoprotein variant is a non-basic residue, and (iii) the E2 glycoprotein variant is not part of a fusion protein with Sindbis virus E3 glycoprotein; and (b) a lentiviral vector genome comprising a nucleotide sequence encoding an antigen.

2. The lentiviral vector particle of claim 1, wherein the E2 glycoprotein variant binds to DC-SIGN.

3. The lentiviral vector particle of claim 1, wherein residue 160 is absent or is glycine, alanine, valine, leucine or isoleucine.

4. The lentiviral vector particle of claim 1, wherein residue 160 is glycine.

5. The lentiviral vector particle of claim 1, wherein the E2 glycoprotein variant amino acid sequence is amino acid residues 66 to 488 of SEQ ID NO: 3, amino acid residues 66 to 488 of SEQ ID NO: 4, or amino acid residues 66 to 486 of SEQ ID NO: 5, or a variant thereof having at least 95% identity to amino acid residues 66 to 488 of SEQ ID NO: 3, amino acid residues 66 to 488 of SEQ ID NO: 4, or amino acid residues 66 to 486 of SEQ ID NO: 5.

6. The lentiviral vector particle of claim 1, wherein the nucleotide sequence encoding an antigen encodes a tumor-specific antigen or a virus-derived antigen.

7. The lentiviral particle of claim 6, wherein the tumor-specific antigen is selected from the group consisting of carbonic anhydrase IX, NY-ESO-1, MAGE, BAGE, RAGE, MART-1/Melan-A, gp100, gp75, mda-7, tyrosinase, tyrosinase-related protein, 5T4, SM22-alpha, carbonic anhydrase I, HIF-1alpha, HIF-2alpha, PSMA, PSA, STEAP, and NKX3.1.

8. The lentiviral vector particle of claim 6 wherein the virus-derived antigen is an HIV antigen, an SIV antigen, an adenovirus antigen, an enterovirus antigen, a coronavirus antigen, a calicivirus antigen, a distemper virus antigen, an Ebola virus antigen, a flavivirus antigen, a hepatitis virus antigen, a herpesvirus antigen, an infectious peritonitis virus antigen, an influenza virus antigen, a leukemia virus antigen, a Marburg virus antigen, an orthomyxovirus antigen, a papilloma virus antigen, a parainfluenza virus antigen, a paramyxovirus antigen, a parvovirus antigen, a pestivirus antigen, a picorna virus antigen, a poliovirus antigen, a pox virus antigen, a rabies virus antigen, a reovirus antigen, a retrovirus antigen, or a rotavirus antigen.

9. The lentiviral particle of claim 1, wherein the lentiviral vector genome has an inactivated 3' long terminal repeat (LTR) or a self-inactivating 3' long terminal repeat (LTR).

10. The lentiviral particle of claim 9, wherein the lentiviral vector genome comprises a U3 element lacking at least one of an enhancer sequence, a TATA box, an Sp1 site, an NK-kappa B site, or a polypurine tract (PPT).

11. The lentiviral particle of claim 1 wherein the lentiviral vector genome comprises a U3 element lacking at least one of an enhancer sequence, a TATA box, an Spl site, an NK-kappa B site, and a polypurine tract (PPT).

12. The lentiviral particle of claim 1, wherein the lentiviral vector genome comprises the nucleotide sequence of any one of SEQ ID NOs: 21, 22, or 23.

13. The lentiviral particle of claim 1, wherein the lentiviral vector genome further comprises a nucleotide sequence encoding a dendritic cell maturation/stimulatory factor.

14. The lentiviral particle of claim 13, wherein the dendritic cell maturation/stimulatory factor is selected from the group consisting of GM-CSF, IL-2, IL-4, IL-6, IL-7, IL-15, IL-21, IL-23, TNFα, B7.1, B7.2, 4-1BB, CD40 ligand, and drug-inducible CD40.

15. The lentiviral particle of claim 1, wherein expression of the nucleotide sequence encoding an antigen is controlled by a promoter selected from the group consisting of the human Ubiquitin-C promoter (UbiC), the cytomegalovirus immediate early promoter (CMV), the Rous sarcoma virus promoter (RSV), and the tetracycline-responsive promoter.

16. A lentiviral vector particle comprising:
   (a) an envelope comprising a Sindbis virus E2 glycoprotein variant at least 90% identical to residues 66 to 488 of SEQ ID NO: 3, in which:
      (i) the E2 glycoprotein variant is not part of a fusion protein with Sindbis virus E3 glycoprotein;
      (ii) residue 160 of the E2 glycoprotein variant is absent or is an amino acid other than glutamic acid;
      (iii) residue 70 of the E2 glycoprotein variant is replaced with glutamic acid or aspartic acid,
      (iv) residue 159 of the E2 glycoprotein variant is replaced with glutamic acid or aspartic acid; and
      (v) residues 71-75 of the E2 glycoprotein variant are unchanged;
   wherein the E2 glycoprotein variant is capable of binding dendritic cells; and
   (b) a lentiviral vector genome comprising a nucleotide sequence encoding an antigen.

17. The lentiviral particle of claim 16, wherein residue 160 of the E2 glycoprotein variant is replaced with glycine, residue 159 of the E2 glycoprotein variant is replaced with glutamic acid, residue 70 of the E2 glycoprotein variant is replaced with glutamic acid, and wherein the lentiviral vector genome comprises a LTR lacking a polypurine tract (PPT).

18. A lentiviral vector particle comprising:
   (a) a Sindbis virus E2 glycoprotein variant comprising residues 66 to 488 of SEQ ID NO: 3, wherein the E2 glycoprotein variant is not part of a fusion protein with Sindbis virus E3 glycoprotein; and
   (b) a lentiviral vector genome comprising a nucleotide sequence encoding an antigen.

19. The lentiviral particle of claim 16, wherein the lentiviral vector genome comprises the nucleotide sequence of SEQ ID NO: 21.

20. The lentiviral particle of claim 16, wherein the lentiviral vector genome comprises the nucleotide sequence of SEQ ID NO: 22.

21. The lentiviral particle of claim 16, wherein the lentiviral vector genome comprises the nucleotide sequence of SEQ ID NO: 23.

22. A pharmaceutical composition comprising a plurality of lentiviral particles of claim 1 and a pharmaceutically acceptable excipient.

23. The pharmaceutical composition of claim 22, the wherein the lentiviral particles have an IU of at least $10^5$/mL.

24. A pharmaceutical composition comprising a plurality of lentiviral particles of claim 16 and a pharmaceutically acceptable excipient.

25. The lentiviral particle of claim 1 wherein the lentiviral vector genome further comprises a nucleotide sequence encoding a second antigen.

26. The pharmaceutical composition of claim 22 further comprising an immunostimulating agent.

27. The pharmaceutical composition of claim 22 further comprising an adjuvant.

28. The lentiviral particle of claim 1 wherein residue 76 of the E2 glycoprotein variant is a non-basic residue.

29. The lentiviral particle of claim 1 wherein residue 159 of the E2 glycoprotein variant is a non-basic residue or is absent.

30. The lentiviral particle of claim 28 wherein residue 159 of the E2 glycoprotein variant is a non-basic residue or is absent.

\* \* \* \* \*

UNITED STATES PATENT AND TRADEMARK OFFICE
CERTIFICATE OF CORRECTION

| | | |
|---|---|---|
| PATENT NO. | : 8,187,872 B2 | Page 1 of 1 |
| APPLICATION NO. | : 13/277900 | |
| DATED | : May 29, 2012 | |
| INVENTOR(S) | : James M. Allen et al. | |

It is certified that error appears in the above-identified patent and that said Letters Patent is hereby corrected as shown below:

On the title page item (75), under "Inventors", in Column 1, Lines 4-5, delete "Neal Van Hoeven," and insert -- Neal S. Van Hoeven -- therefor.

In the claims,

In Column 131, Line 55, in Claim 16, delete "acid," and insert -- acid; -- therefor.

In Column 132, Lines 34-35, in Claim 23, delete "the wherein" and insert -- wherein -- therefor.

Signed and Sealed this
Twenty-second Day of December, 2015

Michelle K. Lee
*Director of the United States Patent and Trademark Office*